(12) United States Patent
Rea et al.

(10) Patent No.: US 6,489,537 B1
(45) Date of Patent: Dec. 3, 2002

(54) PHYTOCHELATIN SYNTHASES AND USES THEREFOR

(75) Inventors: Philip A. Rea, Ardmore, PA (US); Olena K. Vatamaniuk, Philadelphia, PA (US); Stephane Mari, Jenkintown, PA (US); Yu-Ping Lu, Oak Park, CA (US); Julian I. Schroeder, La Jolla, CA (US); Eugene J. Kim, San Diego, CA (US); Stephan Clemens, Halle (DE)

(73) Assignees: The Trustees of the University of Pennsylvania, Philadelphia, PA (US); University of California, La Jolla, CA (US)

( * ) Notice: Subject to any disclaimer, the term of this patent is extended or adjusted under 35 U.S.C. 154(b) by 0 days.

(21) Appl. No.: 09/354,123

(22) Filed: Jul. 15, 1999

Related U.S. Application Data

(63) Continuation-in-part of application No. 09/315,449, filed on May 20, 1999, now abandoned.
(60) Provisional application No. 60/095,624, filed on Aug. 7, 1998.

(51) Int. Cl.[7] .................. C12N 15/09; C12N 15/29; C12N 15/31; C12N 15/82; A01H 5/00
(52) U.S. Cl. .................. 800/278; 800/298; 800/295; 800/288; 800/320.3; 800/306; 435/69.1; 435/320.1; 435/419; 435/468; 536/23.1; 536/23.2; 536/23.6; 536/23.7
(58) Field of Search .................. 800/298, 278, 800/295, 320.3, 288, 306; 536/23.1, 23.2, 23.6, 23.7; 435/69.1, 320.1, 419, 468

(56) References Cited

U.S. PATENT DOCUMENTS

| | | | |
|---|---|---|---|
| 5,023,243 A | 6/1991 | Tullis | 514/44 |
| 5,168,053 A | 12/1992 | Altman et al. | 435/91 |
| 5,190,931 A | 3/1993 | Inouye | 435/91 |
| 5,364,451 A | * 11/1994 | Raskin et al. | 210/602 |
| 5,965,796 A | * 10/1999 | Meagher et al. | 800/298 |

OTHER PUBLICATIONS

Vatamaniuk et al. The Journal of Biological Chemistry, vol. 275, No. 40, pp. 31451–31459, Jun. 2000.*
Arisi et al. Planta, vol. 203, pp. 362–372, 1997.*
Noctor et al. Journal of Experimental Botany, vol. 49, No. 321, pp. 623–647, Apr. 1998.*
Newman et al. Accession No. W43439, Sequence Search Result, p. 3, Jan. 1998.*
Sambrooke et al. A Laboratory Manual, 2nd Edition, 1989.*
Gietz et al., "Transforming Yeast With DNA," *Methods in Molecular and Cellular Biology*, 5:255–269 (1995).

Stadtman, "Metal Ion–Catalyzed Oxidation of Proteins: Biochemical Mechanism and Biological Consequences," *Free Radical Biology & Medicine*, vol. 9, pp. 315–325, 1990.
Altschul et al., "Basic Local Alignment Search Tool," *J. Mol. Biol.* 215:403–410 (1990).
Anderson et al., "Functional expression of a probable *Arabidopsis thaliana* potassium channel in *Saccharomyces cerevisiae*," *Proc. Natl. Acad. Sci. U.S.A.* 89:3736–3740 (1992).
Baulcombe, "Fast forward genetics based on virus–induced gene silencing," *Curr. Opinion Plant Biol.* 2:109–113 (1999).
Bevan, "Binary Agrobacterium vectors for plant transformation," *Nucl. Acids Res*, 12:8711–8721 (1984).
Bradford, "A Rapid and Sensitive Method for the Quantitation of Microgram Quantities of Protein Utilizing the Principle of Protein–Dye–Binding," *Anal. Biochem.* 72:248–254 (1976).
Cech, "Ribozymes and Their Medical Implications," *J. Amer. Med. Assn.* 260:3030 (1988).
Cech et al., "RNA Catalysis by a Group I Ribozyme," *J. Biol. Chem.*, 267:17479–17482 (1992).
Chen et al., "Characterization of phytochelatin synthase from tomato," *Physiol. Plant.* 101:165–172 (1997).
Clemens et al., "The plant cDNA LCT1 mediates the uptake of calcium and cadmium in yeast," Proc. *Natl. Acad. Sci. U.S.A.*, 95:12043–12048 (1988).
Cunningham et al., "Phytoremediation of contaminated soils," *Trends Biotechnol.* 13:393–397 (1995).
Cunningham et al., "Promises and Prospects of Phytoremediation," *Plant Physiol.* 110:715–719 (1996).
Fahey and Newton, "Determination of Low–Molecular–Weight Thiols Using Monobromobimane Fluorescent Labeling and High–Performance Liquid Chromatography," *Meth. Enzymol.* 143:85–97 (1987).
Freedman et al., "The Role of Glutathione in Cooper Metabolism and Toxicity," *J. Biol. Chem.* 44264:5598–5605 (1989).
Fuhr and Rabenstein, "Nuclear Magnetic Resonance Studies of the Solution Chemistry of Metal Complexes," *J. Am. Chem. Soc.* 95:6944–6950 (1973).
Gietz and Schiestl, "applications of High Efficiency Lithium Acetate Transformation of Intact Yeast Cells using Single–Stranded Nucleic Acids as Carrier," *Yeast* 7:253–263 (1991).
Grill et al., "Phytochelatins: The Principal Heavy–Metal Complexing Peptides of Higher Plants," *Science* 230:674–676 (1985).

(List continued on next page.)

Primary Examiner—David T. Fox
Assistant Examiner—Medina A. Ibrahim
(74) Attorney, Agent, or Firm—Dilworth Paxson LLP

(57) ABSTRACT

The present invention relates to novel phytochelatin synthases and uses thereof.

18 Claims, 26 Drawing Sheets

OTHER PUBLICATIONS

Grill et al., "Phytochelatins, the heavy–metal–binding peptides of plants, are synthesized from glutathione by a specific γ–glutamylcysteine dipeptidyl transpeptidase (phytochelatin synthase)," *Proc. Natl. Acad. Sci. USA* 86:6838–6842 (1989).

Grill et al., "Phytochelatins, a class of heavy–metal–binding peptides from plants, are functionally analogous to metallothioneins," *Proc. Natl. Acad. Sci. U.S.A.* 84:439–443 (1987).

Hamer, "Metallothionein," *Annu. Rev. Biochem.* 55:913–951 (1986).

Hamer et al., "Function and Autoregulation of Yeast Copperthionein," *Science* 228:685–690 (1985).

Hampel et al., "RNA Catalytic Properties of the Minimum (–)sTRSV Sequence," *Biochemistry* 28:4929–4933 (1989).

Haselhoff and Gerlach, "Simple RNA enzymes with new and highly specific endoribonuclease activities," *Nature* 334:585 (1988).

Higgins and Sharp, "CLUSTAL: a package for performing multiple sequence alignment of a microcomputer," *Gene* 73:237–240 (1988).

Ho et al., "Isolation of Vacuolar Membrane $H^+$–ATPase–deficient Yeast Mutants; the VMA5 and VMA4 Genes Are Essential for Assembly and Activity of the Vacuolar $H^+$–ATPase," *J. Biol. Chem.* 268:221–227 (1993).

Hofmann and Stoffel, "A Database of Membrane Spanning Protein Segments," *Biol. Chem.* 347:166 (1993).

Horsch et al., "Leaf Disc Transformation," *Plant Molecular Biology Manual* A5:1–9 (1988).

Howden et al., "Cadmium–Sensitive, cad1 Mutants of *Arabidopsis thaliana* Are Phytochelatin Deficient," *Plant Physiol.* 107:1059–1066 (1995).

Inoue et al., "Molecular identification of glutathione synthetase (GSH2) gene from *Saccharomyces cerevisiae*," *Biochem. Biophys. Acta* 1395:315–320 (1998).

Inzé and Van Montagu, "Oxidative stress in plants," *Current Opinion in Biotech.* 6:153–158 (1988).

Jefferson et al. "GUS fusions: β–glucuronidase as a sensitive and versatile gene fusion market in higher plants," *EMBO J.*, 6:3901–3907 (1987).

Kim et al., "Heterologous expression of plant vacuolar pyrophosphatase in yeast demonstrates sufficiency of the substrate–binding subunit for proton transport," *Proc. Natl. Acad. Sci. USA* 91:6128–6132 (1994).

Kneer et al., "*Saccharomyces cerevisiae* and *Neurosporoa crassa* contain heavy metal sequestering phytochelatin," *Arch. Microbiol.* 157:305–310 (1992).

Lagrimini et al., "Peroxidase–Induced Wilting in Transgenic Tobacco Plants," *Plant Cell* 2:7–18 (1990).

Li et al., "A new pathway for vacuolar cadmium sequestration in *Saccharomyces cerevisiae*: YCF1–catalyzed transport of bis(glutathionateo)cadmium," *Proc. Natl. Acad. Sci. U.S.A.* 94:42–47 (1997).

Li et al., "The Yeast Cadmium Factor Protein (YCF1) is a Vacuolar Glutathione S–Conjugate Pump," *J. Biol. Chem.* 271:6509–6517 (1996).

Lu et al., "atMRP1 gene of Arabidopsis encodes a glutathione S–conjugage pump: Isolation and funcional definition of a plant ATP–binding cassette transporter gene," *Proc. Natl. Acad. Sci. U.S.A.* 94:8243–8247 (1997).

Marcus–Sakura, "Techniques for Using Antisense Oligodeoxyribonucleotides to Study Gene Expression," *Anal. Biochem.* 172:289 (1988).

Meuwly et al., "Three families of thiol peptides are induced by cadmium in maize," *Plant J.* 7:391–400 (1995).

Mewes et al., "Overview of the yeast genome," *Nature* 387:7–65 (1997).

Minet et al., "Complementation of *Saccharomyces cerevisiae* auxotrophic mutants by *Arabidopsis* cDNAs," *Plant J.* 2:417–422 (1992).

Murphy and Taiz, "Comparison of Metallothionein Gene Expression and Nonprotein Thiols in Ten Arabidopsis Ecotypes," *Plant Physiol.* 109:945–954 (1995).

Murphy et al., "Purification and Immunological Identification of Metallothioneins 1 and 2 from *Arabidopsis thaliana*," *Plant Physiol.* 113:1291–1301 (1997).

Mutoh and Hayashi, "Isolation of Mutants of *Schizosaccharomyces Pombe* Unable To Synthesize Cadystin, Small Cadmium–Binding Peptides," *Biochem. Biophys. Res. Commun.* 151:32–39 (1988).

Napoli et al., "Introduction of a Chimeric Chalcone Synthase Gene into Petunia Results in Reversible Co–Suppression of Homologous Genes in trans," *Plant Cell.* 2:291–299 (1990).

Nriagu and Pacyna, "Quantitative assessment of worldwide contamination of air, water and soils by trace metals," *Nature* 333:124–138 (1988).

Okazaki et al., "High–frequency transformation method and library transducing vectors for cloning mammalian cDNAs by trans–complementation of *Schizosaccharomyces pombe*," *Nucleic Acids Res.* 25:6485–6489 (1990).

Ortiz et al., "Transport of Metal–binding Peptides by HMT1, A Fission Yeast ABC–type Vacuolar Membrane Protein," *J. Biol. Chem.* 270:4721–4728 (1995).

Ortiz et al., "Heavy metal tolerance in the fission yeast requires an ATP–binding cassette–type vacuolar membrane transporter," *EMBO J.* 11:3491–3499 (1992).

Raskin, "Plant genetic engineering may help with environmental cleanup," *Proc. Natl. Acad. Sci. USA*, 93:3164–3166 (1996).

Rauser, "Phytochelatins," *Annu. Rev. Biochem.* 59:61–86 (1990).

Rauser, "Phytochelatins and Related Peptides," *Plant Physiol.* 109:1141–1149 (1995).

Rea et al., "From Vacuolar GS–X Pumps to Multispecific ABC Transporters," *Plant Mol. Biol.* 49:727–760 (1998).

Robinson et al., "A Putative Zinc Finger Protein, *Saccharomyces cerevisiae* Vps18p, Affects Late Golgi Functions Required for Vacuolar Protein Sorting and Efficient α–Factor Prohormone Maturation," *Mol. Cell. Biol.* 11:5813–5824 (1991).

Rodriquez–Navarro and Ramos, "Dual System for Potassium Transport in *Saccharomyces cerevisiae*," *J. Bacterial.* 159:940–945 (1984).

Schachtman and Schroeder, "Structure and transport mechanism of a high–affinity potassium uptake transporter from higher plants," *Nature* 370:655–658 (1994).

Silver and Phung, "Bacterial Heavy Metal Resistance: New Surprises," *Annu. Rev. Microbiol.* 50:753–789 (1996).

Steffans, The Heavy Metal–Binding Peptides of Plants, *Annu. Rev. Plant Physiol. Plant Mol. Biol.* 41:553–575 (1990).

Strathern and Higgins, "Recovery of Plasmids from Yeast into *Escherichia coli*: Shuttle Vectors," *Methods Enzymol.* 194:319–329 (1991).

Szczypka et al., "A Yeast Metal Resistance Protein Similar to Human Cystic Fibrosis Transmembrane Conductance Regulator (CFTR) and Multidrug Resistance–associated Protein," *J. Biol. Chem.* 269:22853–22857 (1994).

Thompson et al., "Clustal W: improving the sensitivity of progressive multiple sequence alignment through sequence weighting, position–specific gap penalties and weight matrix choice," *Nuc. Acids Res.* 22:4673–4680 (1994).

Thumann et al., "Reactivation of metal–requiring apoenzymes by phytochelatin–metal complexes," *FEBS Lett.* 284:66–69 (1991).

Udenfriend et al., "Fluorescamine: A Reagent for Assay of Amino Acids, Peptides, Proteins, and Primary Amines in the Picomole Range," *Science* 178:871–874 (1972).

Valvekens et al., *Agrobactgerium tumefaciens*–mediated transformation of *Arabidopsis thaliana* root explants by using kanamycin selection, Proc. *Natl. Acad. Sci. U.S.A.* 85:5536–5540 (1988).

van der Krol et al., "Antisense genes in plants: an overview," *Gene* 72:45–50 (1988).

Vogeli–Lange and Wagner, "Subcellular Localization of Cadmium and Cadmium–Binding Peptides in Tobacco Leaves," *Plant Physiol.*, 92:1086–1093 (1990).

Weintraub, "Antisense RNA and DNA," *Scientific American* 262:40 (1990).

Wemmie et al., "Transcriptional Activation Mediated by the Yeast AP–1 Protein is Required for Normal Cadmium Tolerance," *J. Biol. Chem.* 269:14690–14697 (1994).

Zenk, "Heavy metal detoxification in higher plants–a review," *Gene* 179:21–30 (1996).

Zhou and Goldsbrough, "Functional Homologs of Fungal Metallothionein Genes from Arabidopsis," *Plant Cell* 6:875–884 (1994).

Hayashi et al., "Two pathways in the biosynthesis of cadystins $(\gamma EC)_n G$ in the cell–free system of the fission yeast," *Biochem. Cell. Biol.*, vol. 69, 115–121 (1991).

Kondo et al., "Synthesis of Metallothionein–like Peptides Cadystin A and B Occurring in a Fission Yeast, and Their Isomers," *Agric. Biol. Chem.*, vol. 49(1), 71–83 (1985).

Salt et al., "Cadmium Transport across Tonoplast of Vesicles from Oat Roots," *J. Biol. Chem.*, 268:17, 12297–12302 (1993).

van der Krol et al., "Flavenoid Genes in Petunia: Addition of a Limited Number of Gene Copies May Lead to a Suppression of Gene Expression," *Plant Cell*, vol. 2, 291–299 (1990).

* cited by examiner

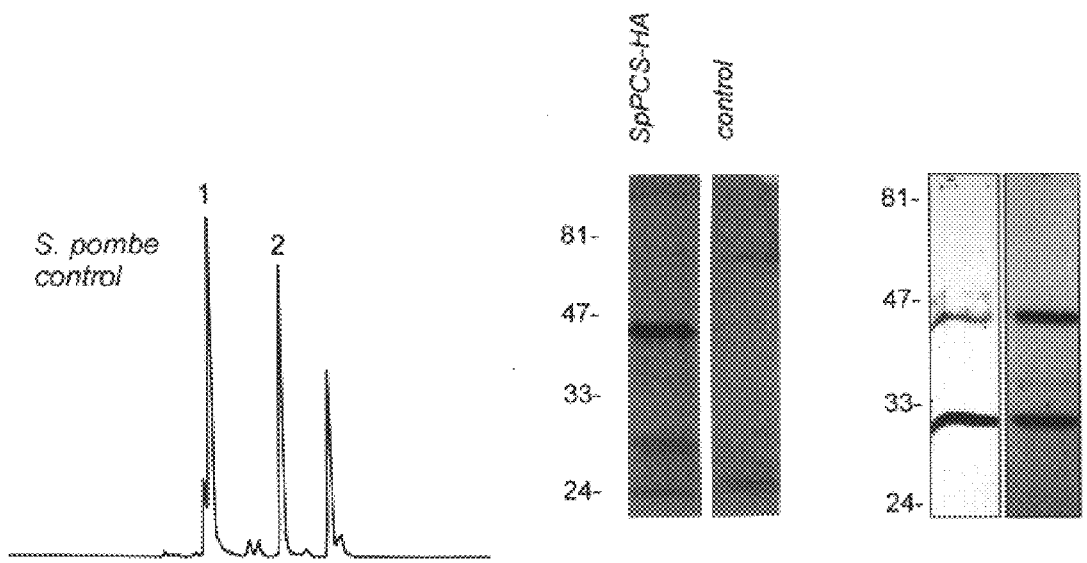
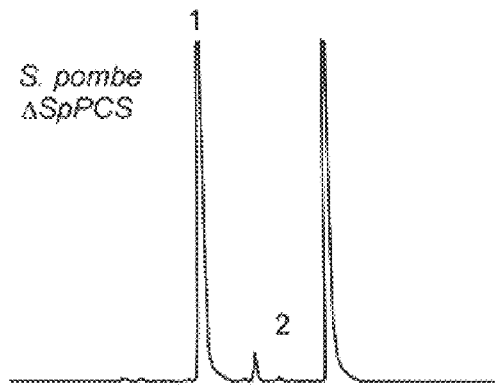
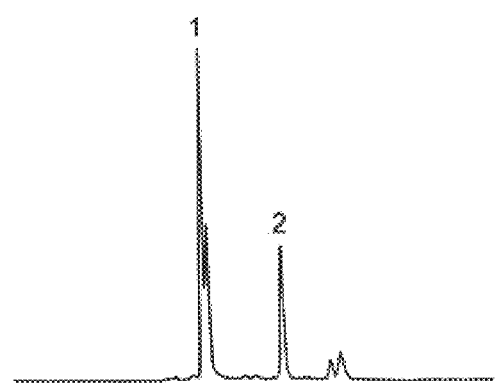
FIG. 14A  FIG. 14B  FIG. 14C  FIG. 14D

|  10 |  20 |  30 |  40 |  50 |  60 |
|---|---|---|---|---|---|
| agtaatttag | gttattttcg | aatccactaa | cgaatcttcc | acagcaaaca | cttttgtgtt |
|  70 |  80 |  90 | 100 | 110 | 120 |
| cctctgtaat | ttctcagtat | atatagatac | caaaacaagc | agtgaaaaAT | GGCTATGGCG |
| 130 | 140 | 150 | 160 | 170 | 180 |
| AGTTTATATC | GGCGATCTCT | TCCTTCTCCT | CCGGCCATTG | ACTTTTCTTC | CGCCGAAGGC |
| 190 | 200 | 210 | 220 | 230 | 240 |
| AAGCTAATCT | TCAATGAAGC | GCTTCAAAAA | GGAACTATGG | AAGGATTTTT | CAGGTTGATT |
| 250 | 260 | 270 | 280 | 290 | 300 |
| TCGTATTTTC | AGACACAATC | CGAACCTGCG | TATTGTGGTT | TGGCTAGTCT | CTCAGTGGTG |
| 310 | 320 | 330 | 340 | 350 | 360 |
| TTGAATGCTC | TTTCTATCGA | TCCTGGACGT | AAATGGAAAG | GGCCTTGGAG | GTGGTTTGAT |
| 370 | 380 | 390 | 400 | 410 | 420 |
| GAATCAATGT | TGGATTGCTG | CGAACCTCTG | GAAGTAGTGA | AGGAAAAAGG | CATTTCATTT |
| 430 | 440 | 450 | 460 | 470 | 480 |
| GGAAAAGTTG | TCTGTTTGGC | TCATTGTTCA | GGAGCAAAAG | TTGAGGCTTT | CCGTACAAGT |
| 490 | 500 | 510 | 520 | 530 | 540 |
| CAGAGCACCA | TTGATGATTT | CCGCAAATTT | GTCGTCAAAT | GCACGAGTTC | TGAGAATTGT |
| 550 | 560 | 570 | 580 | 590 | 600 |
| CATATGATCT | CAACATATCA | CCGAAGTGTA | TTTAAGCAGA | CTGGGAATGG | TCACTTTTCA |
| 610 | 620 | 630 | 640 | 650 | 660 |
| CCTATTGGTG | GCTATAATGC | TGAGAGAGAT | ATGGCTTTGA | TTCTTGATGT | TGCTCGTTTC |
| 670 | 680 | 690 | 700 | 710 | 720 |
| AAGTATCCCC | CTCACTGGGT | TCCTCTTAAA | CTTCTTTGGG | AAGCCATGGA | CAGTATTGAT |
| 730 | 740 | 750 | 760 | 770 | 780 |
| CAGTCAACAG | GGAAACGTAG | AGGGTTCATG | CTCATATCTA | GACCACACAG | AGAACCCGGA |
| 790 | 800 | 810 | 820 | 830 | 840 |
| TTGCTCTATA | CTCTGAGCTG | CAAGGATGAA | AGCTGGATCG | AAATAGCCAA | GTATTTGAAG |
| 850 | 860 | 870 | 880 | 890 | 900 |
| GAAGATGTTC | CTCGTCTTGT | AAGTTCACAG | CATGTAGATT | CTGTGGAGAA | AATCATATCA |
| 910 | 920 | 930 | 940 | 950 | 960 |
| GTTGTGTTCA | AGTCACTTCC | ATCAAATTTC | AACCAATTCA | TCAGATGGGT | GGCTGAGATC |
| 970 | 980 | 990 | 1000 | 1010 | 1020 |
| CGAATTACAG | AGGACTCAAA | CCAAAATCTC | AGCGCAGAGG | AGAAGTCTAG | GCTGAAACTA |
| 1030 | 1040 | 1050 | 1060 | 1070 | 1080 |
| AAGCAATTGG | TGCTGAAGGA | AGTGCACGAA | ACTGAACTGT | TCAAACACAT | CAATAAGTTC |
| 1090 | 1100 | 1110 | 1120 | 1130 | 1140 |
| TTATCCACAG | TGGGTTATGA | AGACAGTCTG | ACTTATGCTG | CTGCAAAGGC | TTGTTGCCAA |
| 1150 | 1160 | 1170 | 1180 | 1190 | 1200 |
| GGAGCTGAAA | TCTTATCCGG | AAGCCCATCA | AAAGAGTTTT | GTTGTCGGGA | AACTTGCGTG |
| 1210 | 1220 | 1230 | 1240 | 1250 | 1260 |
| AAATGCATCA | AAGGTCCTGA | TGACTCTGAA | GGCACGGTGG | TGACTGGAGT | TGTGGTGCGT |

FIG. 16A

|  1270        |  1280       |  1290       |  1300       |  1310       |  1320       |
|--------------|-------------|-------------|-------------|-------------|-------------|
| GATGGGAATG   | AACAAAAGGT  | TGATCTGTTA  | GTGCCATCGA  | CGCAAACTGA  | GTGTGAATGT  |
|  1330        |  1340       |  1350       |  1360       |  1370       |  1380       |
| GGTCCTGAAG   | CAACTTATCC  | AGCAGGAAAC  | GATGTGTTCA  | CTGCACTTCT  | ATTGGCTTTA  |
|  1390        |  1400       |  1410       |  1420       |  1430       |  1440       |
| CCTCCACAGA   | CATGGTCAGG  | GATCAAAGAC  | CAAGCTCTTA  | TGCATGAAAT  | GAAGCAGCTC  |
|  1450        |  1460       |  1470       |  1480       |  1490       |  1500       |
| ATTTCCATGG   | CTTCCCTCCC  | AACTTTGCTT  | CAAGAAGAGG  | TATTGCATCT  | TCGACGGCAA  |
|  1510        |  1520       |  1530       |  1540       |  1550       |  1560       |
| CTTCAGCTGC   | TAAAACGATG  | CCAAGAGAAC  | AAGGAAGAGG  | ATGATCTCGC  | TGCTCCTGCC  |
|  1570        |  1580       |  1590       |  1600       |  1610       |  1620       |
| TATTAGttca   | ttgtcccaaa  | tcctctctct  | tccccatttg  | aatcccacgt  | tctctacact  |
|  1630        |  1640       |  1650       |  1660       |  1670       |  1680       |
| taattgttag   | aaagtctctt  | tattctctgt  | acgattcaaa  | ctctatttgc  | aatgagagat  |
|  1690        |  1700       |  1710       |  1720       |  1730       |  1740       |
| atatgtaact   | tgcattctat  | aaattgttaa  | tcacaataag  | ttaagaatcc  | aaaaaaaaaa  |
|  1750        |  1760       |  1770       |  1780       |  1790       |  1800       |
| aaactaaa..   | ..........  | ..........  | ..........  | ..........  | ..........  |

FIG. 16B

```
   1 atgtctatgg cgagtttgta tcggcggtct ctttccctc cggcgataga tttgcttct
  61 tttgaaggaa aggtgcgtta tttctcaagt gttcgatcca tggattcaat tgaaaattca
 121 gggttctggg ttttaacttt ttaagtatcc ttgtgcttct ggttagagat gatcactgat
 181 ttggttttg tatgttgatt gattggtta ctctctatc tgtatagagt ctagaaattg
 241 gattttcttg ggaactgtgt aaaactcgta aaaccctaaa cccctgctg tttacaaag
 301 tttagttgtt ggtgagagat ctgagcatgc ttcatgataa atggttcacg aattattgat
 361 agccaattta gtagaatggg acaagttctt ttgccctgag aatttaaatg ttgtcattgt
 421 ctttgcagca aatcttcaat gaagcgcttc agaaaggcac tatggaagga ttttcgggc
 481 tgatttctta ttttcagaca cagtctgagc cagctttttg tggcttagct agtctttcga
 541 tggttttgaa ttctcttct attgacccgg gaagaaagtg gttcctctca catacctcta
 601 ctggagagta catttgttgg tgggttttg aatttttg gcgagccgct gtttcaactt
 661 ggtggtttga tgaatcaatg ctgaatgtt ctgaatagtt aggatagtg tgttcaactt
 721 gcatttcatt ggaaaagtg attgatgatt ctcattcttc gcgagccgct aaggataaag
 781 tccgcacaaa tcagagcacc attgatgatt tcaacatatc aggcaagt gtatcatttt
 841 ctgataattg tcatatgatc atggatctc atatgccagt actcaagcag ttcattagac
 901 tttggcctaa actctgtgta tattaacagt tatatggcaa ttaagtgaa ttcattagac
 961 ttaatgttat tacaaagttt gataatggtg aaactctttc atgtcttgct atgaagtccc
1021 atgctgatcg gattctaatg tctatgattg cagactggaa ctggccactt ttcacctatt
1081 ggtggttata atgctgaaag agatatggct ttgattcttg atgtcgctcg tttcaagtat
1141 cctcctcact gggttcctct taaacttctt tgggatgcca tggatagtat tgatcagtca
1201 acagggagac gtagagggta catgatctc tattcttttt cttaggcttc acttgtatga
1261 ttaaagaatg taatccgttt cttttttgcta tctctgctta cttccaggtt catgcttata
1321 tcaagacccc acagagaacc aggattgctc tatacattag taagtccaaa gtcatggttc
1381 tattagtagt tgctgctatt acaataacat ttctttcgaa taggactgag taatgatatc
```

FIG. 17A

```
1441  ttgattatcg  atttcagagt  tgtaaggatg  agagctggat  cagcattgca  aagtatttga
1501  aggaagatgt  tcctcgtctt  gtaagctcac  aacatgttga  tactattgaa  agaatcttat
1561  atgttgtatt  caagtcactt  ccagcaaatt  tcaaccaatt  tatcaaatgg  atggctgaga
1621  ttcgaagaac  agaggatgta  aatcaaaatc  ttagctcaga  agagaaatca  aggctcaaat
1681  taaggtatt   atcttgtcca  tttgcttctg  aactttagtt  ttccatgttt  atattccatc
1741  agtttattca  tcactgttct  atggttcgtt  ttgctgtagc  aagagttact  gaaacaagtg
1801  caagaaacta  aactgttcaa  gcatgttgga  aagtttctct  cctctgtgta  cgaagacaat
1861  ctgccatatg  ttgctgctaa  ggtttattgt  gacggagatg  aaatcttatc  gggatatgaa
1921  tcagatgaat  cctgttgtaa  ggaaacttgt  gtcaaatgta  tcaaagtat   gtttgttctt
1981  acattctggt  tatctttcta  agcgcttcag  aaaccttggc  ttgaagttag  tagtgtgcaa
2041  agttctaatc  aagaaaatcac tttttctctt  gaattctttg  ttttacatca  aggtcttggt
2101  gaggagaaag  tgacagtggt  agcttaccca  tccgggaacg  atgtgttcac  tgctcttctg
2161  ttggctttac  ctccacagac  gtggtcaggt  atcaaagacc  agtcactttt  gcaagaaatg
2221  aaacagctca  tttccatggt  tagccaccg   actttgcttc  aacaagaggt  acataactaa
2281  gccaactctt  cacttggagt  ctgagttata  tatcttctaa  ttcttaggat  aagaaacaga
2341  aatgaaactc  agttatatag  tctgaggatt  accttctgaa  gctgactctt  ttttaaggct
2401  gaactccaga  atccattaga  tgagaaatat  gtagtaaagt  cagctaagtt  aaatcgtttt
2461  cctttggtgg  gttacaggtt  ttgcatctac  gacgccaact  tgagatgcta  aaacgatgcc
2521  aggagaataa  agaagacgaa  gaactctctg  ctcctgccta  a
```

FIG. 17B

MSMASLYRRSLSPPAIDFASFEGKQIFNEALQKGTMEGFFGLISYFQTQSEPAFCGLASLSMVLNSLSIDPGRKWKG
PWRWFDESMLECCEPLEIVKDKGISFGKVVCLAHSSGAKVEAFRTNQSTIDDFRKYVVKCSTSDNCHMISTYHRQVL
KQTGTGHFSPIGGYNAERDMALILDVARFKYPPHWVPLKLLWDAMDSIDQSTGRRRGFMLISRPHREPGLLYTLSCK
DESWISIAKYLKEDVPRLVSSQHVDTIERILYVVFKSLPANFNQFIKWMAEIRRTEDVNQNLSSEEKSRLKLKQELL
KQVQETKLFKHVDKFLSSVYEDNLPYVAAKVYCDGDEILSGYESDESCCKETCVKCIKGLGEEKVTVVAYPSGNDVF
TALLLALPPQTWSGIKDQSLLQEMKQLISMVSHPTLLQQEVLHLRRQLEMLKRCQENKEDEELSAPA

CAGGAGGCATGTCAAGAGCCTCCATCCCCTTAGGAGGACGCTGCTGCCGACAATCTGCTCACTTGGTTAGGAG
ATAAGCCCTTGGAGAGTCCCACGAGCATATCGAGGCAAAATATATGATTCAATAAACAGACTTACT
TCGTGAGGTAGGAGGACATACTAAGGATCAAAGTAATAGGATTTGAGAGAGTATTGGAGCCAAGATAGC
TGGTAACATCCTGGTTACCGGTCTCTTTTGGTTCACTATATATGTAAATTCTTTTGCGTTTATATTATTT
TCTTCGACTATGTAAAAAAAAAAAAAAAAAAAAA

FIG. 18B

MEVASLYRRVLPSPPAVEFASAEGKRLFAEALQGGTMEGFFNLISYFQTQSEPAFCGLASLSVVLNALAI
DPGRPWKGPWRWFDESMLDCCEPLHKVKAEGITFGKVVCLAHCAGARVQSFRADQTTIHDFRAHLTRCAS
SQDCHLISSYHRSPFKQTGTGHFSPIGGYHAEKDMALILDVARFKYPPHWVPLTLLWDAMNTTDEATGLL
RGFMLVSRRSSAPSLLYTVSCGHGSWKSMAKYCVEDVPNLLKDESLDNVTTLLSRLVESLPANAGDLIKC
VIEVRRKEEGESSLSKEKERLFLKEKVLQQIRDTDLFRVVHELQYPKGLCGSCSSSSDEDSLAEIAATV
CCQGAAFLSGNLVSRDGFCCRETCIKCIEANGDGLKTVISGTVVSKGNEQAVDLLPTSSSKTSLCNSNL
KSKIVKYPSSTDVLTVLLLVLQPNTWLGIKDENVKAEFQSLVSTDNLPDLLKQEILHLRRQLHYLAGCKG
QEACQEPPSP

FIG. 18C

```
atgaacattgtaaacgagcatcccagaattctgagaggaagaccaatgcaccaaatat
ggtttgattaaaaacaaggtagtaagcttttgaagctgtccggacaactcaaaaatctttt
tacaaagacaattgcctaaacaatgttttagcttttgattcatctctcgtaaagatgtt
ttttacgagcattgcaagagggacggagctttttgtgaaattattttcgcttgcacagatg
gtaacccaaaacgaaccagccagctttttgtggaactctcgcatgattcttaattcg
cttaaagttgacccgggtagattatggaagggatcttggcgctggtatgatcagtatatg
cttgattgttgtcgatcgctaagcgatattgaaaagatggtgttacgctagaagagttc
tcttgtttagctactggccttcgactattacgaaatgtgtcaaagatgttagc
tttgatgaatttcggaaagacgtaatctcttgttctacccattgagaataaattatggca
atttcattttgccggaaagtgctcggtcaaacaggcgatgacatttagtccagttgga
ggcttcagtgggatttgaaagtgataacaagatattaattggacgttgctcgatttaaatatcct
tgctactgggatttgaagctcatgtacgagagtagtccaatggaccgttgctcgataaagctagc
ggccaacctagagaggctatgtacttttagagcaatgcatattccttaggtgtgcttaca
gtcggtttaaaacaagtacagctccaacagttcattattttccaagcatattatcattttg
acgcagtaaaaaacgcagaaacgctcaaacatatcatctattttgctgaaatactgcagacgcca
cctctaatccagaagcacaaaacgctccaacagttcattattttcccttattgaaagaa
tgtattagaagcacaaacgctttgggcttatattttgctatcttctccatgatcaaaagcttcc
tatatcactatggctttctagaagagatcaattggaaaaaacagcttagttgattagt
aaggcgttctagaagagtcgttgaaaaacagcttgataggttaaccatgatgaattaac
actcaactaactgcgttaacagcttaccattgttgtaaaactgac
actgggtgttgtagttcaagtctgctgtaaaatacgtga
```

FIG. 19A

MNIVKRAVPELLRGMTNATPNIGLIKNKVVSFEAVGQLKKSFYKRQLPKQCLAFDSSLGKDVFLRALQEGR
MENYFSLAQQMVTQNEPAFCGLGTLCMILNSLKVDPGRLWKGSWRWYDQYMLDCCRSLSDIEKDGVTLE
EFSCLANCNGLRTITKCVKDVSFDEFRKDVISCSTIENKIMAISFCRKVLGQTGDGHFSPVGGFSESDNKILIL
DVARFKYPCYWVDLKLMYESMFPIDKASGQPRGYVLLEPMHIPLGVLTVGLNKYSWRNVSKHILQQAAT
VKNADNLAEILLSINQSSIPLIQERSNSSKSGDFEHFKECIRSTKTYHLFLKHTNTNVEYITMAFWAIFSLPMI
QKALPKGVLEEIQSLLKEVEISEINTQLTALKKQLDSLTHCCKTDTGCCSSSCCKNT

FIG. 19B

```
CTACTCACTCATTCATTCATAGTCTCTGCCGAAAATTCATTTTATATTTTCCGCAAG
ATTTCCTATTCGATCACTTCGTTCTGAATATCCTTTTCGAATGGCCACGCTATGAGAAG
AGCAGCAACCGCCGAACTAGAGAACACTTCGGCAAATCGGGTTCTTCGTATTTCCGAACA
AATCATCTTGCAAGCCTCATTCTGATCGGTTGAGCATTCTGTACACGAGTTTTTTGATC
TGCCGTCGAAAGTTTTCTGAGTGCAGCACATTGCCGTGGGAGCAAAACATTGCCGAACTT
TCGACAGCACAATTGGAATTCTTTCGTCTTCTAATGGATCACATAATAAGAATTG
ATTCCACGAGATCACTGACGTGGCAAAATCGAATCATTGATGTTCACATAGGCTTTCAA
TCCATACATTATCAGAGGCCCTCGTTCCTTTTAGTTCGAGCTCCACGAGCCCACGTGG
TAGTTTGTGTAACATCAACGGAGCACAATGCCTTCTGAAGAGTCTCCAATTCACCCA
ATGAGGTGGATACTTGAATCTTGCAACGTCCATAATCAGAACTTGATCAGAATCCTCGTG
ATAGGCGCAAGTGGTGAAAAGTGACCTGATCCCGTTTGACCAAGCACACTCCGATCGTA
GCTGGCTACCAGAACTTGATCATCACTTCGAACTGAATTCACGAGCGATGTCCGAATTT
TTTGAGAAAATCTGGAAAAAAATATTTGTATACTGTAGCTTACCCACTTTAAAGAGGAGATGTGGAAT
TACCTGGAGAATGTGTCACCGTAGATTGATTCCACTTCTAGAAATAATTACTTCAGAAATTTCACTGATTTTCA
AGGAGAATTGTTGTAGATTGATTCCACTTCTAGAAATAATTACTTCAGAAATTTCACTGATTTTCA
TTAAGATTTTACCCAGATGCAAAACATAGAATTTCAACAGGAAACTAAACTTAAAGTTTTGAGAC
TAGTTTTTGCTAGAAATTCAATGAGATTTCGAGATTACAGTAAATTCGTAATAATGTCATTTACAAACTT
AATGAAATTCCTAATCAATGAGATTTCGAGATTACAGTAAATTCGTAATAATGTCATTTACAAACTT
CGGGTACCGTATTTTGGCAAAATCGCAAAATTCCAGCATCGACTCGTGATAGAATCTCCACGG
TCTAATATTTCCAAAGGCACACAACAATCCAGCATCGACTCGTGATAGAATCTCCACGG
CGCTTTCCAAACTTTTTCAGGATCCACTTCCAACGCATTCAGAACCATCAGAAAACTG
CTAGACTTTGGAAAACTTCAAAACTTCAAATTCAAAAAATTATTATTTTATTTACCTAATGTGCTCA
AACCACAATATGCTGGCTCATCTTGTCTGTCCGAAATTGAGATGCCAACTTGAAATAAATAT
TCGCTGATCCTCGAACCAATGCCTCGGTGAAAAGTTTCTTGCCAAGCTCACTGAAAACT
CAATACACGTCTCTCTGGAAGCGGCCTCCGGTAGAAATTTTTGCGGTTACCGACAT
```

FIG. 20A

MSVTAKNFYRRPLPETCIEFSSELGKKLFTEALVRGSANIYFKLASQFRTQDEPAYCGLS
TLVMVLNALEVDPEKVWKAPWRFYHESMLDCCVPLENIRKSGINLQQFSCLAKCNRLKST
VSYGDNSPDFLKKFRTSLVNSVRSDDQVLVASYDRSVLGQTGSGHFSPLAAYHEDSDQVL
IMDVARFKYPPHWVKLETLQKALCSVDVTTKLPRGLVELELKKGTRPLIMYGLKAYVNIN
DSDFATSVISWNQFLLCDPLEDDEEFQLCCRKFGQCFAPHAMCCTQKTFDADQKNSCTE
CSTDQNEACKMICSEIRRTRFAEVFSSSAVAALLIAWPFEKGYSERSDRIGNLAEKYKNE
FSAETMNEMSE

FIG. 20B

SEQUENCE LISTING

<160> NUMBER OF SEQ ID NOS: 10

<210> SEQ ID NO 1
<211> LENGTH: 1748
<212> TYPE: DNA
<213> ORGANISM: Arabidopsis thaliana

<400> SEQUENCE: 1

```
agtaatttag gttattttcg aatccactaa cgaatcttcc acagcaaaca cttttgtgtt      60
cctctgtaat ttctcagtat atatagatac caaaacaagc agtgaaaaat ggctatggcg     120
agtttatatc ggcgatctct tccttctcct ccggccattg acttttcttc cgccgaaggc     180
aagctaatct tcaatgaagc gcttcaaaaa ggaactatgg aaggattttt caggttgatt     240
tcgtattttc agacacaatc cgaacctgcg tattgtggtt tggctagtct ctcagtggtg     300
ttgaatgctc tttctatcga tcctggacgt aaatggaaag ggccttggag gtggtttgat     360
gaatcaatgt tggattgctg cgaacctctg gaagtagtga aggaaaaagg catttcattt     420
ggaaaagttg tctgtttggc tcattgttca ggagcaaaag ttgaggcttt ccgtacaagt     480
cagagcacca ttgatgattt ccgcaaattt gtcgtcaaat gcacgagttc tgagaattgt     540
catatgatct caacatatca ccgaagtgta tttaagcaga ctgggaatgg tcacttttca     600
cctattggtg gctataatgc tgagagagat atggctttga ttcttgatgt tgctcgtttc     660
aagtatcccc ctcactgggt tcctcttaaa cttctttggg aagccatgga cagtattgat     720
cagtcaacag ggaaacgtag agggttcatg ctcatatcta gaccacacag agaacccgga     780
ttgctctata ctctgagctg caaggatgaa agctggatcg aaatagccaa gtatttgaag     840
gaagatgttc ctcgtcttgt aagttcacag catgtagatt ctgtggagaa aatcatatca     900
gttgtgttca agtcacttcc atcaaatttc aaccaattca tcagatgggt ggctgagatc     960
```

-continued

```
cgaattacag aggactcaaa ccaaaatctc agcgcagagg agaagtctag gctgaaacta    1020
aagcaattgg tgctgaagga agtgcacgaa actgaactgt tcaaacacat caataagttc    1080
ttatccacag tgggttatga agacagtctg acttatgctg ctgcaaaggc ttgttgccaa    1140
ggagctgaaa tcttatccgg aagcccatca aaagagtttt gttgtcggga aacttgcgtg    1200
aaatgcatca aggtcctga tgactctgaa ggcacggtgg tgactggagt tgtggtgcgt     1260
gatgggaatg aacaaaaggt tgatctgtta gtgccatcga cgcaaactga gtgtgaatgt    1320
ggtcctgaag caacttatcc agcaggaaac gatgtgttca ctgcacttct attggcttta    1380
cctccacaga catggtcagg gatcaaagac caagctctta tgcatgaaat gaagcagctc    1440
atttccatgg cttccctccc aactttgctt caagaagagg tattgcatct tcgacggcaa    1500
cttcagctgc taaaacgatg ccaagagaac aaggaagagg atgatctcgc tgctcctgcc    1560
tattagttca ttgtcccaaa tcctctctct tccccatttg aatcccacgt tctctacact    1620
taattgttag aaagtctctt tattctctgt acgattcaaa ctctatttgc aatgagagat    1680
atatgtaact tgcattctat aaattgttaa tcacaataag ttaagaatcc aaaaaaaaaa    1740
aaactaaa                                                             1748
```

<210> SEQ ID NO 2
<211> LENGTH: 486
<212> TYPE: PRT
<213> ORGANISM: Arabidopsis thaliana

<400> SEQUENCE: 2

```
Met Ala Met Ala Ser Leu Tyr Arg Arg Ser Leu Pro Ser Pro Pro Ala
  1               5                  10                  15

Ile Asp Phe Ser Ser Ala Glu Gly Lys Leu Ile Phe Asn Glu Ala Leu
             20                  25                  30

Gln Lys Gly Thr Met Glu Gly Phe Phe Arg Leu Ile Ser Tyr Phe Gln
         35                  40                  45

Thr Gln Ser Glu Pro Ala Tyr Cys Gly Leu Ala Ser Leu Ser Val Val
     50                  55                  60

Leu Asn Ala Leu Ser Ile Asp Pro Gly Arg Lys Trp Lys Gly Pro Trp
 65                  70                  75                  80

Arg Trp Phe Asp Glu Ser Met Leu Asp Cys Cys Glu Pro Leu Glu Val
                 85                  90                  95

Val Lys Glu Lys Gly Ile Ser Phe Gly Lys Val Cys Leu Ala His
            100                 105                 110

Cys Ser Gly Ala Lys Val Glu Ala Phe Arg Thr Ser Gln Ser Thr Ile
        115                 120                 125

Asp Asp Phe Arg Lys Phe Val Val Lys Cys Thr Ser Ser Glu Asn Cys
    130                 135                 140

His Met Ile Ser Thr Tyr His Arg Ser Val Phe Lys Gln Thr Gly Asn
145                 150                 155                 160

Gly His Phe Ser Pro Ile Gly Gly Tyr Asn Ala Glu Arg Asp Met Ala
                165                 170                 175

Leu Ile Leu Asp Val Ala Arg Phe Lys Tyr Pro Pro His Trp Val Pro
            180                 185                 190

Leu Lys Leu Leu Trp Glu Ala Met Asp Ser Ile Asp Gln Ser Thr Gly
        195                 200                 205

Lys Arg Arg Gly Phe Met Leu Ile Ser Arg Pro His Arg Glu Pro Gly
    210                 215                 220
```

```
Leu Leu Tyr Thr Leu Ser Cys Lys Asp Glu Ser Trp Ile Glu Ile Ala
225                 230                 235                 240

Lys Tyr Leu Lys Glu Asp Val Pro Arg Leu Val Ser Ser Gln His Val
            245                 250                 255

Asp Ser Val Glu Lys Ile Ile Ser Val Val Phe Lys Ser Leu Pro Ser
        260                 265                 270

Asn Phe Asn Gln Phe Ile Arg Trp Val Ala Glu Ile Arg Ile Thr Glu
    275                 280                 285

Asp Ser Asn Gln Asn Leu Ser Ala Glu Glu Lys Ser Arg Leu Lys Leu
290                 295                 300

Lys Gln Leu Val Leu Lys Glu Val His Glu Thr Glu Leu Phe Lys His
305                 310                 315                 320

Ile Asn Lys Phe Leu Ser Thr Val Gly Tyr Glu Asp Ser Leu Thr Tyr
                325                 330                 335

Ala Ala Ala Lys Ala Cys Cys Gln Gly Ala Glu Ile Leu Ser Gly Ser
            340                 345                 350

Pro Ser Lys Glu Phe Cys Cys Arg Glu Thr Cys Val Lys Cys Ile Lys
        355                 360                 365

Gly Pro Asp Asp Ser Glu Gly Thr Val Val Thr Gly Val Val Val Arg
370                 375                 380

Asp Gly Asn Glu Gln Lys Val Asp Leu Leu Val Pro Ser Thr Gln Thr
385                 390                 395                 400

Glu Cys Glu Cys Gly Pro Glu Ala Thr Tyr Pro Ala Gly Asn Asp Val
                405                 410                 415

Phe Thr Ala Leu Leu Leu Ala Leu Pro Pro Gln Thr Trp Ser Gly Ile
            420                 425                 430

Lys Asp Gln Ala Leu Met His Glu Met Lys Gln Leu Ile Ser Met Ala
        435                 440                 445

Ser Leu Pro Thr Leu Leu Gln Glu Glu Val Leu His Leu Arg Arg Gln
    450                 455                 460

Leu Gln Leu Leu Lys Arg Cys Gln Glu Asn Lys Glu Glu Asp Asp Leu
465                 470                 475                 480

Ala Ala Pro Ala Tyr Glx
                485
```

<210> SEQ ID NO 3
<211> LENGTH: 2561
<212> TYPE: DNA
<213> ORGANISM: Arabidopsis thaliana

<400> SEQUENCE: 3

| | | | | | |
|---|---|---|---|---|---|
| atgtctatgg | cgagtttgta | tcggcggtct | ctttcccctc | cggcgataga | tttcgcttct | 60 |
| tttgaaggaa | aggtgcgtta | tttctcaagt | gttcgatcca | tggattcaat | gaaaattca | 120 |
| gggttctggg | ttttaacttt | ttaagtatcc | ttgtgcttct | ggttagagat | gatcactgat | 180 |
| ttggttttg | tatgttgatt | gatttggtta | cttctctatc | tgtatagagt | ctagaaattg | 240 |
| gattttcttg | gaactgtgt | aaaactcgta | aaacccctaaa | cccttgctg | tttttacaag | 300 |
| tttagttgtt | ggtgagagat | ctgagcatgc | ttcatgataa | atggttcacg | aattattgat | 360 |
| agccaattta | gtagaatggg | acaagttctt | ttgccctgag | aatttaaatg | ttgtcattgt | 420 |
| ctttgcagca | aatcttcaat | gaagcgcttc | agaaaggcac | tatggaagga | ttttcgggc | 480 |
| tgatttctta | ttttcagaca | cagtctgagc | cagcttttg | tggcttagct | agtctttcga | 540 |
| tggttttgaa | ttctctttct | attgacccgg | gaagaaagtg | gaaaggtata | catacctcta | 600 |

-continued

| | |
|---|---|
| ctggagagta catttgttgg tgggttttig aattttttig gtttctctca gggccttgga | 660 |
| ggtggtttga tgaatcaatg ctggaatgtt gcgagccgct tgaaatagtg aaggataaag | 720 |
| gcatttcatt tggaaaagtg gtctgtttag ctcattcttc aggagcaaaa gtcgaagctt | 780 |
| tccgcacaaa tcagagcacc attgatgatt ccgcaaaata tgtggtcaaa tgttcaactt | 840 |
| ctgataattg tcatatgatc tcaacatatc ataggcaagt actcaagcag gtatcatttt | 900 |
| tttggcctaa actctgtgta tattaacagt tatatggcaa ttaagtgaaa ttcattagac | 960 |
| ttaatgttat tacaaagttt gataatggtg aaactctttc atgtcttgct atgaagtccc | 1020 |
| atgctgatcg gattctaatg tctatgattg cagactggaa ctggccactt tcacctatt | 1080 |
| ggtggttata atgctgaaag agatatggct ttgattcttg atgtcgctcg tttcaagtat | 1140 |
| cctcctcact gggttcctct taaacttctt tgggatgcca tggatagtat tgatcagtca | 1200 |
| acagggagac gtagagggta catggatctc tattcttttt cttaggcttc acttgtatga | 1260 |
| ttaaagaatg taatccgttt cttttttgcta ttctgcttta cttccaggtt catgcttata | 1320 |
| tcaagacccc acagagaacc aggattgctc tatacattag taagtccaaa gtcatggttc | 1380 |
| tattagtagt tgctgctatt acaataacat ttctttcgaa taggactgag taatgatatc | 1440 |
| ttgattatcg atttcagagt tgtaaggatg agagctggat cagcattgca aagtatttga | 1500 |
| aggaagatgt tcctcgtctt gtaagctcac aacatgttga tactattgaa agaatcttat | 1560 |
| atgttgtatt caagtcactt ccagcaaatt tcaaccaatt tatcaaatgg atggctgaga | 1620 |
| ttcgaagaac agaggatgta aatcaaaatc ttagctcaga agagaaatca aggctcaaat | 1680 |
| taaaggtatt atcttgtcca tttgcttctg aactttagtt ttccatgttt atattccatc | 1740 |
| agtttattca tcactgttct atggttcgtt ttgctgtagc aagagttact gaaacaagtg | 1800 |
| caagaaacta aactgttcaa gcatgtggat aagtttctct cctctgtgta cgaagacaat | 1860 |
| ctgccatatg ttgctgctaa ggtttattgt gacggagatg aaatcttatc gggatatgaa | 1920 |
| tcagatgaat cctgttgtaa ggaaacttgt gtcaaatgta tcaaaggtat gtttgttctt | 1980 |
| acattctggt tatcttttcta agcgcttcag aaaccttggc ttgaagttag tagtgtgcaa | 2040 |
| agttctaatc aagaaatcac ttttttcttt gaatttcttg ttttacatca aggtcttggt | 2100 |
| gaggagaaag tgacagtggt agcttaccca tccgggaacg atgtgttcac tgctcttctg | 2160 |
| ttggctttac ctccacagac gtggtcaggt atcaaagacc agtcactttt gcaagaaatg | 2220 |
| aaacagctca tttccatggt tagccacccg actttgcttc aacaagaggt acataactaa | 2280 |
| gccaactctt cacttggagt ctgagttata tatcttctaa ttcttaggat aagaaacaga | 2340 |
| aatgaaactc agttatatag tctgaggatt accttctgaa gctgactctt ttttaaggct | 2400 |
| gaactccaga atccattaga tgagaaatat gtagtaaagt cagctaagtt aaatcgtttt | 2460 |
| cctttggtgg gttacaggtt ttgcatctac gacgccaact tgagatgcta aaacgatgcc | 2520 |
| aggagaataa agaagacgaa gaactctctg ctcctgccta a | 2561 |

<210> SEQ ID NO 4
<211> LENGTH: 452
<212> TYPE: PRT
<213> ORGANISM: Arabidopsis thaliana

<400> SEQUENCE: 4

Met Ser Met Ala Ser Leu Tyr Arg Arg Ser Leu Ser Pro Pro Ala Ile
 1               5                  10                  15

Asp Phe Ala Ser Phe Glu Gly Lys Gln Ile Phe Asn Glu Ala Leu Gln
             20                  25                  30

-continued

```
Lys Gly Thr Met Glu Gly Phe Phe Gly Leu Ile Ser Tyr Phe Gln Thr
        35                  40                  45
Gln Ser Glu Pro Ala Phe Cys Gly Leu Ala Ser Leu Ser Met Val Leu
    50                  55                  60
Asn Ser Leu Ser Ile Asp Pro Gly Arg Lys Trp Lys Gly Pro Trp Arg
65                  70                  75                  80
Trp Phe Asp Glu Ser Met Leu Glu Cys Cys Glu Pro Leu Glu Ile Val
                85                  90                  95
Lys Asp Lys Gly Ile Ser Phe Gly Lys Val Val Cys Leu Ala His Ser
            100                 105                 110
Ser Gly Ala Lys Val Glu Ala Phe Arg Thr Asn Gln Ser Thr Ile Asp
        115                 120                 125
Asp Phe Arg Lys Tyr Val Val Lys Cys Ser Thr Ser Asp Asn Cys His
    130                 135                 140
Met Ile Ser Thr Tyr His Arg Gln Val Leu Lys Gln Thr Gly Thr Gly
145                 150                 155                 160
His Phe Ser Pro Ile Gly Gly Tyr Asn Ala Glu Arg Asp Met Ala Leu
                165                 170                 175
Ile Leu Asp Val Ala Arg Phe Lys Tyr Pro Pro His Trp Val Pro Leu
            180                 185                 190
Lys Leu Leu Trp Asp Ala Met Asp Ser Ile Asp Gln Ser Thr Gly Arg
        195                 200                 205
Arg Arg Gly Phe Met Leu Ile Ser Arg Pro His Arg Glu Pro Gly Leu
    210                 215                 220
Leu Tyr Thr Leu Ser Cys Lys Asp Glu Ser Trp Ile Ser Ile Ala Lys
225                 230                 235                 240
Tyr Leu Lys Glu Asp Val Pro Arg Leu Val Ser Ser Gln His Val Asp
                245                 250                 255
Thr Ile Glu Arg Ile Leu Tyr Val Val Phe Lys Ser Leu Pro Ala Asn
            260                 265                 270
Phe Asn Gln Phe Ile Lys Trp Met Ala Glu Ile Arg Arg Thr Glu Asp
        275                 280                 285
Val Asn Gln Asn Leu Ser Ser Glu Glu Lys Ser Arg Leu Lys Leu Lys
    290                 295                 300
Gln Glu Leu Leu Lys Gln Val Gln Glu Thr Lys Leu Phe Lys His Val
305                 310                 315                 320
Asp Lys Phe Leu Ser Ser Val Tyr Glu Asp Asn Leu Pro Tyr Val Ala
                325                 330                 335
Ala Lys Val Tyr Cys Asp Gly Asp Glu Ile Leu Ser Gly Tyr Glu Ser
            340                 345                 350
Asp Glu Ser Cys Cys Lys Glu Thr Cys Val Lys Cys Ile Lys Gly Leu
        355                 360                 365
Gly Glu Glu Lys Val Thr Val Val Ala Tyr Pro Ser Gly Asn Asp Val
    370                 375                 380
Phe Thr Ala Leu Leu Ala Leu Pro Pro Gln Thr Trp Ser Gly Ile
385                 390                 395                 400
Lys Asp Gln Ser Leu Leu Gln Glu Met Lys Gln Leu Ile Ser Met Val
                405                 410                 415
Ser His Pro Thr Leu Leu Gln Gln Glu Val Leu His Leu Arg Arg Gln
            420                 425                 430
Leu Glu Met Leu Lys Arg Cys Gln Glu Asn Lys Glu Asp Glu Glu Leu
        435                 440                 445
```

Ser Ala Pro Ala
   450

<210> SEQ ID NO 5
<211> LENGTH: 2006
<212> TYPE: DNA
<213> ORGANISM: Triticum aestivum

<400> SEQUENCE: 5

| | | | | | |
|---|---|---|---|---|---|
| aatttaagca | tcgaaaagcg | gaagtggagg | agcacaactg | gcggtcgaca | gcgaggcgcc | 60 |
| gacgacgact | cccaggttga | aatcctattg | aatttcaggg | acgggggaga | ggaataaaaa | 120 |
| cgaggagagt | cgacactcga | cagacaggtg | gcgagatccc | ccgaagccgt | ccgtactctc | 180 |
| gcagcagatc | ggccggcgga | agccagcagg | atggaggtgg | cgtcgctgta | ccggcgggtg | 240 |
| ctgccgtcgc | cgccggcggt | ggagttcgcg | tcggcggagg | ggaagcggct | gttcgcggag | 300 |
| gcgctgcagg | gcgggaccat | ggagggcttc | ttcaacctca | tctcctactt | ccagacgcag | 360 |
| tcggagccgg | ccttctgcgg | cctcgcctcc | ctctccgtcg | tgctcaacgc | gctcgccatc | 420 |
| gaccccggcc | ggccgtggaa | ggggccctgg | cgctggttcg | acgagtccat | gctcgactgc | 480 |
| tgcgagcccc | tccacaaggt | caaggccgag | ggcatcacct | tcggcaaggt | cgtctgcctc | 540 |
| gcgcactgcg | ccggcgcccg | tgtccagtcc | ttccgcgccg | accagaccac | catccacgac | 600 |
| ttccgcgccc | acctcacgcg | ctgcgcctcc | tcccaggact | gccatctcat | ctcctcctac | 660 |
| cacaggagcc | ccttcaagca | gactgggact | ggccatttct | caccgatcgg | cgggtatcat | 720 |
| gccgagaaag | acatggcgct | catcttggat | gttgcgcgct | caaataccc | tcctcattgg | 780 |
| gttccattga | cgcttctctg | ggatgccatg | aacacgactg | atgaagcaac | tgggcttctc | 840 |
| aggggggttca | tgcttgtatc | aaggcgcagt | tcagctcctt | cattgctcta | cacagtgagt | 900 |
| tgcggccatg | gaagttggaa | aagcatggca | agtattgtg | tggaagatgt | gcccaatcta | 960 |
| ctgaaggatg | agagtctaga | caatgttaca | acacttctgt | cccgcctagt | ggaatctctc | 1020 |
| ccagccaatg | ctggagattt | gatcaaatgt | gtcattgaag | ttaggagaaa | agaggaaggt | 1080 |
| gaatcaagct | tgagtaaaga | ggagaaagaa | aggcttttt | tgaaggaaaa | agtattacag | 1140 |
| caaatccgtg | atactgatct | tttcagagta | gtccacgaac | tgcaatatcc | caaggggcta | 1200 |
| tgtggtagtt | gctcgtcttc | aagtgatgaa | gattcgcttg | ccgagattgc | agccactgtg | 1260 |
| tgctgtcaag | gagctgcatt | cctatctggt | aaccttgtat | ctagagatgg | gttctgctgc | 1320 |
| cgagaaacat | gtatcaaatg | tatagaagca | aatggtgatg | gactaaagac | tgttatctca | 1380 |
| ggaaccgtgg | tatctaaagg | gaatgaacag | gctgttgatt | tgcttttacc | aacatcctcg | 1440 |
| tcaaaaacaa | gcttatgcaa | ttcaaacttg | aagagcaaga | ttgtcaagta | tccatcaagc | 1500 |
| acagatgttc | taactgtcct | actgctggtt | ttacagccta | acacatggct | tggcataaaa | 1560 |
| gacgagaacg | tgaaagctga | atttcagagt | cttgtttcaa | cagacaatct | tcctgatctt | 1620 |
| cttaaacagg | agatactgca | tctaaggcgg | cagctccatt | atttggctgg | ttgtaaagga | 1680 |
| caggaggcat | gtcaagagcc | tccatcccct | tagggacgct | gctgcgacaa | tctgctcact | 1740 |
| tggttaggag | ataaggcccct | tggagatccc | acgagcatac | tatcgaggca | aaaatatatg | 1800 |
| attcaataaa | cagacttact | tcgtgaggta | ggaggacata | ctaaggatca | aagtaatagg | 1860 |
| attttgagag | agtattggag | ccaagatagc | tggtaacatc | ctggttaccg | gtctcttttg | 1920 |
| gttcactata | tatgtaaatt | cttttgcgtt | tatattattt | tcttcgacta | tgtaaaaaaa | 1980 |
| aaaaaaaaaa | aaaaaaaaaa | aaaaaa | | | | 2006 |

```
<210> SEQ ID NO 6
<211> LENGTH: 500
<212> TYPE: PRT
<213> ORGANISM: Triticum aestivum

<400> SEQUENCE: 6

Met Glu Val Ala Ser Leu Tyr Arg Arg Val Leu Pro Ser Pro Pro Ala
 1               5                  10                  15

Val Glu Phe Ala Ser Ala Glu Gly Lys Arg Leu Phe Ala Glu Ala Leu
            20                  25                  30

Gln Gly Gly Thr Met Glu Gly Phe Phe Asn Leu Ile Ser Tyr Phe Gln
        35                  40                  45

Thr Gln Ser Glu Pro Ala Phe Cys Gly Leu Ala Ser Leu Ser Val Val
    50                  55                  60

Leu Asn Ala Leu Ala Ile Asp Pro Gly Arg Pro Trp Lys Gly Pro Trp
65                  70                  75                  80

Arg Trp Phe Asp Glu Ser Met Leu Asp Cys Cys Glu Pro Leu His Lys
                85                  90                  95

Val Lys Ala Glu Gly Ile Thr Phe Gly Lys Val Val Cys Leu Ala His
            100                 105                 110

Cys Ala Gly Ala Arg Val Gln Ser Phe Arg Ala Asp Gln Thr Thr Ile
        115                 120                 125

His Asp Phe Arg Ala His Leu Thr Arg Cys Ala Ser Ser Gln Asp Cys
    130                 135                 140

His Leu Ile Ser Ser Tyr His Arg Ser Pro Phe Lys Gln Thr Gly Thr
145                 150                 155                 160

Gly His Phe Ser Pro Ile Gly Gly Tyr His Ala Glu Lys Asp Met Ala
                165                 170                 175

Leu Ile Leu Asp Val Ala Arg Phe Lys Tyr Pro Pro His Trp Val Pro
            180                 185                 190

Leu Thr Leu Leu Trp Asp Ala Met Asn Thr Thr Asp Glu Ala Thr Gly
        195                 200                 205

Leu Leu Arg Gly Phe Met Leu Val Ser Arg Arg Ser Ser Ala Pro Ser
    210                 215                 220

Leu Leu Tyr Thr Val Ser Cys Gly His Gly Ser Trp Lys Ser Met Ala
225                 230                 235                 240

Lys Tyr Cys Val Glu Asp Val Pro Asn Leu Leu Lys Asp Glu Ser Leu
                245                 250                 255

Asp Asn Val Thr Thr Leu Leu Ser Arg Leu Val Glu Ser Leu Pro Ala
            260                 265                 270

Asn Ala Gly Asp Leu Ile Lys Cys Val Ile Glu Val Arg Arg Lys Glu
        275                 280                 285

Glu Gly Glu Ser Ser Leu Ser Lys Glu Lys Glu Arg Leu Phe Leu
    290                 295                 300

Lys Glu Lys Val Leu Gln Gln Ile Arg Asp Thr Asp Leu Phe Arg Val
305                 310                 315                 320

Val His Glu Leu Gln Tyr Pro Lys Gly Leu Cys Gly Ser Cys Ser Ser
                325                 330                 335

Ser Ser Asp Glu Asp Ser Leu Ala Glu Ile Ala Ala Thr Val Cys Cys
            340                 345                 350

Gln Gly Ala Ala Phe Leu Ser Gly Asn Leu Val Ser Arg Asp Gly Phe
        355                 360                 365

Cys Cys Arg Glu Thr Cys Ile Lys Cys Ile Glu Ala Asn Gly Asp Gly
    370                 375                 380
```

```
Leu Lys Thr Val Ile Ser Gly Thr Val Ser Lys Gly Asn Glu Gln
385                 390                 395                 400

Ala Val Asp Leu Leu Pro Thr Ser Ser Lys Thr Ser Leu Cys
            405                 410                 415

Asn Ser Asn Leu Lys Ser Lys Ile Val Lys Tyr Pro Ser Ser Thr Asp
                420                 425                 430

Val Leu Thr Val Leu Leu Val Leu Gln Pro Asn Thr Trp Leu Gly
            435                 440                 445

Ile Lys Asp Glu Asn Val Lys Ala Glu Phe Gln Ser Leu Val Ser Thr
    450                 455                 460

Asp Asn Leu Pro Asp Leu Leu Lys Gln Glu Ile Leu His Leu Arg Arg
465                 470                 475                 480

Gln Leu His Tyr Leu Ala Gly Cys Lys Gly Gln Glu Ala Cys Gln Glu
                485                 490                 495

Pro Pro Ser Pro
            500

<210> SEQ ID NO 7
<211> LENGTH: 1245
<212> TYPE: DNA
<213> ORGANISM: Schizosaccharomyces pombe

<400> SEQUENCE: 7
atgaacattg ttaaacgagc agtcccagaa ttactgagag gaatgaccaa tgcaacacca      60
aatatcggtt tgattaaaaa caaggtagta agctttgaag ctgtcggaca actcaaaaaa     120
tcttttttaca aaagacaatt gcctaaacaa tgtttagctt ttgattcatc tctcggtaaa    180
gatgtttttt tacgagcatt gcaagaggga cggatggaaa attattttttc gcttgcacag   240
cagatggtaa cccaaaacga accagctttt tgtggattgg gaactctctg catgattctt    300
aattcgctta agttgacccc gggtagatta tggaagggat cttggcgctg gtatgatcag    360
tatatgcttg attgttgtcg atcgctaagc gatattgaaa aagatggtgt acgctagaa     420
gagttctctt gtttagctaa ctgcaatggc cttcggacta ttacgaaatg tgtcaaagat   480
gttagctttg atgaatttcg gaaagacgta atctcttgtt ctaccattga ataaaaatt    540
atggcaattt cattttgccg gaaagtgctc ggtcaaacag gcgatggaca ttttagtcca   600
gttggaggct tcagtgaaag tgataacaag atattaatat tggacgttgc tcgatttaaa   660
tatccttgct actgggtgga tttgaagctc atgtacgaga gtatgtttcc tatcgataaa   720
gctagcggcc aacctagagg ctatgtactt ttagagccaa tgcatattcc tttaggtgtg    780
cttacagtcg gtttaaacaa gtacagctgg cgaaacgttt ccaagcatat actgcagcag   840
gcggcaacgg taaaaaacgc agacaatttg gctgaaatac ttttatccat taatcaatca   900
tcaattcctc taatccaaga acgctccaac agttcaaagt ctggtgattt cgagcatttt   960
aaagaatgta ttagaagcac aaaaacatat catttatttc tgaaacatac gaataccaat    1020
gttgaatata tcactatggc ttttttgggct atatttttcct tacccatgat ccaaaaagcg  1080
cttcccaaag gcgttctaga agagattcaa tctttattga agaagttga aatttccgaa    1140
attaacactc aactaactgc gttgaaaaaa cagcttgata gtttaaccca ttgttgtaaa   1200
actgacactg ggtgttgtag ttcaagctgc tgtaaaaata cgtga                  1245

<210> SEQ ID NO 8
<211> LENGTH: 414
<212> TYPE: PRT
```

<213> ORGANISM: Schizosaccharomyces pombe

<400> SEQUENCE: 8

| | | | | | | | | | | | | | | |
|---|---|---|---|---|---|---|---|---|---|---|---|---|---|---|
| Met | Asn | Ile | Val | Lys | Arg | Ala | Val | Pro | Glu | Leu | Leu | Arg | Gly | Met | Thr |
| 1 | | | | 5 | | | | | 10 | | | | | 15 | |
| Asn | Ala | Thr | Pro | Asn | Ile | Gly | Leu | Ile | Lys | Asn | Lys | Val | Val | Ser | Phe |
| | | | 20 | | | | | 25 | | | | | 30 | | |
| Glu | Ala | Val | Gly | Gln | Leu | Lys | Lys | Ser | Phe | Tyr | Lys | Arg | Gln | Leu | Pro |
| | | | 35 | | | | 40 | | | | | 45 | | | |
| Lys | Gln | Cys | Leu | Ala | Phe | Asp | Ser | Ser | Leu | Gly | Lys | Asp | Val | Phe | Leu |
| | 50 | | | | | 55 | | | | | 60 | | | | |
| Arg | Ala | Leu | Gln | Glu | Gly | Arg | Met | Glu | Asn | Tyr | Phe | Ser | Leu | Ala | Gln |
| 65 | | | | | 70 | | | | | 75 | | | | | 80 |
| Gln | Met | Val | Thr | Gln | Asn | Glu | Pro | Ala | Phe | Cys | Gly | Leu | Gly | Thr | Leu |
| | | | | 85 | | | | | 90 | | | | | 95 | |
| Cys | Met | Ile | Leu | Asn | Ser | Leu | Lys | Val | Asp | Pro | Gly | Arg | Leu | Trp | Lys |
| | | | 100 | | | | | 105 | | | | | 110 | | |
| Gly | Ser | Trp | Arg | Trp | Tyr | Asp | Gln | Tyr | Met | Leu | Asp | Cys | Cys | Arg | Ser |
| | | | 115 | | | | | 120 | | | | | 125 | | |
| Leu | Ser | Asp | Ile | Glu | Lys | Asp | Gly | Val | Thr | Leu | Glu | Glu | Phe | Ser | Cys |
| | 130 | | | | | 135 | | | | | 140 | | | | |
| Leu | Ala | Asn | Cys | Asn | Gly | Leu | Arg | Thr | Ile | Thr | Lys | Cys | Val | Lys | Asp |
| 145 | | | | | 150 | | | | | 155 | | | | | 160 |
| Val | Ser | Phe | Asp | Glu | Phe | Arg | Lys | Asp | Val | Ile | Ser | Cys | Ser | Thr | Ile |
| | | | | 165 | | | | | 170 | | | | | 175 | |
| Glu | Asn | Lys | Ile | Met | Ala | Ile | Ser | Phe | Cys | Arg | Lys | Val | Leu | Gly | Gln |
| | | | 180 | | | | | 185 | | | | | 190 | | |
| Thr | Gly | Asp | Gly | His | Phe | Ser | Pro | Val | Gly | Gly | Phe | Ser | Glu | Ser | Asp |
| | | | 195 | | | | | 200 | | | | | 205 | | |
| Asn | Lys | Ile | Leu | Ile | Leu | Asp | Val | Ala | Arg | Phe | Lys | Tyr | Pro | Cys | Tyr |
| | 210 | | | | | 215 | | | | | 220 | | | | |
| Trp | Val | Asp | Leu | Lys | Leu | Met | Tyr | Glu | Ser | Met | Phe | Pro | Ile | Asp | Lys |
| 225 | | | | | 230 | | | | | 235 | | | | | 240 |
| Ala | Ser | Gly | Gln | Pro | Arg | Gly | Tyr | Val | Leu | Leu | Glu | Pro | Met | His | Ile |
| | | | | 245 | | | | | 250 | | | | | 255 | |
| Pro | Leu | Gly | Val | Leu | Thr | Val | Gly | Leu | Asn | Lys | Tyr | Ser | Trp | Arg | Asn |
| | | | 260 | | | | | 265 | | | | | 270 | | |
| Val | Ser | Lys | His | Ile | Leu | Gln | Gln | Ala | Ala | Thr | Val | Lys | Asn | Ala | Asp |
| | | | 275 | | | | | 280 | | | | | 285 | | |
| Asn | Leu | Ala | Glu | Ile | Leu | Leu | Ser | Ile | Asn | Gln | Ser | Ser | Ile | Pro | Leu |
| | 290 | | | | | 295 | | | | | 300 | | | | |
| Ile | Gln | Glu | Arg | Ser | Asn | Ser | Ser | Lys | Ser | Gly | Asp | Phe | Glu | His | Phe |
| 305 | | | | | 310 | | | | | 315 | | | | | 320 |
| Lys | Glu | Cys | Ile | Arg | Ser | Thr | Lys | Thr | Tyr | His | Leu | Phe | Leu | Lys | His |
| | | | | 325 | | | | | 330 | | | | | 335 | |
| Thr | Asn | Thr | Asn | Val | Glu | Tyr | Ile | Thr | Met | Ala | Phe | Trp | Ala | Ile | Phe |
| | | | 340 | | | | | 345 | | | | | 350 | | |
| Ser | Leu | Pro | Met | Ile | Gln | Lys | Ala | Leu | Pro | Lys | Gly | Val | Leu | Glu | Glu |
| | | | 355 | | | | | 360 | | | | | 365 | | |
| Ile | Gln | Ser | Leu | Leu | Lys | Glu | Val | Glu | Ile | Ser | Glu | Ile | Asn | Thr | Gln |
| | 370 | | | | | 375 | | | | | 380 | | | | |
| Leu | Thr | Ala | Leu | Lys | Lys | Gln | Leu | Asp | Ser | Leu | Thr | His | Cys | Cys | Lys |
| 385 | | | | | 390 | | | | | 395 | | | | | 400 |

Thr Asp Thr Gly Cys Cys Ser Ser Ser Cys Cys Lys Asn Thr
                    405                 410

<210> SEQ ID NO 9
<211> LENGTH: 1495
<212> TYPE: DNA
<213> ORGANISM: Caenorhabditis elegans

<400> SEQUENCE: 9

| | | | | | |
|---|---|---|---|---|---|
| ctactcactc | atttcattca | tagtctctgc | cgaaaattca | tttttatatt | tttccgcaag | 60 |
| atttcctatt | cgatcacttc | gttctgaata | tccttttcg | aatggccacg | ctatgagaag | 120 |
| agcagcaacc | gccgaactag | agaacacttc | ggcaaatcgg | gttcttcgta | tttccgaaca | 180 |
| aatcatcttg | caagcctcat | tctgatcggt | tgagcattct | gtacacgagt | tttttgatc | 240 |
| tgcgtcgaaa | gttttctgag | tgcagcacat | tgcgtgggga | gcaaaacatt | gcccgaactt | 300 |
| tcgacagcac | aattggaatt | cttcttcgtc | gtcttctaat | ggatcacata | taagaattg | 360 |
| attccacgag | atcactgacg | tggcaaaatc | ggaatcattg | atgttcacat | aggctttcaa | 420 |
| tccatacatt | atcagaggcc | tcgttccttt | ttttagttcg | agctccacga | gcccacgtgg | 480 |
| tagttttgtt | gtaacatcaa | cggagcacaa | tgccttctga | agagtctcca | atttcaccca | 540 |
| atgaggtgga | tacttgaatc | ttgcaacgtc | cataatcaga | acttgatcag | aatcctcgtg | 600 |
| ataggcggca | agtggtgaaa | agtgacctga | tcccgtttga | ccaagcacac | tccgatcgta | 660 |
| gctggctacc | agaacttgat | catcacttcg | aactgaattc | acgagcgatg | tccggaattt | 720 |
| tttgagaaaa | tctggaaaaa | aatatttgta | taggacattt | taaagagga | gatgtggaat | 780 |
| tacctggaga | attgtcaccg | tagcttactg | tagattttag | acgattacat | tttgcaaggc | 840 |
| aggagaattg | ttgtagattg | attccacttc | tagaaataat | taatttttt | ttgaacattt | 900 |
| ttaagatttt | acccagatgc | aaaaatttgc | gattacttca | gaaatttcac | tgatttttca | 960 |
| tagttttttg | ctagaaaaca | tagaatttca | acgaaacagg | aaacaaaacg | tcgaaaattt | 1020 |
| aatgaaattt | cctaatcaat | gagatttcga | gattacagta | aactttaaaa | gttttgagac | 1080 |
| cgggtaccgt | attttttggca | aaaatcgcaa | aatttcgtaa | taatgtcatt | ttacaaactt | 1140 |
| tctaatattt | tccaaaggca | cacaacaatc | cagcatcgac | tcgtgataga | atctccacgg | 1200 |
| cgctttccaa | acttttcag | gatccacttc | caacgcattc | agaaccatca | ctgaaaactg | 1260 |
| ctagactttg | gaaaacttca | aaatcaaaaa | attattattt | tattttacct | aatgtgctca | 1320 |
| aaccacaata | tgctggctca | tcttgtgtcc | gaaattgaga | tgccaacttg | aaataaatat | 1380 |
| tcgctgatcc | tcgaaccaat | gcctcggtga | aagtttctt | gccaagctca | ctggaaaact | 1440 |
| caatacacgt | ctctggaagc | ggcctccggt | agaaattttt | tgcggttacc | gacat | 1495 |

<210> SEQ ID NO 10
<211> LENGTH: 371
<212> TYPE: PRT
<213> ORGANISM: Caenorhabditis elegans

<400> SEQUENCE: 10

Met Ser Val Thr Ala Lys Asn Phe Tyr Arg Arg Pro Leu Pro Glu Thr
 1               5                  10                  15

Cys Ile Glu Phe Ser Ser Glu Leu Gly Lys Lys Leu Phe Thr Glu Ala
            20                  25                  30

Leu Val Arg Gly Ser Ala Asn Ile Tyr Phe Lys Leu Ala Ser Gln Phe
        35                  40                  45

Arg Thr Gln Asp Glu Pro Ala Tyr Cys Gly Leu Ser Thr Leu Val Met

-continued

```
                50                      55                      60
Val Leu Asn Ala Leu Glu Val Asp Pro Glu Lys Val Trp Lys Ala Pro
 65                  70                      75                  80

Trp Arg Phe Tyr His Glu Ser Met Leu Asp Cys Cys Val Pro Leu Glu
                     85                      90                  95

Asn Ile Arg Lys Ser Gly Ile Asn Leu Gln Gln Phe Ser Cys Leu Ala
                    100                     105             110

Lys Cys Asn Arg Leu Lys Ser Thr Val Ser Tyr Gly Asp Asn Ser Pro
                115                     120                 125

Asp Phe Leu Lys Lys Phe Arg Thr Ser Leu Val Asn Ser Val Arg Ser
        130                     135                 140

Asp Asp Gln Val Leu Val Ala Ser Tyr Asp Arg Ser Val Leu Gly Gln
145                     150                     155                 160

Thr Gly Ser Gly His Phe Ser Pro Leu Ala Ala Tyr His Glu Asp Ser
                    165                     170                 175

Asp Gln Val Leu Ile Met Asp Val Ala Arg Phe Lys Tyr Pro Pro His
                180                     185                 190

Trp Val Lys Leu Glu Thr Leu Gln Lys Ala Leu Cys Ser Val Asp Val
        195                     200                     205

Thr Thr Lys Leu Pro Arg Gly Leu Val Glu Leu Glu Leu Lys Lys Gly
        210                     215                     220

Thr Arg Pro Leu Ile Met Tyr Gly Leu Lys Ala Tyr Val Asn Ile Asn
225                     230                     235                 240

Asp Ser Asp Phe Ala Thr Ser Val Ile Ser Trp Asn Gln Phe Leu Leu
                    245                     250                 255

Cys Asp Pro Leu Glu Asp Glu Glu Phe Gln Leu Cys Cys Arg
                260                     265                 270

Lys Phe Gly Gln Cys Phe Ala Pro His Ala Met Cys Cys Thr Gln Lys
        275                     280                     285

Thr Phe Asp Ala Asp Gln Lys Asn Ser Cys Thr Glu Cys Ser Thr Asp
        290                     295                     300

Gln Asn Glu Ala Cys Lys Met Ile Cys Ser Glu Ile Arg Arg Thr Arg
305                     310                     315                 320

Phe Ala Glu Val Phe Ser Ser Ser Ala Val Ala Ala Leu Leu Ile Ala
                    325                     330                 335

Trp Pro Phe Glu Lys Gly Tyr Ser Glu Arg Ser Asp Arg Ile Gly Asn
                340                     345                 350

Leu Ala Glu Lys Tyr Lys Asn Glu Phe Ser Ala Glu Thr Met Asn Glu
            355                     360                     365

Met Ser Glu
        370
```

PHYTOCHELATIN SYNTHASES AND USES THEREFOR

CROSS REFERENCE TO RELATED APPLICATIONS

This application is a continuation in part of U.S. application Ser. No. 09/315,449 now abandoned, filed May 20, 1999, and is thereby entitled to priority, pursuant to 35 U.S.C. §119(e), to U.S. Provisional Application No. 60/095, 624, filed on Aug. 7, 1998, both of which are incorporated herein by reference.

STATEMENT REGARDING FEDERALLY SPONSORED RESEARCH OR DEVELOPMENT

This invention was supported in part by finds from the U.S. Government (National Science Foundation Grant No. MCB-9604246, Department of Agriculture NRICGP Grant No. 9337304, Department of Agriculture Grant No. 98-35304-6684, and Department of Energy Grant Nos. DE-FG02-91ER20055, DE-FG02-94ER20162, and DE-FG07-96ER20253) and the U.S. Government may therefore have certain rights in the invention.

BACKGROUND OF THE INVENTION

Essential heavy metals, such as copper and zinc, are required as cofactors in redox reactions and ligand interactions and they also participate in charge stabilization, water ionization, and charge shielding during biocatalysis (Voet and Voet, 1995, In: Biochemistry, 2nd ed., John Wiley & Sons, Inc., New York). In addition to the essential heavy metals, non-essential heavy metals, such as arsenic, cadmium, mercury and lead,.are found in natural mineral deposits or as a result of human activity and they are frequently encountered by living organisms (Nriagu and Pacyna, 1988, Nature 333:134–138). Both essential and non-essential heavy metals can pose an acute problem for all living organisms in that the organisms often encounter supraoptimal concentrations of essential heavy metals and excess micromolar concentrations of non-essential heavy metals such as As, Cd, Hg and Pb. High concentrations of these non-essential heavy metals exert toxic effects through the displacement of endogenous metal cofactors, heavy or otherwise, from their cellular binding sites, aberrant reactions with the thiol groups of proteins and coenzymes, and the promotion of the formation of active oxygen species (AOS; Stadtman, 1990, Free Radic. Biol. Med. 9:315–325).

Massive global expansion in industrial and mining activities during the last two decades combined with changes in agricultural practices, have markedly increased contamination of groundwaters and soils with heavy metals. Indeed, it is estimated that the annual toxicity of metal emissions exceeds that of organics and radionuclides combined (Nriagu and Pacyna, 1988, Nature 333:134–138). Since soil and water contamination results in the uptake of heavy metals and toxins by crop plants, and eventually by humans, there is a pressing need for environmental cleanup to prevent entry of non-essential heavy metals into the food chain.

As sessile photosynthetic organisms, the mechanisms deployed by vascular plants for abrogating or alleviating heavy metal toxicity are of general interest. Not only does their lack of specialized excretory organs subject plants to large fluctuations in the levels of these substances and necessitate stringent intracellular homeostatic mechanisms, but the special status of plants as the principal points of entry of these substances into the food chain means that the mechanisms by which plants dispose of or sequester heavy metals have repercussions for all heterotrophic organisms.

In addition, bioremediation, the use of plants or microbes for the extraction and/or degradation of xenobiotics for environmental cleanup, is attracting increasing interest because of its potentially low cost by comparison with conventional physical and chemical methods. In the case of pollutants, such as heavy metals that cannot be degraded, phytoremediation is particularly appealing because of the ease with which plants can be harvested. Therefore, there is currently a great interest in the identification of native plant species or in the identification of genes from model systems useful for engineering crop species for increased resistance to and/or increased accumulation of heavy metals. In the latter category is the search for new heavy metal-binding peptides for the purpose of better understanding the mechanisms underlying the alleviation of heavy metal stress by plants and of obtaining genes encoding such peptides or the enzymes responsible for their synthesis. The identification and characterization of these genes will facilitate the development of a "mix-and-match" approach to the manipulation of plant heavy metal responses according to the specific requirements of the type of environmental site that is to be phytoremediated.

To date, three classes of peptides have been shown to contribute to heavy metal resistance in plants: glutathione (GSH), metallothioneins (MTs), and phytochelatins (PCs). The thiol peptide, GSH ($\gamma$-Glu-Cys-Gly), and in some species its variant homoglutathione (h-GSH, $\gamma$-Glu-Cys-$\beta$-Ala), is considered to influence the form and toxicity of heavy metals, such as As, Cd, Cu, Hg, and Zn, in several ways. These include the following mechanisms: direct metal binding (Fuhr and Rabenstein, 1973, J. Am. Chem. Soc. 95:6944–6950), promotion of the transfer of metals to other ligands (e.g, PCs and MTs; Freedman et al., 1989, J. Biol. Chem. 264:5598–5605), provision of reducing equivalents for the generation of metal oxidation states more amenable to binding by MTs and possibly PCs (Freedman et al., supra), removal of the active oxygen species formed as a result of exposure of cells to heavy metals (Inze and Van Montagu, 1995, Current Opinion in Biotech. 6:153–158), the formation of transport-active metal complexes with GSH (Li et al., 1997, Proc. Natl. Acad. Sci. U.S.A. 94:42–47), and by serving as a precursor for the biosynthesis of PCs and other cysteinyl peptides (Grill et al., 1987, Proc. Natl. Acad. Sci. U.S.A. 84:439–443; Meuwly et al., 1995, Plant J. 7:391–400).

The MTs, another class of peptides previously implicated in heavy metal metabolism in plants, are small (4–8 kDa), cysteine-rich metal-binding polypeptides which are induced in cells by the presence of heavy metals. MTs, which contain multiple Cys-Xaa-Cys motifs, confer tolerance to a broad range of metals in mammals (Hamer, 1986, Annu. Rev. Biochem. 55:913–951) but appear to be involved primarily in Cu homeostasis in plants (Zhou and Goldsbrough, 1994, Plant Cell 6:875–884). Arabidopsis MT1 and MT2 confer tolerance to high levels of $Cu^{2+}$ but only to low levels of $Cd^{2+}$ when heterologously expressed in MT-deficient cup1 $\Delta$ mutants of S. cerevisiae (Zhou and Goldsbrough, 1994, Plant Cell 6:875–884). Further, MT expression in Arabidopsis seedlings is strongly induced by $Cu^{2+}$ but not by $Cd^{2+}$ (Zhou and Goldsbrough, 1994, Plant Cell 6:875–884; Murphy et al., 1997, Plant Physiol. 113:1291–1301), and comparisons between Arabidopsis ecotypes (i.e., subspecific forms in a true species, resulting from selection within a particular habitat, which can interbreed with other members of the species) demonstrate MT2 expression to be more closely correlated with Cu-tolerance than tolerance to other metals (Murphy and Taiz, 1995, Plant Physiol. 109:945–954).

Exposure of plants to heavy metals elicits the elaboration of PCs, a class peptides that play a pivotal role in heavy metal tolerance, primarily tolerance to $Cd^{2+}$, in plants and fungi by chelating these substances and decreasing their free concentrations. PCs consist of repeating units of γ-glutamylcysteine followed by a C-terminal glycine {poly-(γ-Glu-Cys)$_n$-Gly polymer} (Rauser, 1990, Annu. Rev. Biochem. 59:61–86; Steffens, 1990, Annu. Rev. Plant Physiol. Plant Mol. Biol. 41: 553–575). Unlike MTs, PCs are synthesized posttranslationally from GSH (γ-Glu-Cys-Gly) by PC synthases (i.e., γ-glutamylcysteine dipeptidyl transpeptidases, EC 2.3.2.15), which transfer a γ-glutamylcysteine moiety from GSH to a second molecule or a previously synthesized PC molecule (Rauser, 1990, Annu. Rev. Biochem. 59:61–86; Zenk, 1996, Gene 179:21–30). Found in some fungi and in all plant species investigated to date (Rauser, 1990, Annu. Rev. Biochem. 59:61–86; Zenk, 1996, Gene 179:21–30), PCs bind heavy metals, such as $Cd^{2+}$, with high affinity, and localize together with $Cd^{2+}$ to the vacuole of intact cells (Vogeli-Lange and Wagner, 1990, Plant Physiol. 92:1086–1093). As indicated by the hypersensitivity of PC-deficient Arabidopsis cad1 mutants to $Cd^{2+}$ but not to $Cu^{2+}$ (Howden et al., 1995, Plant Physiol. 107:1059–1066), PCs contribute most markedly to $Cd^{2+}$ detoxification in planta. PC-dependent vacuolar $Cd^{2+}$ sequestration is best understood in the fission yeast *Schizosaccharomyces pombe,* in which the hmt1$^+$ gene product, a PC-selective ATP-binding cassette (ABC) transporter, pumps Cd.PCs and apo-PCs from the cytosol into the vacuole at the expense of ATP (Ortiz et al., 1992, EMBO J. 11:3491–3499; Ortiz et al., 1995, J. Biol. Chem. 270:47214728).

In addition to heavy metal tolerance mechanisms involving GSH, MTs, and PCs, the results of recent studies are consistent with the transport of free $Cd^{2+}$ into the plant vacuole via a $Cd^{2+}/H^+$ antiport (Salt and Wagner, 1993,.J. Biol. Chem. 268:12297–12302). However, the physiological significance of such a process remains to be determined.

Although PCs play an important role in heavy metal tolerance in plants, the molecular identity of the enzyme(s) responsible for the elaboration of these peptides remained elusive. The prior art teaches the partial purification of heavy metal-, primarily $Cd^{2+}$, activated enzymes (i.e., γ-glutamylcysteine dipeptidyl transpeptidases, EC 2.3.2.15, more commonly referred to as PC synthases) which are competent in the synthesis of PCs from GSH, homo-GSH or related thiol peptides by transfer of a γ-glutamylcysteine unit from one thiol tripeptide to another or to a previously synthesized PC molecule (Grill et al., 1989, Proc. Natl. Acad. Sci. U.S.A. 89:6838–6842; Zenk, 1996, Gene 179:21–30). However, the prior art does not disclose the isolation or identification of the moiety or moieties involved in PC synthesis at either the protein or nucleic acid level.

Thus, despite the need for efficient and cost-effective methods for the bioremediation of contaminated soils and groundwaters, and the established importance of PCs for heavy metal accumulation and detoxification in plants, the identification and isolation of the enzyme(s) responsible for PC biosynthesis and for the phytoremediation of heavy metals has until now not been achieved. The present invention meets these need.

BRIEF SUMMARY OF THE INVENTION

The invention includes an isolated nucleic acid encoding a phytochelatin synthase. In one aspect, the nucleic acid shares at least about 15% homology with at least one of AtPCS1 (SEQ ID NO: 1), AtPCS2 (SEQ ID NO: 3), TaPCS1 (SEQ ID NO: 5), SpPCS (SEQ ID NO: 7), and CePCS (SEQ ID NO: 9).

In another aspect, the isolated nucleic acid is selected from the group consisting of (SEQ ID NO: 1), (SEQ ID NO: 3), (SEQ ID NO: 5), (SEQ ID NO: 7), (SEQ ID NO: 9).

The invention further includes an isolated nucleic acid encoding a plant phytochelatin synthase, wherein the phytochelatin synthase shares at least about 15% homology with at least one of AtPCS1 (SEQ ID NO: 2), AtPCS2 (SEQ ID NO: 4), TaPCS1 (SEQ ID NO: 6), SpPCS (SEQ ID NO: 8), and CePCS (SEQ ID NO: 10).

The invention also includes an isolated polypeptide comprising a phytochelatin synthase. In one aspect, the isolated polypeptide shares at least about 15% homology with at least one of SEQ ID NO: 2, SEQ ID NO: 4, SEQ ID NO: 6, SEQ ID NO: 8, and SEQ ID NO: 10.

In another aspect, the isolated polypeptide comprising a phytochelatin synthase is at least one of SEQ ID NO: 2, SEQ ID NO: 4, SEQ ID NO: 6, SEQ ID NO: 8, and SEQ ID NO: 10.

In another aspect, the isolated nucleic acid encoding a phytochelatin synthase further comprises a reporter nucleic acid covalently linked thereto.

In yet another aspect, the reporter nucleic acid encodes a reporter polypeptide selected from the group consisting of a FLAG octapeptide, a human influenza virus hemagglutinin epitope, a β-glucuronidase epitope, a green fluorescent protein epitope, and a luciferase epitope.

The invention includes a recombinant cell comprising an isolated nucleic acid wherein the nucleic acid shares at least about 15% homology with at least one of AtPCS1 (SEQ ID NO: 1), AtPCS2 (SEQ ID NO: 3), TaPCS1 (SEQ ID NO: 5), SpPCS (SEQ ID NO: 7), and CePCS (SEQ ID NO: 9).

In one aspect, the cell is selected from the group consisting of a prokaryotic cell and a eukaryotic cell.

The invention also includes a vector comprising an isolated nucleic acid, wherein the nucleic acid shares at least about 15% homology with at least one of ATPCS1 (SEQ ID NO: 1), AtPCS2 (SEQ ID NO: 3), TAPCS1 (SEQ ID NO: 5), SpPCS (SEQ ID NO: 7), and CePCS (SEQ ID NO: 9).

The invention includes a transgenic plant, the cells, seeds and progeny of which comprise an isolated nucleic acid encoding a phytochelatin synthase, wherein the nucleic acid comprises at least one of AtPCS1 (SEQ ID NO: 1), AtPCS2 (SEQ ID NO: 3), TaPCS1 (SEQ ID NO: 5), SpPCS (SEQ ID NO: 7) and CePCS (SEQ ID NO: 9), or a fragment thereof, and wherein the nucleic acid shares at least about 15% homology with at least one of SEQ ID NO: 1, SEQ ID NO: 3, SEQ ID NO: 5, SEQ ID NO: 7, and SEQ ID NO: 9.

The invention further includes a transgenic plant, the cells, seeds and progeny of which comprise an isolated nucleic acid encoding a phytochelatin synthase, or a fragment thereof, wherein the phytochelatin synthase shares at least about 15% homology with at least one of AtPCS1 (SEQ ID NO: 2), AtPCS2 (SEQ ID NO: 4), TaPCS1 (SEQ ID NO: 6), SpPCS (SEQ ID NO: 8), and CePCS (SEQ ID NO: 10).

The invention includes a method of preventing removal of a heavy metal from soil. The method comprises growing in the soil a transgenic plant comprising an isolated nucleic acid encoding a phytochelatin synthase in an antisense orientation and harvesting the plant from the soil, thereby preventing removal of the heavy metal from the soil.

The invention also includes a method of removing a heavy metal from soil. The method comprises growing in the soil a transgenic plant comprising an isolated nucleic acid encoding a phytochelatin synthase and harvesting the plant from the soil, thereby removing the heavy metal from the soil. In one aspect, the heavy metal is selected from the group consisting of cadmium, arsenate, arsenite, mercury, lead, zinc, nickel, bismuth, selenium, silver, gold, and copper.

The invention includes a method of generating a transgenic heavy metal resistant plant. The method comprises introducing to the cells of the plant an isolated nucleic acid encoding a phytochelatin synthase, thereby generating a transgenic heavy metal resistant plant.

The invention further includes a method of biosynthesizing a phytochelatin. The method comprises contacting an isolated phytochelatin synthase with a sufficient amount of glutathione, or a glutathione-related thiol peptide, under conditions which permit biosynthesis of a phytochelatin from the glutathione or related thiol peptide, thereby biosynthesizing a phytochelatin.

In one aspect, the biosynthesis is biosynthesis selected from the group consisting of a biosynthesis performed in vitro, and a biosynthesis performed in vivo, In another aspect, the glutathione-related thiol peptide is selected from the group consisting of a homoglutathione, a PC2, a PC3, a PC4, a homo-glutathione, a hydroxymethyl-glutathione, and a γ-glutamylcysteinylglutamic acid.

In yet another aspect, the phytochelatin is selected from the group consisting of a PC2, a PC3, a PC4, a homo-PC2, a hydroxymethyl-PC2, an iso-PC2(Glu), and a desGly-PC2.

In-even another aspect, the phytochelatin synthase is selected from the group consisting of a AtPCS1, a AtPCS2, a TaPCS1, a SpPCS, and a CePCS.

The invention includes a method of transferring a γ-glutamylcysteine unit from one thiol peptide to another. The method comprises contacting an isolated phytochelatin synthase with a glutathione, or a related thiol peptide, under conditions which permit transfer of the γ-glutamylcysteine unit from one thiol peptide to another, thereby transferring a γ-glutamylcysteine unit from one thiol peptide to another.

The invention also includes a method of decreasing the level of a heavy metal in a harvestable portion of a plant. The method comprises expressing a nucleic acid encoding a phytochelatin synthase in a non-harvestable portion of a plant, thereby decreasing the level of a heavy metal in the harvestable portion of the plant.

In one aspect, the method further comprises inhibiting expression of a phytochelatin synthase in the harvestable portion of the plant.

The invention includes a method of removing a heavy metal from groundwater. The method comprises growing in the groundwater a transgenic plant comprising an isolated nucleic acid encoding a phytochelatin synthase and harvesting the plant from the groundwater, thereby removing the heavy metal from the groundwater.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiment(s) which are presently preferred. It should be understood, however, that the invention is not limited to the precise arrangements and instrumentalities shown. In the drawings:

FIG. 1 is a diagram depicting the alignment of the deduced amino acid sequence of the polypeptide encoded by AtPCS1(SEQ ID NO:2) and its 46.7 and 40.8 kDa homologs from S. pombe (SEQ ID NO:8)(GenBank accession number Q10075) and C. elegans (SEQ ID NO:10) (GenBank Accession number Z665 13), respectively. Sequences were aligned by the CLUSTAL W method (Higgins and Sharp, 1988, Gene 73:237–240). Identical residues are shown in white on a black background. Similar residues are shown in black on a gray background. Gaps introduced to maximize the alignments are denoted by hyphens. Abbreviations for the amino acid residues are: A, Ala; C, Cys; D, Asp; E, Glu; F, Phe; G, Gly; H, His; I, Ile; K, Lys; L, Leu; M, Met; N, Asn; P, Pro; Q, Gln; R, Arg; S, Ser; T, Thr; V, Val; W, Trp; and Y, Tyr.

FIG. 9A is a diagram depicting the CLUSTAL W alignment (Thompson et al., 1994, Nucleic Acids Res. 22:4673–4680) of the amino acid sequences of wheat (TaPCS1; SEQ ID NO: 6), Arabidopsis thaliana (AtPCS1; SEQ ID NO: 2), S. pombe (SpPCS; SEQ ID NO: 8), and C. elegans (CePCS; SEQ ID NO: 10). Amino acids which are identical are shown in black boxes, similar amino acid residues are indicated within light gray-boxes.

FIG. 14A is a diagram (comprising two panels) depicting that PCS mediates phytochelatin synthesis. Crude extracts of *S. pombe* control wildtype cells (top panel) or *S. pombe* ΔSpPCS cells (bottom panel) were incubated in 200 mM Tris-Cl (pH 8.0), 1 mM dithiothreitol (DTT), 1 mM GSH and 0.1 mM $CdCl_2$ at 30° C. for 30–120 minutes and the reaction products were monobromobimane-labeled and analyzed by HPLC. Peak 1 corresponds to free GSH, and peak 2 represents PC2.

FIG. 14B is an image depicting a Western blot analysis of extracts from ΔSpPCS cells harboring SpPCS-HA(left lane) or empty vector (right lane) using anti-HA monoclonal antibody (BAbCo, Berkeley, Calif.). The sizes of the molecular mass standards run in parallel with the sample lanes are indicated along the left side of the figure.

FIG. 14C is an image of a western blot depicting that SpPCS-HA was purified from crude extracts of cells expressing SpPCS-HA using anti-HA antibody affinity column. Protein was eluted from the affinity column using 5 mg HA peptide (YPYDVPDYA) and the eluted fraction was analyzed by SDS-PAGE (left lane) and Western blotting (right lane). A second band, possibly a proteolytic fragment of the 46 kDa SpPCS-HA, was detected at about 30 kDa.

FIG. 14D is a graph depicting the PC synthesis by purified SpPCS-HA. Affinity-purified SpPCS-HA was assayed for PC synthase activity and the resulting products were labeled and analyzed by HPLC as described previously elsewhere herein. Peaks 1 and 2 represent free GSH and PC2, respectively.

FIG. 16, comprising FIGS. 16A and 16B, lists the nucleotide sequence (SEQ ID NO: 1) of a DNA encoding AtPCS1.

FIG. 17, comprising FIGS. 17A, 17B, and 17C, lists the nucleotide sequence (FIGS. 17A and 17B; SEQ ID NO: 3) of the gene encoding AtPCS2 and the amino acid sequence (FIG. 17C; SEQ ID NO: 4) of AtPCS2.

FIG. 18, comprising FIGS. 18A, 18B, and 18C, lists the nucleotide sequence (FIGS. 18A and 18B; SEQ ID NO: 5) of the gene encoding TaPCS1 and the amino acid sequence (FIG. 18C; SEQ ID NO: 6) of TaPCS1.

FIG. 19, comprising FIGS. 19A and 19B, lists the nucleotide sequence (FIG. 19A; SEQ ID NO: 7) of the gene encoding SpPCS and the amino acid sequence (FIG. 19B, SEQ ID NO: 8) of SpPCS.

FIG. 20, comprising FIGS. 20A and 20B, lists the nucleotide sequence (FIG. 20A; SEQ ID NO: 9) of the gene encoding CePCS and the amino acid sequence (FIG. 20B, SEQ ID NO: 10) of CePCS.

DETAILED DESCRIPTION OF THE INVENTION

Figure 2:
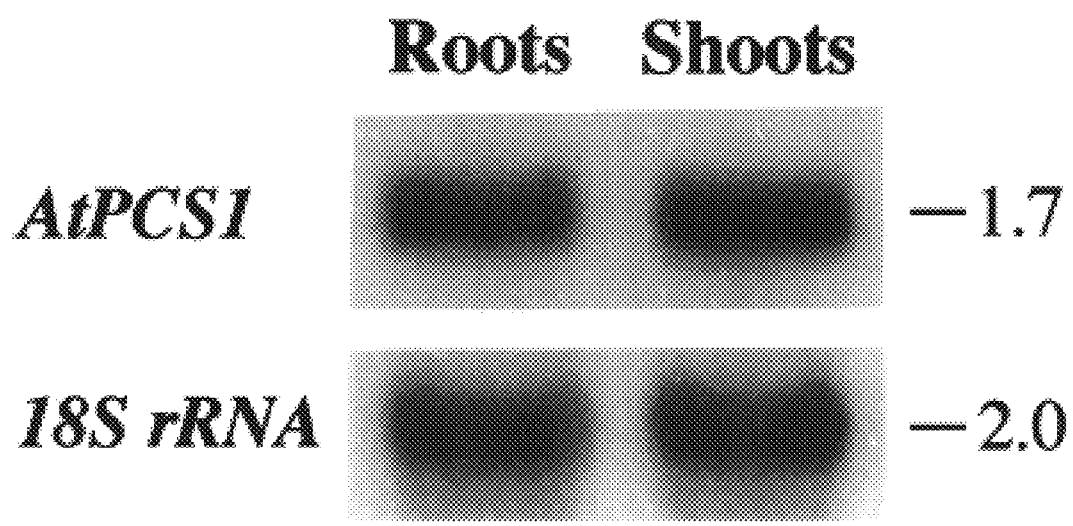
FIG. 2 is an image of a Northern blot depicting the expression of AtPCS1 transcript in roots and shoots of Arabidopsis. Total RNA was extracted from 21-day-old Arabidopsis seedlings and the RNA was hybridized with $^{32}$P-labeled, random primed AtPCS1 cDNA. Ten μg of RNA was loaded on each gel lane. The 1.7 kb bands shown were the only $^{32}$P-labeled bands detected after probing the blots with ATPCS1. Also shown are the results of hybridizing the same blots with a probe directed against 18S rRNA (2.0 kb) to verify that similar amounts of RNA were loaded onto each gel lane.

The invention is based on the discovery of novel phytochelatin synthases from plants, yeast and nematodes. Prior to the instant disclosure, no phytochelatin synthase had been identified or isolated from any source such that no amino acid or nucleic acid sequence information was available for these proteins. These enzymes are important in that phytochelatins are useful molecules which bind to and sequester, inter alia, heavy metals. As a result of the present invention, new insights into the phenomena associated with heavy metal tolerance and/or resistance and phytoremediation are possible. The molecular identification of PC synthases provides a means, as is evident from the description of the present invention, for the manipulation of plants and the cells thereof, to affect heavy metal tolerance, resistance and accumulation associated with PC synthase-catalyzed PC biosynthesis for the bioremediation of contaminated soils and groundwaters. Therefore, isolation and purification of phytochelatin synthase and the nucleic acids encoding the same makes possible the large-scale production of these useful compounds and the development of recombinant plants and cells producing such compounds all of which will be useful in bioremediation to assist environmental cleanup efforts.

The process of "storage excretion" is a necessity for plants. Whereas mammals have the option of excreting biotoxins to the extracellular medium for elimination by the kidneys, plants are nearly totally reliant on the sequestration of noxious compounds in the central vacuole, which frequently accounts for 40–90% of the total intracellular volume. Due to the virtual absence of specialized excretory organs and the presence of massive vacuoles in plants, a process termed intracellular compartmentation that is probably only an intermediate step in the elimination of xenobiotics from the cytosol of mammalian cells, is believed to constitute a terminal phase of detoxification in plants.

The data disclosed herein establish that two plant nucleic acids, AtPCS1 and AtPCS2, isolated from *Arabidopsis thaliana,* a nucleic acid from wheat, TaPCS1, a nucleic acid from *C. elegans,* CePCS, and one from *S. pombe,* SpPCSe, each encode a phytochelatin synthase. The data further establish that the novel phytochelatin synthases participate in phytochelatin biosynthesis and, more importantly, heavy metal sequestration as exemplified by binding and transport of cadmium, arsenate, arsenite, lead, mercury and copper.

The discovery of these genes in the present invention is important on several levels. The identification of these genes and the elucidation of the catalytic activity of their translation products represents the first combined molecular identification and biochemical definition of phytochelatin synthases from any organism. In the present invention, nucleic acids encoding PC synthases have been identified and isolated from plants, yeast and worms and the biochemical function of the proteins encoded thereby has been defined. Further, the identification and isolation of these genes and their encoded products permits a plant element, critical for removal of compounds from the cytosol that can form GSH conjugates, to be studied and manipulated.

Two novel plant genes isolated from *Arabidopsis thaliana,* AtPCS1 and AtPCS2, which encode plant phytochelatin synthases involved in the biosynthesis of PCs, have been disclosed in the present invention. The genes are exemplified herein as SEQ ID NO: 1 and SEQ ID NO: 3, being AtPCS1 and AtPCS2, respectively. Proteins encoded by plant AtPCS1 and AtPCS2 (SEQ ID NO: 2 and SEQ ID NO: 4, respectively) thus represent novel enzymes never before characterized or isolated from any source.

Figure 18A:
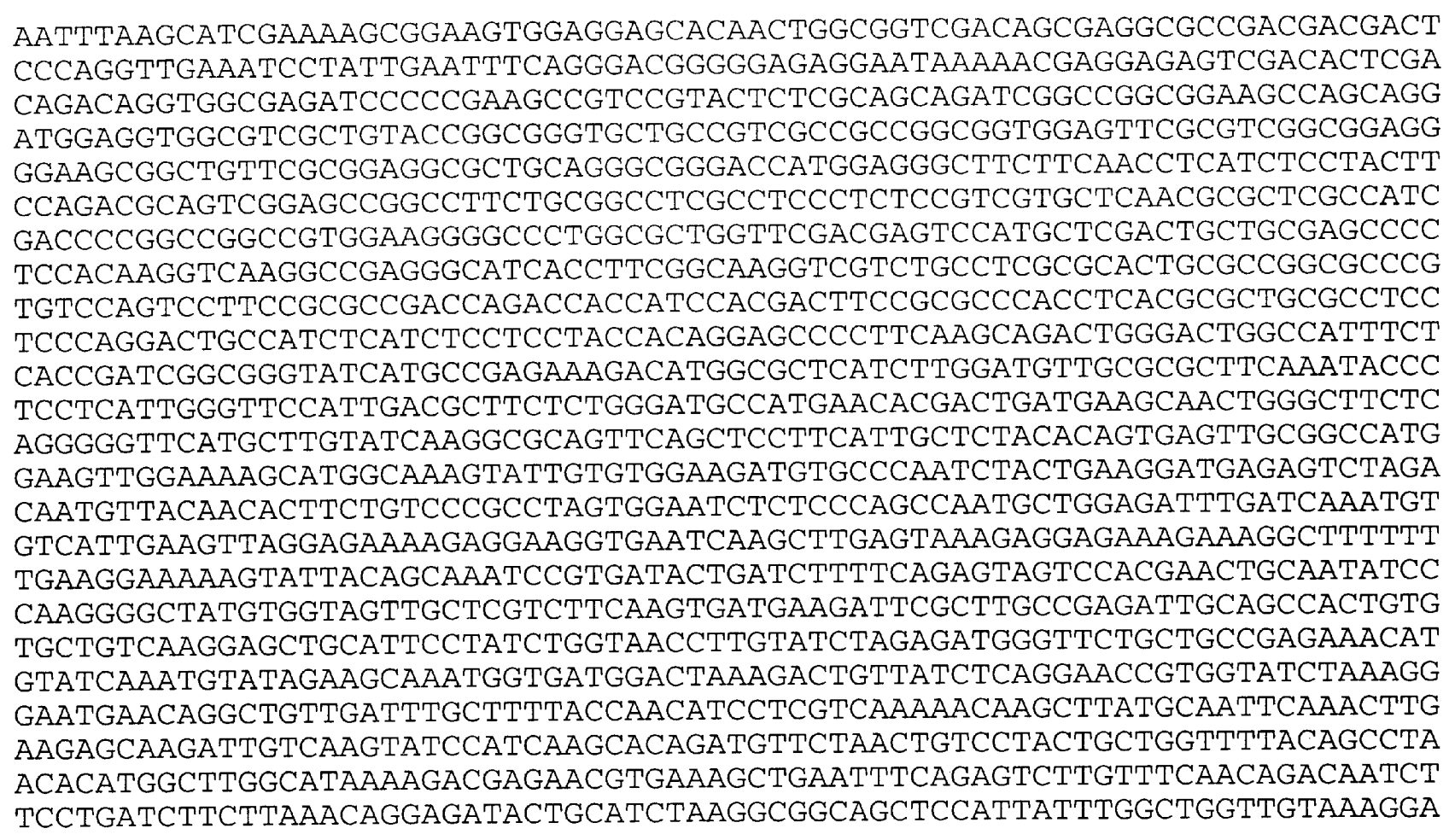

Additionally, a novel gene isolated from wheat, *Triticum aestivum*, TaPCS1 (SEQ ID NO: 5; GenBank Accession No. AF093752; FIG. 18) encoding a protein having the amino acid sequence SEQ ID NO: 6 is also disclosed, as is a nucleic acid isolated from the yeast *Schizosaccharomyces pombe*, SpPCS (SEQ ID NO: 7; GenBank Accession No. Q10075; FIG. 19), encoding a novel yeast PCS polypeptide, SpPCS (SEQ ID NO: 8). Further, the invention also includes a *Caenorhabditis elegans* gene, CePCS (SEQ ID NO: 9; GenBank Accession No. Z66513; FIG. 20), encoding a novel animal PCS, CePCS (SEQ ID NO: 10). The predicted amino acid sequences of AtPCS1, TaPCS1, CePCS, and SpPCS are disclosed in FIG. 9A.

It has been further discovered in the present invention that when nucleic acid encoding AtPCS1 is introduced into a mutant yeast strain which is hypersensitive to cadmium toxicity, the nucleic acid suppresses the cadmium-sensitive phenotype and, indeed, confers resistance to cadmium levels in excess of those tolerated by the wild type yeast strain from which the mutant is derived. Similarly, introduction of the wheat, yeast, and *C. elegans* gene into yeast also conferred resistance to $Cd^{2+}$ thereby demonstrating that these genes encode functional phytochelatin synthases. Further, expression of the wheat TaPCS1 nucleic acid or the SPPCS nucleic in *S. cerevisiae* caused $Cd^{2+}$ tolerance. Also, expression of TaPCS1 in *S. cerevisiae* caused an increase in the accumulation of $Cd^{2+}$ in the cells even at low $Cd^{2+}$ levels. In addition, the data disclosed herein demonstrate that purified recombinant SpPCS protein synthesizes phytochelatins from glutathione in vitro and that expression of TaPCS1 or SpPCS in *S. cerevisiae* induced phytochelatin biosynthesis in vivo. Further, deletion of SpPCS in *S. pombe* caused increased sensitivity to cadmium and copper and this deletion mutant (ΔSpPCS) did not synthesize phytochelatins.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

An "isolated nucleic acid," as used herein, refers to a nucleic acid sequence which has been separated from the sequences which flank it in a naturally occurring state, e.g., a nucleic acid fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid (e.g., RNA, DNA or protein) in its natural state. The term therefore includes, for example, a recombinant nucleic acid which is incorporated into a vector; into an autonomously replicating plasmid or virus; or into the genomic DNA of a prokaryote or eukaryote; or which exists as a separate molecule (e.g., as a cDNA or a genomic or cDNA fragment produced by PCR or restriction enzyme digestion) independent of other sequences. It also includes a recombinant nucleic acid which is part of a hybrid gene encoding additional polypeptide sequence.

Further discovered in the present invention is the fact that the plant phytochelatin synthases of the invention bind cadmium directly in a stoichiometric ratio of approximately 6 cadmium molecules for each AtPCS1. In addition, the data disclosed herein demonstrate that expression of AtPCS1 mediates the synthesis of PCs including $PC_2$, $PC_3$ and $PC_4$, thereby facilitating the vacuolar transport and storage of heavy metals by PCs.

The identification of two plant phytochelatin synthases, AtPCS1 and AtPCS2 (SEQ ID NO: 2 and SEQ ID NO: 4, respectively; see FIGS. 16 and 17, respectively), is described in detail in the experimental details section. Further, the identification of a PC synthase from: wheat (TaPCS1 {SEQ ID NO: 5} and TaPCS1 {SEQ ID NO: 6}), yeast (SpPCS {SEQ ID NO: 7}) and SpPCS {SEQ ID NO: 8}), and nematodes (CePCS {SEQ ID NO: 9} and CePCS {SEQ ID NO: 10}) are also described in the detail elsewhere herein. Once armed with the present invention, the skilled artisan will know how to identify and isolate additional genes encoding other phytochelatin synthases from plants and other organisms, involved in sequestration of a variety of compounds by following the procedures described herein.

A gene encoding a PC synthase is isolated using any one of several known molecular procedures. For example, primers comprising conserved regions of the sequences of any of ATPCS1 (SEQ ID NO: 1), AtPCS2 (SEQ ID NO: 3), TaPCS1 (SEQ ID NO: 5), SpPCS (SEQ ID NO: 7), and CePCS (SEQ ID NO: 9) may be used as probes to isolate, by polymerase chain reaction (PCR) or -by direct hybridization, as yet unknown AtPCS1, AtPCS2, TaPCS1, SpPCS, and CePCS homologs in a DNA library comprising specific DNAs. Alternatively, antibodies directed against AtPCS1 (SEQ ID NO: 2), AtPCS2 (SEQ ID NO: 4), TaPCS1 (SEQ ID NO: 6), SpPCS (SEQ ID NO: 8), or CePCS (SEQ ID NO: 10) may be used to isolate clones encoding a PC synthase from an expression library comprising specific DNAs. The isolation of primers, probes, molecular cloning and the generation of antibodies are procedures that are well known in the art and are described, for example, in Sambrook et al. (1989, In: Molecular Cloning: A Laboratory Manual, Cold Spring Harbor, N.Y.), Ausubel et al. (1997, In: Current Protocols in Molecular Biology, Green & Wiley, New York), and in Harlow et al. (1988, In: Antibodies, A Laboratory Manual, Cold Spring Harbor, N.Y.).

The invention includes isolated nucleic acids encoding phytochelatin synthases, which phytochelatin synthases are capable of synthesizing PCs which will, in turn, bind heavy metals including cadmium. Preferably, the nucleic acid encoding a phytochelatin synthase is at least about 15% homologous to at least one of AtPCS1 (SEQ ID NO: 1), AtPCS2 (SEQ ID NO: 3), TaPCS1 (SEQ ID NO: 5), SpPCS (SEQ ID NO: 7), and CePCS (SEQ ID NO: 9). More preferably, the isolated nucleic acid encoding a phytochelatin synthase is at least about 25%, preferably, at least about 35%, more preferably, at least about 45%, even more preferably, at least about 55%, more preferably, at least about 65%, even more preferably, at least about 75%, yet more preferably, at least about 85% homologous, more preferably, at least about 95% and even more preferably, at least about 99% homologous to at least one of AtPCSJ (SEQ ID NO: 1), AtPCS2 (SEQ ID NO: 3), TaPCS1 (SEQ ID NO: 5), SpPCS (SEQ ID NO: 7), and CePCS (SEQ ID NO: 9). More preferably, the isolated nucleic acid encoding a phytochelatin synthase is Arabidopsis AtPCS1, or AtPCS2, or wheat TaPCS1 , or yeast SpPCS, or worm CePCS. Most preferably, the isolated nucleic acid encoding a phytochelatin synthase is SEQ ID NO: 1, SEQ ID NO: 3, SEQ ID NO: 5, SEQ ID NO: 7, or SEQ ID NO: 9.

Thus, the invention should be construed to include nucleic acids which encode Arabidopsis AtPCS1 (SEQ ID NO: 2) and AtPCS2 (SEQ ID NO: 4), wheat TaPCS1 (SEQ ID NO: 6), yeast SpPCS (SEQ ID NO: 8), and worm CePCS (SEQ ID NO: 10), as well as nucleic acids homologous to Arabidopsis AtPCS1 (SEQ ID NO: 1), AtPCS2 (SEQ ID NO: 3), wheat TaPCS1 (SEQ ID NO: 5), yeast SpPCS (SEQ ID NO: 7), and worm CePCS (SEQ ID NO: 9).

In addition, when the term "homology" is used herein to refer to the nucleic acids and proteins, it should be construed to be applied to homology at both the nucleic acid and the amino acid levels.

Thus, the invention also includes an isolated nucleic acid encoding a phytochelatin synthase where the nucleic acid encodes a protein which is preferably, at least about 15% homologous to at least one of AtPCS1 (SEQ ID NO: 2), AtPCS2 (SEQ ID NO: 4), TaPCS1 (SEQ ID NO: 6), SpPCS (SEQ ID NO: 8), and CePCS (SEQ ID NO: 10). More preferably, the isolated nucleic acid encodes a phytochelatin synthase which is at least about 25%, more preferably, at least about 35%, even more preferably, at least about 45%, more preferably, at least about 55%, yet more preferably, at least about 65%, even more preferably, at least about 75%, yet more preferably, at least about 85% homologous, and more preferably, at least about 95%, and even more preferably, at least about 99% homologous to at least one of AtPCS1 (SEQ ID NO: 2), AtPCS2 (SEQ ID NO: 4), TaPCS1 (SEQ ID NO: 6), SpPCS (SEQ ID NO: 8), and CePCS (SEQ ID NO: 10). More preferably, the isolated nucleic acid encodes a plant phytochelatin synthase that is Arabidopsis AtPCS1 or AtPCS2, or wheat TaPCS1, or yeast SpPCS, or nematode CePCS. Most preferably, the isolated nucleic acid encodes a phytochelatin synthase having the amino acid sequence SEQ ID NO: 2, SEQ ID NO: 4, SEQ ID NO: 6, SEQ ID NO: 8, or SEQ ID NO: 10.

Therefore, the invention should be construed to include nucleic acids which encode Arabidopsis AtPCS1 (SEQ ID NO: 2) and AtPCS2 (SEQ ID NO: 4), Triticum TaPCS1 (SEQ ID NO: 6), yeast SpPCS (SEQ ID NO: 8), and Caenorhabditis CePCS (SEQ ID NO: 10), as well as nucleic acids which encode a protein homologous to AtPCS1, AtPCS2, TaPCSl, SpPCS, and CePCS.

By "phytochelatin synthase" as used herein, is meant a protein which is involved in the biosynthesis of phytochelatins. These proteins (also referred to as γ-glutamylcysteine dipeptidyl transpeptidases) synthesize PCs from GSH, homo-GSH, and related thiol peptides by transfer of a γ-glutamylcysteine unit from a thiol peptide to another or to a previously synthesized PC molecule (Rauser, 1996, Annu. Rev. Biochem. 59:61–86; Zenk, 1990, Gene 179:21–30).

"Phytochelatins," in turn, are poly-(γ-Glu-Cys)$_n$-Xaa polymers that bind heavy metals with high affinity.

By the term "nucleic acid encoding a phytochelatin synthase" as used herein is meant a nucleic acid encoding a polypeptide capable of producing, or which is associated with the accumulation of, phytochelatins.

The present invention includes an isolated nucleic acid encoding a biologically active polypeptide fragment of a phytochelatin synthase. Preferably, the isolated nucleic acid encoding a biologically active polypeptide fragment of a phytochelatin synthase is at least about 15% homologous to a nucleic acid encoding a fragment of at least one of AtPCS1 (SEQ ID NO: 1), AtPCS2 (SEQ ID NO: 3), TaPCS1 (SEQ ID NO: 5), SpPCS (SEQ ID NO: 7), and CePCS (SEQ ID NO: 9). More preferably, the isolated nucleic acid encoding a biologically active polypeptide fragment of a phytochelatin synthase is at least about 25%, more preferably, at least about 35%, even more preferably, at least about 45%, more preferably, at least about 55%, yet more preferably, at least about 65%, even more preferably, at least about 75%, yet more preferably, at least about 85%, and even more preferably, at least about 95%, and even more preferably, at least about 99% homologous to a fragment of at least one of tPCS1 (SEQ ID NO: 1), AtPCS2 (SEQ ID NO: 3), TaPCS1 (SEQ ID NO: 5), SpPCS (SEQ ID NO: 7), and CePCS (SEQ ID NO: 9). More preferably, the isolated nucleic acid encoding a biologically active polypeptide fragment of a phytochelatin synthase is a nucleic acid encoding a fragment of AtPCS1, AtPCS2, TaPCS1, SpPCS, or CePCS. Most preferably, the isolated nucleic acid encoding a biologically active polypeptide fragment of a phytochelatin synthase is a nucleic acid encoding a fragment of SEQ ID NO: 1, SEQ ID NO: 3, SEQ ID NO: 5, SEQ ID NO: 7, or SEQ ID NO: 9.

As used herein, by the term "biologically active" as it refers to phytochelatin synthase activity as used herein, is meant a polypeptide, or a fragment thereof, which is capable of transferring a γ-glutamylcysteine unit from a thiol peptide to another or to a previously synthesized phytochelatin molecule.

Also included in the invention is an isolated nucleic acid encoding a biologically active polypeptide fragment of a phytochelatin synthase. Preferably, the isolated nucleic acid encoding a biologically active polypeptide fragment of a phytochelatin synthase is at least about 15% homologous to a nucleic acid encoding a biologically active polypeptide fragment of at least one of AtPCS1 (SEQ ID NO: 2), AtPCS2 (SEQ ID NO: 4), TaPCS1 (SEQ ID NO: 6), SpPCS (SEQ ID NO: 8), and CePCS (SEQ ID NO: 10). More preferably, the isolated nucleic acid encoding a biologically active polypeptide fragment of a phytochelatin synthase is at least about 25%, more preferably, at least about.35%, even more preferably, at least about 45%, more preferably, at least about 55%, yet more preferably, at least about 65%, even more preferably, at least about 75%, yet more preferably, at least about 85%, yet more preferably, at least about 90%, and even more preferably, at least about 99% homologous to a nucleic acid encoding a biologically active polypeptide fragment of at least one of AtPCS1 (SEQ ID NO: 2), AtPCS2 (SEQ ID NO: 4), TaPCS1 (SEQ ID NO: 6), SpPCS (SEQ ID NO: 8), and CePCS (SEQ ID NO: 10). More preferably, the isolated nucleic acid encoding a biologically active polypeptide fragment of a phytochelatin synthase is a nucleic acid encoding a biologically active polypeptide fragment of AtPCS1, AtPCS2, TaPCS1, SpPCS, or CePCS. Most preferably, the isolated nucleic acid encoding a biologically active polypeptide fragment of a phytochelatin synthase is a nucleic acid encoding a biologically active polypeptide fragment of SEQ ID NO: 2, SEQ ID NO: 4, SEQ ID NO: 6, SEQ ID NO: 8, or SEQ ID NO: 10.

Preferably, the isolated nucleic acid encoding a biologically active polypeptide fragment of a PC synthase is about 200 nucleotides in length. More preferably, the isolated nucleic acid encoding a biologically active polypeptide fragment of a PC synthase is about 400 nucleotides, even more preferably, at least about 600, yet more preferably, at least about 800, even more preferably, at least about 1000, more preferably, at least about 1200, even more preferably 1300, and yet more preferably 1400 nucleotides in length.

The invention further includes a vector comprising an isolated nucleic acid encoding a PC synthase and a vector comprising nucleic acid sequence encoding a biologically active fragment thereof. The procedures for the generation of a vector encoding a PC synthase, or fragment thereof, are well known in the art once the sequence of the gene is known, and are described, for example, in Sambrook et al., supra, Ausubel et al., supra. Suitable vectors include, but are not limited to, yeast-*E. coli* shuttle vectors as described elsewhere herein, and disarmed Agrobacterium tumor-inducing (Ti) plasmids (e.g., pBIN19) containing the target gene under the control of the cauliflower mosaic virus (CaMV) 35S promoter (Lagrimini et al., 1990, Plant Cell 2:7–18), its endogenous promoter or an inducible promoter (Bevan, 1984, Nucl. Acids Res. 12:8711–8721).

Further, the invention includes plant tissue-specific promoters such as are well-known in the art. These promoters direct expression of the nucleic acid operably linked thereto in certain tissue but not in others. One skilled in the art would appreciate, based upon the disclosure provided herein, that tissue-specific promoters would be useful for directing the expression of a nucleic acid encoding a PCS in a certain portion of the plant thereby localize heavy metals to, for example, the non-harvested portion of the plant, and away from the harvested portion of the plant.

The present invention includes a method of expressing a nucleic acid encoding a PC synthase in one tissue of a plant but not in another using a tissue-specific promoter as discussed previously. By doing so, the present invention provides a means for accumulating toxic metals in a part of the plant which is not, for instance, harvested for human or non-human animal consumption. Thus, the invention includes a method for accumulating heavy metals in a portion of the plant, such as the leaves or roots, which is not subject to animal consumption while minimizing the level of toxic heavy metals in an edible part of the same plant.

By "harvestable portion," as the term is used herein, is meant any portion of a plant which is cultivated and gathered for human use including consumption. Such harvestable portions include, but are not limited to, the fruits, seeds, leaves, stems, and roots of various plants. One skilled in the art would appreciate, based on the disclosure provided herein, that the harvested portion of one plant may be the non-harvested of another. For example, the harvested portion of a tobacco plant may be the leaves but not the roots whereas the harvested portion of a potato plant would be the root, or tuberous portion, but not the leaves of the plant. Further, the invention includes plants which have multiple portions which are harvested such as grape vines where both the fruits and leaves may be used for human consumption.

The "non-harvested portion" includes the portion(s) of a plant which are not used for human consumption. These parts may be used for purposes other than human or non-human animal consumption such as, but not limited to, portions of plants used for building materials. Therefore, the non-harvested portion of a plant may encompass portions which are useful and/or commercially important, but which are not used for human or non-human animal consumption, i.e., the portion is not ingested or used in food preparation.

Also included in the invention is a cell comprising an isolated nucleic acid encoding a PC synthase and a cell comprising an isolated nucleic acid encoding a biologically active fragment thereof The procedures for the generation of a cell encoding a PC synthase, or fragment thereof, are well know in the art once the sequence of the gene is known, and are described, for example, in Sambrook et al., supra, or Ausubel et al., 1997, supra. Suitable cells include, but are not limited to, yeast cells, bacterial cells, mammalian cells, and baculovirus-infected insect cells transformed with the gene for the express purpose of generating PC synthase polypeptide. In addition, plant cells transformed with the gene for the purpose of producing cells and regenerated plants having increased resistance to and increased capacity for heavy metal accumulation are included in the invention.

The invention also includes an isolated polypeptide comprising a PC synthase capable of producing PCs from GSH or another suitable substrate. Preferably, the isolated polypeptide comprising a PC synthase is at least about 15% homologous to at least one of AtPCS1 (SEQ ID NO: 2), AtPCS2 (SEQ ID NO: 4), TaPCS1 (SEQ ID NO: 6), SpPCS (SEQ ID NO: 8), and CePCS (SEQ ID NO: 10). More preferably, the isolated preparation of a polypeptide comprising a PC synthase is at least about 25%, more preferably, at least about 35%, even more preferably, at least about 45%, more preferably, at least about 55%, yet more preferably, at least about 65%, even more preferably, at least about 75%, more preferably, at least about 85%, even more preferably, at least about 95% and more preferably, at least about 99% homologous to at least one of AtPCS1, AtPCS2, TaPCS1, SpPCS, and CePCS. More preferably, the isolated preparation of a polypeptide comprising a PC synthase is AtPCS1, AtPCS2, TaPCS1, SpPCS, or CePCS. Most preferably, the isolated preparation of a polypeptide comprising a PC synthase is at least one of SEQ ID NOS: 2, SEQ ID NO: 4, SEQ ID NO: 6, SEQ ID NO: 8, and SEQ ID NO: 10.

As used herein, the term "isolated polypeptide" describes a polypeptide which has been separated from components which naturally accompany it. Typically, a polypeptide is isolated when at least 10%, more preferably at least 20%, more preferably at least 50%, more preferably at least 60%, even more preferably at least 75%, more preferably at least 90%, and most preferably at least 99% of the total material (by volume, by wet or dry weight, or by mole per cent or mole fraction) of a sample is the polypeptide of interest. The degree of isolation of the polypeptide can be measured by any appropriate method, e.g., by column chromatography, polyacrylamide gel electrophoresis, or by HPLC analysis. For example, a polypeptide is isolated when it is essentially free of naturally associated components or when it is separated from the native compounds which accompany it in its natural state.

Also included in the invention is an isolated biologically active polypeptide fragment of a PC synthase. Preferably, the isolated biologically active polypeptide fragment of a PC synthase is at least about 15% homologous to a biologically active polypeptide fragment of at least one of AtPCS1, AtPCS2, TaPCS1, SpPCS, and CePCS. More preferably, the isolated biologically active polypeptide fragment of a PC synthase is at least about 25%, more preferably, at least about 35%, even more preferably, at least about 45%, more preferably, at least about 55%, yet more preferably, at least about 65%, even more preferably, at least about 75% and yet more preferably, at least about 85%, even more preferably, at least about 95%, and more preferably, at least about 99% homologous to a biologically active polypeptide fragment of at least one of AtPCS1 (SEQ ID NO: 2), AtPCS2 (SEQ ID NO: 4), TaPCS1 (SEQ ID NO: 6), SpPCS (SEQ ID NO: 8), and CePCS (SEQ ID NO: 10). More preferably, the isolated biologically active polypeptide fragment of a PC synthase is a biologically active polypeptide fragment of AtPCS1, AtPCS2, TaPCS1, SpPCS, or CePCS. Most preferably, the isolated biologically active polypeptide fragment of a PC synthase is a biologically active polypeptide fragment of SEQ ID NO: 2, SEQ ID NO: 4, SEQ ID NO: 6, SEQ ID NO: 8, or SEQ ID NO: 10.

Preferably, the isolated biologically active polypeptide fragment of a PC synthase is about 60 amino acids in length. More preferably, the isolated biologically active polypeptide fragment of a PC synthase is about 130 amino acids, even more preferably, at least about 200, yet more preferably, at least about 300, even more preferably, at least about 350, and more preferably, at least about 400 amino acids in length.

As used herein, the term "homologous" refers to the subunit sequence similarity between two polymeric molecules e.g., between two nucleic acid molecules, or two polypeptide molecules. When a subunit position in both of the two molecules is occupied by the same monomeric subunit, e.g., if a position in each of two polypeptide molecules is occupied by phenylalanine, then they are homologous at that position. The homology between two sequences is a direct function of the number of matching or homologous positions, e.g., if half (e.g., 5 positions in a polymer 10 subunits in length) of the positions in two polypeptide sequences are homologous then the two sequences are 50% homologous; if 70% of the positions, e.g., 7 out of 10, are matched or homologous, the two sequences share 70% homology. By way of example, the polypeptide sequences 5'-ACDEFG-3' and 5'-ACDHIK-3' (SEQ ID NOS:9 and 10, respectively) share 50% homology and the nucleotide sequences 5'-CAATCG-3' and 5'-CAAGAC-3' share 50% homology.

In summary, the invention should be construed to include nucleic acids comprising AtPCS1 or AtPCS2, or sharing at least 15% homology with SEQ ID NO: 1, SEQ ID NO: 3, SEQ ID NO: 5, SEQ ID NO: 7, or SEQ ID NO: 9, and any fragments thereof, which encode phytochelatin synthase biological activity, and polypeptides comprising AtPCS1, AtPCS2, TaPCS1, SpPCS, and CePCS, or sharing at least 15% homology with SEQ ID NO: 2, SEQ ID NO; 4, SEQ ID NO: 6, SEQ ID NO: 8, or SEQ ID NO: 10, and any fragments thereof, which comprise phytochelatin synthase biological activity.

The invention further features an isolated a nucleic acid which is antisense in orientation to a portion or all of a nucleic acid encoding a phytochelatin synthase comprising AtPCS1, AtPCS2, TaPCS1, SpPCS, CePCS, or sharing at least 15% homology with at least one of SEQ ID NO: 1, SEQ ID NO: 3, SEQ ID NO: 5, SEQ ID NO: 7, or SEQ ID NO: 9, and any fragments thereof, wherein the antisense nucleic acid, or fragment thereof, is capable of inhibiting expression of the nucleic acid encoding a phytochelatin synthase when introduced into cells comprising the nucleic acid encoding a phytochelatin synthase.

"Antisense" refers particularly to the nucleic acid sequence of the non-coding strand of a double stranded DNA molecule encoding a protein, or to a sequence which is substantially homologous to the non-coding strand. As defined herein, an antisense sequence is complementary to the sequence of a double stranded DNA molecule encoding a protein. It is not necessary that the antisense sequence be complementary solely to the coding portion of the coding strand of the DNA molecule. The antisense sequence may be complementary to regulatory sequences specified on the coding strand of a DNA molecule encoding a protein, which regulatory sequences control expression of the coding sequences.

"Complementary," as used herein, refers to the subunit sequence complementarity between two nucleic acids, e.g., two nucleic acid molecules. When a nucleotide position in both of the molecules is occupied by nucleotides normally capable of base pairing with each other, then the nucleic acids are considered to be complementary to each other at this position. Thus, two nucleic acids are complementary to each other when a substantial number (at least 50%) of corresponding positions in each of the molecules are occupied by nucleotides which normally base pair with each other (e.g., A:T and G:C nucleotide pairs).

The present invention also provides for analogs of proteins or peptides encoded by AtPCS1, AtPCS2, TaPCS1, SPPCS, or CePCS. Analogs can differ from naturally occurring proteins or peptides by conservative amino acid sequence differences or by modifications which do not affect sequence, or by both.

For example, conservative amino acid changes may be made, which although they alter the primary sequence of the protein or peptide, do not normally alter its function. Conservative amino acid substitutions typically include substitutions within the following groups:

glycine, alanine;

valine, isoleucine, leucine;

aspartic acid, glutamic acid;

asparagine, glutamine;

serine, threonine;

lysine, arginine;

phenylalanine, tyrosine.

Modifications (which do not normally alter primary sequence) include in vivo, or in vitro chemical derivatization of polypeptides, e.g, acetylation, or carboxylation. Also included are modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine.

Also included are polypeptides which have been modified using ordinary molecular biological techniques so as to improve their resistance to proteolytic degradation or to optimize solubility properties or to render them more suitable as a therapeutic agent. Analogs of such polypeptides include those containing residues other than naturally occurring L-amino acids, e.g., D-amino acids or non-naturally occurring synthetic amino acids. The peptides of the invention are not limited to products of any of the specific exemplary processes listed herein.

The invention further includes a transgenic plant comprising an isolated nucleic acid encoding a plant phytochelatin synthase, or a fragment thereof, capable of producing PCs. The transgenic plant of the invention may comprise a transgene encoding a plant phytochelatin synthase polypeptide, or a fragment thereof, or it may comprise a transgene encoding a phytochelatin synthase from a non-plant species which shares at least ΔSpPCS homology with the plant nucleic acid and/or protein, which heterologous transgene is expressed in the plant to yield a biologically active phytochelatin synthase protein product. By way of example, there is provided herein in the experimental examples section a yeast transformant comprising an Arabidopsis phytochelatin synthase AtPCS1 transgene, which when the transgene is expressed in the yeast cell, confers upon the cell the ability to grow on media containing concentrations of heavy metal (cadmium) that would otherwise prevent growth of nontransgenic yeast. Similarly, the experimental examples disclose a yeast transformant expressing the phytochelatin synthase transgene, (i)TaPCS1, isolated from wheat which yeast demonstrated increased tolerance to $Cd^{2+}$, increased accumulation of this heavy metal even in low levels of $Cd^{2+}$, and induced the increased biosynthesis of PCs in the yeast transformant. Therefore, the present invention teaches that expression of a nucleic acid encoding a PC synthase from another species confers PC synthase biological activity upon another organism.

By "transgenic plant" as used herein, is meant a plant, the cells, the seeds and the progeny of which comprise an isolated nucleic acid inserted therein, which isolated nucleic acid has been manipulated to be inserted into the cells of the plant by recombinant DNA technology. The manipulated isolated nucleic acid is designated as a "transgene."

If heavy metal detoxification is limited by the rate of PC biosynthesis, transgenic plants with increased AtPCS1, AtPCS2, TaPCS1, SpPCS, and/or CePCS expression would be expected to be more resistant to the toxic effects of heavy metals. By the same token, if vacuolar heavy metal sequestration is limited by the rate of PC biosynthesis, transgenic plants with increased AtPCS1, AtPCS2, TaPCS1, SpPCS, and/or CePCS expression would be expected to be capable of accumulating higher vacuolar heavy metal levels than otherwise identical, non-transgenic plants. The former property permits the sustained growth of transgenic plants in the presence of heavy metal concentrations that would retard the growth of plants exhibiting normal levels of PC synthase expression. The latter property confers on transgenic plants the capacity for vacuolar heavy metal hyperaccumulation.

"Heavy metal resistance," as the term is used herein, means that the organism is able to tolerate a higher intracellular level of a heavy metal than an otherwise identical organism which is not heavy metal resistant. Such ability to tolerate may be demonstrated by the ability of the organism to survive and even grow and/or divide in the presence of heavy metal which would kill and or cause an otherwise identical but non-resistant organism to not grow or divide.

In one embodiment, yeast transformants were heavy metal resistant to higher concentrations of arsenate, arsenite, copper, or mercury compared with otherwise identical non-transformant yeast of the same strain. However, the present invention should not be limited to these heavy metals or to yeast transformants. Rather, the invention should be construed to encompass any living organism and includes resistance to any heavy metal which may be encountered by the organism.

Further, yeast heavy metal transformants were able to grow and divide in culture in the presence of heavy metal salts as measured by the amount of heavy metal required to cause a 50% attenuation of growth as measured by increased optical density of the liquid growth culture. However, the present invention is not limited to measuring the toxic effect(s) of heavy metal exposure on cell growth and division in any particular manner. Rather, the invention should be interpreted to include any method to measure the growth and/or survival of a living organism before, during or after heavy metal exposure, compared with an otherwise identical organism that is not resistant to heavy metal. Other heavy metal assays include, but are not limited to, measurements of $LD_{50}$, dry or fresh weight, tissue chlorosis/necrosis, $CO_2$ fixation, $O_2$ consumption, $CO_2$ evolution, the formation of activated oxygen species, cell or tissue turgidity, and the like.

Increased resistance to heavy metals has application in plant technology and plant growth in habitats polluted with xenobiotics. Since the plant vacuole frequently constitutes 40–90% of the total intracellular volume and since PCs mediate the uptake of heavy metals into this compartment, the potential for hyperaccumulation on a tissue weight basis as a result of increased production of PCs by phytochelatin synthase is great. Hyperaccumulators may then be used for the fixation/sequestration of heavy metals and their removal from soils.

The generation of transgenic plants comprising an isolated nucleic acid comprising the nucleic or amino acid sequence of a plant phytochelatin synthase, or a fragment thereof, may be accomplished by transformation of the plant with a plasmid encoding the desired nucleic acid sequence. Suitable vectors include, but are not limited to, disarmed Agrobacterium tumor-inducing (Ti) plasmids containing a sense or antisense strand placed under the control of the strong constitutive CaMV 35S promoter or under the control of an inducible promoter (Lagrimini et al., 1990, supra; van der Krol et al., 1988, Gene 72:45–50). Methods for the generation of such constructs, plant transformation and plant regeneration are well known in the art once the sequence of the desired gene is known and are described, for example, in Ausubel et al. (1993, Current Protocols in Molecular Biology, Greene and Wiley, New York).

Suitable vector and plant combinations will be readily apparent to those of skill in the art and can be found, for example, in Maliga et al. (1994, Methods in Plant Molecular Biology: A Laboratory Manual, Cold Spring Harbor, N.Y.).

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like.

"Expression vector" refers to a vector comprising a recombinant polynucleotide comprising expression control sequences operatively linked to a nucleotide sequence to be expressed. An expression vector comprises-sufficient cis-acting elements for expression; other elements for expression can be supplied by the host cell or in an in vitro expression system. Expression vectors include all those known in the art, such as cosmids, plasmids (e.g., naked or contained in liposomes) and viruses that incorporate the recombinant polynucleotide.

Transformation of plants may be accomplished using the Agrobacterium-mediated leaf disc transformation method described by Horsch et al. (1988, Leaf Disc Transformation, Plant Molecular Biology Manual A5: 1).

A number of procedures may be used to assess whether the transgenic plant comprises the desired nucleic acid. For example, genomic DNA obtained from the cells of the transgenic plant may be analyzed by Southern blot hybridization or by PCR to determine the length and orientation of any inserted, transgenic nucleic acid present therein. Northern blot hybridization analysis or PCR may be used to characterize mRNA transcribed in cells of the transgenic plant. In situations where it is expected that the cells of the transgenic plant express phytochelatin synthase polypeptide, or a fragment thereof, Western blot analysis may be used to identify and characterize polypeptides so expressed using antibody raised against the phytochelatin synthase, or fragments thereof. In situations where phytochelatin synthase polypeptide is expressed in a catalytically active form, PC biosynthesis assays may be used to identify and characterize the enzyme molecules so expressed. The procedures for performing such analyses are well known in the art and are described, for example, in Sambrook et al. (supra).

The transgenic plants of the invention are useful for the manipulation of heavy metal detoxification. For example, a transgenic plant encoding an AtPCS1 or an AtPCS2 is useful for heavy metal detoxification when grown on soil containing heavy metals. Such plants are capable of removing heavy metals from the soil thereby generating soil which has reduced levels of compounds that are detrimental to the overall health of the environment.

Accordingly, the invention includes a method of removing heavy metals from soil comprising generating a transgenic plant having a transgene encoding a phytochelatin synthase and planting the plant or the seeds of the plant in the soil wherein heavy metals in the soil are hyperaccumulated/sequestered within the plant during growth of the plant in the soil. The plants are then harvested from the soil by standard agricultural methods well-known in the art or by methods to be developed in the future for harvesting of plants and/or methods developed specifically for phytoremediation.

When the levels of heavy metals in the soil have been sufficiently reduced, the transgenic plant may be removed from the soil and destroyed or discarded in an environmentally safe manner. For example, the harvested plants can be reduced in volume and/or weight by thermal, microbial, physical or chemical means to decrease handling, processing and potential subsequent land filling costs (Cunningham et al., 1996, Plant Physiol. 110:715–719). In the case of valuable metals, subsequent smelting and recovery of the metal may be cost-effective (Raskin, 1996, Proc. Natl. Acad. Sci. USA 93:3164–3166).

This technique of remediating soil is more efficient, less expensive and easier than most chemical or physical methods. The estimated costs of remediation are as follows: U.S. $10–100 per cubic meter of soil for removal of volatile or water soluble pollutants by in situ remediation using plants; U.S. $60–300 per cubic meter of soil for landfill or low temperature thermal treatment remediation of soil contaminated with the same compounds; and, U.S. $200–700 per cubic meter of soil for remediation of soil contaminated with materials requiring special landfilling arrangements or high temperature thermal treatment (Cunningham et al., 1995, Trends Biotechnol. 13:393–397).

Preferably, the transgene in the transgenic plant of the invention is AtPCS1, AtPCS2, or genes encoding fragments or analogs of AtPCS1, AtPCS2, or the transgene is a nucleic acid which is at least about 15% homologous to AtPCS1, (SEQ ID NO: 1) AtPCS2 (SEQ ID NO: 3), TaPCS1 (SEQ ID NO: 5), SpPCS (SEQ ID NO: 7), and CePCS (SEQ ID NO: 9).

As used herein, the term "transgene" means an exogenous nucleic acid sequence comprising a nucleic acid which encodes a promoter/regulatory sequence operably linked to nucleic acid which encodes an amino acid sequence, which exogenous nucleic acid is-encoded by a transgenic organism.

By describing two polynucleotides as "operably linked" is meant that a single-stranded or double-stranded nucleic acid moiety comprises the two polynucleotides arranged within the nucleic acid moiety in such a manner that at least one of the two polynucleotides is able to exert a physiological effect by which it is characterized upon the other. By way of example, a promoter operably linked to the coding region of a gene is able to promote transcription of the coding region.

As used herein, the term "promoter/regulatory sequence" means a nucleic acid sequence which is required for expression of a gene product operably linked to the promoter/regulator sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue-specific manner.

One skilled in the art, based upon the disclosure provided herein, would appreciate that expression of PC synthase in certain tissues, such as roots, may minimize the level of heavy metals present in harvestable tissues of the plant (e.g., leaves and fruits). Further, for purposes of bioremediation of contaminated groundwaters, expression of PC synthases in aerial tissues would increase the accumulation of heavy metals in those tissues. Additionally, the selective expression of PC synthase in plant roots would enhance the ability to the plants to remove toxic heavy metals from contaminated groundwaters in a process termed "rhizofiltration." The plants containing the heavy metals could then be easily harvested from such waters thereby removing the heavy metal contaminants from groundwaters.

By "groundwater," as the term is used herein, is meant any water source, either natural or man-made.

The types of plants which are suitable for use in this method of the invention include, but are not limited to, high yield crop species for which cultivation practices have already been perfected, or engineered endemic species that thrive in the area to be remediated.

In certain situations, it may be necessary to prevent the removal of substances such as xenobiotic toxins and heavy metals from the soil or groundwater. In such situations, transgenic plants are generated comprising a transgene comprising an AtPCS1, AtPCS2, TaPCS1, SpPCS, or CePCS sequence, or a sequence having at least 15% homology with at least one of SEQ ID NO: 1, SEQ ID NO: 3, SEQ ID NO: 5, SEQ ID NO: 7, and SEQ ID NO: 9, or a fragment thereof, which is in the antisense orientation with respect to transcription. Such transgenes therefore serve to inhibit the function of AtPCS1 , AtPCS2, TaPCS1, SpPCS, or CePCS expressed in the plants thereby preventing removal of heavy metals from the soil and/or groundwater.

One skilled in the art will appreciate that one way to decrease the levels of a PCS protein in a cell is to inhibit expression of the PCS nucleic acid encoding such protein. Expression of PC synthase protein may be inhibited using, for example, antisense molecules, ribozymes, virus-induced genetic suppression, and co-suppression.

Antisense molecules and their use for inhibiting gene expression are well known in the art (see, e.g., Cohen, 1989, In: Oligodeoxyribonucleotides, Antisense Inhibitors of Gene Expression, CRC Press). Antisense nucleic acids are DNA or RNA molecules that are complementary, as that term is defined elsewhere herein, to at least a portion of a specific mRNA molecule (Weintraub, 1990, Scientific American 262:40). In the cell, antisense nucleic acids hybridize to the corresponding mRNA, forming a double-stranded molecule thereby inhibiting the translation of genes.

The use of antisense methods to inhibit the translation of genes is known in the art, and is described, for example, in Marcus-Sakura, 1988, Anal. Biochem. 172:289. Such antisense molecules may be provided to the cell via genetic expression using DNA encoding the antisense molecule as taught by Inoue, 1993, U.S. Pat. No. 5,190,931 (incorporated by reference herein in its entirety).

Alternatively, antisense molecules of the invention may be made synthetically and then provided to the cell. Antisense oligomers of about 15 nucleotides are preferred, since they are easily synthesized and introduced into a target PC synthase-producing cell. Synthetic antisense molecules contemplated by the invention include oligonucleotide derivatives known in the art which have improved biological activity compared to unmodified oligonucleotides (see Cohen, supra; Tullis, 1991, U.S. Pat. No. 5,023,243, incorporated by reference herein in its entirety).

Ribozymes and their use for inhibiting gene expression are also well known in the art (see, e.g:, Cech et al., 1992, J. Biol. Chem. 267:17479–17482; Hampel et al., 1989, Biochemistry 28:4929–4933; Eckstein et al., International Publication No. WO 92/07065; Altman et al., U.S. Pat. No. 5,168,053, incorporated by reference herein in its entirety). Ribozymes are RNA molecules possessing the ability to specifically cleave other single-stranded RNA in a manner analogous to DNA restriction endonucleases. Through the modification of nucleotide sequences encoding these RNAs, molecules can be engineered to recognize specific nucleotide sequences in an RNA molecule and cleave it (Cech, 1988, J. Amer. Med. Assn. 260:3030). A major advantage of this approach is that, because they are sequence-specific, only mRNAs with particular sequences are inactivated.

There are two basic types of ribozymes, namely, tetrahymena-type (Hasselhoff, 1988,.Nature 334:585) and hammerhead-type. Tetrahymena-type ribozymes recognize sequences which are four bases in length, while hammerhead-type ribozymes recognize base sequences 11-18 bases in length. The longer the sequence, the greater the likelihood that the sequence will occur exclusively in the target mRNA species. Consequently, hammerhead-type ribozymes are preferable to tetrahymena-type ribozymes for inactivating specific mRNA species, and 18-base recognition sequences are preferable to shorter recognition sequences which may occur randomly within various unrelated mRNA molecules.

Ribozymes useful for inhibiting the expression of phytochelatin synthases may be designed by incorporating target sequences into the basic ribozyme structure which are complementary to the mRNA sequence of the phytochelatin synthase encoded by AtPCS1, AtPCS2, TaPCS1, SpPCS, or CePCS, or having at least about 15% homology to SEQ ID NO: 1, SEQ ID NO: 3, SEQ ID NO: 5, SEQ ID NO: 7, or SEQ ID NO: 9. Ribozymes targeting phytochelatin synthase may be synthesized using commercially available reagents (Applied Biosystems, Inc., Foster City, Calif.) or they may be genetically expressed from DNA encoding them.

Another approach for inhibiting expression of the PC synthase of interest may be accomplished using virus-induced gene silencing (VIGS) as described by Baulcombe (1999, Curr. Opinion Plant Biol. 2:109–113). That is, portion (s) of an exon is cloned into an appropriate virus vector which, when expressed in the plant tissue, cause the decreased expression of the nucleic acid homologous to the cloned exon. Further, gene expression may be inhibited in plants using co-suppression methods (Kral et al., 1990, Plant Cell 2:279–289; Napoli et al., 1990, Plant Cell. 2:291–299). One skilled in the art would appreciate, based on the disclosure provided herein, that the particular method used to inhibit expression of the PCS of interest may vary depending on the tissue and/or plant and/or the particular PCS gene whose expression is the target of regulation.

AtPCS1, AtPCS2, TAPCS1, SpPCS, and CePCS antisense sequences and/or ribozymes homologous to these PCS sequences, and/or VIGS using sequences homologous to these sequences, has application in the manipulation of plant/food diminution of heavy metal accumulation by crop species. For example, ingestion by animals or humans of low heavy metal crops will likely contribute to an improvement in the overall health of animals and humans.

Accordingly, the invention includes a method of preventing the removal of heavy metals from soil comprising generating a transgenic plant having a transgene comprising a PCS sequence which is in the antisense orientation with respect to transcription or a ribozyme or a VIGS construct and/or a co-suppression construct and planting the plant or the seeds of the plant in the soil, wherein removal of heavy metals from the soil is prevented during growth of the plant in the soil.

The antisense, ribozyme, VIGS, and/or co-suppression sequences which are useful for the generation of transgenic plants having antisense, ribozyme, VIGS, or co-suppression PCS sequences are those which will inhibit expression of a resident PCS gene in the plant.

The types of plants which are suitable for use in this method of the invention using antisense, ribozyme, VIGS or co-suppression sequences include, but are not limited to, crops for which decreased heavy metal accumulation is desirable.

The invention further includes an isolated nucleic acid encoding a phytochelatin synthase covalently linked to a reporter nucleic acid. The procedures for the generation of a isolated nucleic acid encoding a phytochelatin synthase and a reporter nucleic acid are well know in the art once the sequence of the nucleic acid encoding phytochelatin synthase is known, and such techniques are described, for example, in Sambrook et al. (supra). Suitable vectors include, but are not limited to, yeast-*E. coli* shuttle vectors, disarmed Agrobacterium tumor-inducing (Ti) plasmids (e.g., pBIN19) (Lagrimini et al., 1990, Plant Cell 2:7–18; Bevan, 1984, Nuci. Acids Res. 12:8711–8721).

A "reporter nucleic acid" as used herein, is one which when transcribed or translated in a cell, results in the production of a detectable product in the cell. Typically, the level of expression of the product in the cell is proportional to the activity of the promoter sequence which drives expression of the reporter nucleic acid and the nucleic acid encoding the plant phytochelatin synthase linked to the reporter nucleic acid. Therefore, expression of the reporter nucleic acid indicates the level of expression of the plant phytochelatin synthase and may also be used to determine the cellular location of the phytochelatin synthase nucleic acid and/or polypeptide expressed therefrom and linked to the reporter sequence.

By describing two nucleic acid sequences as "covalently linked" as used herein, is meant that a single-stranded or double-stranded nucleic acid moiety comprises each of the two nucleic acid sequences and that the two sequences are arranged within the nucleic acid moiety in such a manner that the two sequences are transcribed and/or translated to produce a chimeric nucleic acid and/or polypeptide.

Suitable reporter nucleic acids encode, for example, human influenza virus hemagglutinin (HA) epitope, the octapeptide FLAG epitope, β-glucuronidase (GUS) and green fluorescent protein (QFP), or luciferase (LUC), although any reporter nucleic acid capable of expression and detection in plant cells which are either known or heretofore unknown, may be linked to the plant phytochelatin synthase nucleic acids of the invention.

The invention further includes a transgenic plant comprising an isolated nucleic acid comprising a phytochelatin synthase comprising AtPCS1, AtPCS2, TaPCS1, SpPCS, or CePCS, or a nucleic acid sharing at least 15% homology with SEQ ID NO: 1, SEQ ID NO: 3, SEQ ID NO: 5, SEQ ID NO: 7, and/or SEQ ID NO: 9, linked to a reporter nucleic acid.

The basic principle of reporter gene analysis is illustrated by, but not limited to, the GUS method. Briefly, to assess PCS expression in a plant cell, whether the cell is contained within a plant or is separated from a plant, a plasmid may be generated which comprises the GUS reporter gene fused to a PCS promoter sequence, or to a tissue-specific promoter sequence. For example, the appropriate restriction fragment is subcloned into the GUS expression vector pBI101.3 (Jefferson et al., 1987, EMBO J., 6:3901–3907). After confirming the correct reading frame by sequencing, Agrobacterium or any other suitable vector, is transformed with the expression construct and is then used to used to transform the plant, or the cells thereof (Valvekens et al., 1988, Proc. Natl. Acad. Sci. U.S.A. 85:5536–5540).

Expression of GUS may be localized histochemically by staining with 5-bromo-4-chloro-3-indoyl β-D-glucuronide (X-Gluc; Jefferson et al., supra). Sections are obtained from the plant, they are incubated in X-Gluc, cleared by boiling in ethanol and are examined under the microscope. To eliminate or enumerate complications arising from the transfer of GUS reaction product between cells, the distribution of GUS expression is then further examined both immunologically and biochemically. β-glucuronidase protein is assessed using standard dot-blotting and immunolocalization techniques (Harlow et. al., 1988, Antibodies: A Laboratory Manual, Cold Spring Harbor Laboratory, NY) using rabbit anti-β-glucuronidase serum (ClonTech, Inc., Palo Alto, Calif.). Direct estimates of GUS activity are be made fluorimetrically using 4-methyl-umbelliferyl glucuronide as substrate (Jefferson et al., supra) after dissection and extraction of explants.

The present invention also includes a method of biosynthesizing a phytochelatin. The method comprises contacting an isolated phytochelatin synthase with a sufficient amount of glutathione, or a glutathione-related thiol peptide, under conditions which permit biosynthesis of phytochelatins from glutathione or other related thiol peptide.

By the term "sufficient amount," as that term is used herein, is meant an amount of glutathione, or glutathione-related thiol peptide, which allows a detectable amount of PC biosynthesis to occur under conditions which typically permit such biosynthesis.

Conditions which permit biosynthesis of phytochelatins from glutathione or other related thiol peptide are the chemical and biological parameters required for the transfer of a γ-glutamylcysteine unit from or onto a peptide. Such parameters, for example, are set forth in Grill et al. (1989, Proc. Natl. Acad. Sci. U.S.A. 89:6838–6842), and they include, but are not limited to, the presence of about 3.3 mM GSH, 10 mM 2-ME, and 200 mM Tris-HCl buffer (pH 8.0), in the absence or presence of $CdCl_2$. However, the present invention should not be construed to be limited to these or any other specific conditions for PC biosynthesis. Rather, the present invention should be construed to encompass any conditions under which a detectable level of enzymatic transfer of a γ-glutamylcysteine unit from a substrate onto another -I molecule may take place in the presence of any required ions, substrates and/or cofactors.

By "glutathione-related thiol peptide," as the term is used herein, is meant any peptide which may be used by a phytochelatin synthase to transfer a γ-glutamylcysteine unit from that peptide onto another moiety or onto which a phytochelatin synthase may transfer a γ-glutamylcysteine unit from another source. Such GSH-related thiol peptides include, but are not limited to, homoglutathione, $PC_2$, $PC_3$, and $PC_4$.

"Biosynthesis," as the term is used herein, means any bona fide catalytic reaction mediated by an enzyme to produce a compound. In one embodiment, the biosynthesis is the enzymatic reaction whereby an isolated phytochelatin synthase produces a phytochelatin by transfer of a γ-glutamylcysteine unit from GSH to another related thiol peptide. However, the present invention encompasses PC biosynthesis performed in vitro in an appropriate buffer system in the presence of purified PC synthase, GSH, or any other related thiol peptide source of γ-glutamylcysteine units, and a concentration of heavy metal ion sufficient to activate PC synthase-mediated PC biosynthesis as disclosed elsewhere herein. Purified PC synthase may be employed at a concentration ranging from about 0.1 μg to about 0.1 mg/ml, GSH {or, for example, γ-glutamylcysteine, PC2, PC3, or PC4, or homo-GSH, hydroxymethyl-GSH (γ-Glu-Cys-Ser), or γ-glutamylcysteinylglutamic acid (Zenk et al., supra)} at a concentration ranging from about 0.1 μM to about 50 mM, and heavy metal (e.g., Cd2+, Hg2+, Pb2+, As3+, Cu2+, Ni2+, or Zn2+) at a concentration ranging from about 0.1 to about 500 μM. Thus, PC biosynthesis requires at least a PC synthase (e.g., AtPCS1, AtPCS2, TaPCS1, SpPCS, or CePCS), GSH (as γ-glutamylcysteine donor or acceptor), and a heavy metal activator. The invention should not be construed to be limited to biosynthesis of any particular phytochelatin or to reactions where the γ-glutamylcysteine unit is derived from GSH; rather, the present invention should be construed to encompass the synthesis of any $(γ-Glu-Cys)_n$ polymer mediated by a PC synthase molecule.

Further, the present invention is intended to encompass biosynthesis of PCs whether in vitro using PC synthase from biological extracts as well as biosynthesis performed in vivo. In one embodiment, the biosynthesis is performed by heterologous expression of A. thaliana PC synthase 1 in yeast cells. In another embodiment, the biosynthesis is performed by heterologous expression of either a wheat PC synthase (TaPCS1) or a yeast PC synthase (SpPCS) in a S. cerevisiae yeast cell. In yet another embodiment, the biosynthesis is performed in vitro using a purified recombinant SpPCS protein. The present invention encompasses PC biosynthesis performed in vitro in an appropriate buffer system in the presence of a purified PC synthase, GSH, or any other related thiol peptide source of γ-glutamylcysteine units, and an amount of $CdCl_2$ sufficient to elicit PC synthase catalyzed biosynthesis of PCs as disclosed herein.

In one embodiment, the isolated phytochelatin synthase protein is AtPCS1. However, the present invention should not be construed to be limited to solely AtPCS1. Rather, the invention should be construed to include other phytochelatin synthases wherein the PC synthases share at least about 15% sequence homology at either the nucleic or amino acid sequence level with AtPCS1 (i.e., SEQ ID NO: 1 or SEQ ID NO: 2, respectively), including, but not limited to, AtPCS2 (SEQ ID NO: 3 and SEQ ID NO: 4), TaPCS1 (SEQ ID NO: 5 and SEQ ID NO: 6), SpPCS (SEQ ID NO: 7 and SEQ ID NO: 8), and CePCS (SEQ ID NO: 9 and SEQ ID NO: 10).

The invention also includes a method of transferring a γ-glutamylcysteine unit from one thiol peptide to another, said method comprising contacting an isolated phytochelatin synthase with a glutathione, or a related thiol peptide, under conditions which permit transfer of said γ-glutamylcysteine unit from one thiol peptide to another, thereby transferring a γ-glutamylcysteine unit from one thiol peptide to another.

The invention includes a method of decreasing the level of a heavy metal in a harvestable portion of a plant. The method comprises expressing a nucleic acid encoding a phytochelatin synthase in a non-harvestable portion of a plant. As discussed previously elsewhere herein, tissue-specific expression of a nucleic acid encoding PCS may be performed using a tissue-specific promoter sequence covalently linked to the nucleic acid encoding PCS. Such tissue-specific promoters are well-known in the art.

Expression of a phytochelatin synthase in the non-harvestable portion of the plant causes the heavy metal to be accumulated therein, thereby reducing the amount of heavy metal in the harvestable portion of the plant. Expression of a phytochelatin synthase in the non-harvestable portion of the plant may be accomplished by operably linking nucleic acid encoding PCS to a promoter, either a constitutive or a tissue-specific promoter, and introducing the nucleic acid so operably linked, into the non-harvestable portion of the plant. As described previously elsewhere herein, transgenic plants may be produced comprising a nucleic acid encoding a phytochelatin synthase under the control of an appropriate promoter thereby causing the PC synthase to be selectively expressed in the non-harvestable portion of the transgenic plant.

Thus, one skilled in the art, based upon the disclosure provided herein, would appreciate that expression of PCS in a non-harvestable portion of the plant results in hyperaccumulation of heavy metal in that portion of the plant thereby decreasing the level of a heavy metal elsewhere in the plant including a decrease in the level of heavy metal in the harvestable portion of the plant.

In one aspect, the level of heavy metal in the harvestable portion of the plant would be decreased further by inhibiting the expression of any endogenous phytochelatin synthase in the harvestable portion of the plant. As discussed previously elsewhere herein, methods for specifically inhibiting the expression of PCS in a plant are well-known in the art and include, but are not limited to, the use of antisense molecules, ribozymes, VIGS, and co-suppression techniques. These methods allow the tissue-specific inhibition of PCS in a harvestable portion of a plant. Thus, the level of expression of a nucleic acid encoding a phytochelatin synthase is increased in a non-harvestable portion of a plant causing hyperaccumulation of heavy metal in such portion while, at the same time, the expression of phytochelatin synthase in a harvestable portion of the same plant is inhibited causing an even. further reduction in the level of heavy metal present in the harvestable portion of the plant.

The invention also includes a method of removing a heavy metal from groundwater. The method comprises growing in the groundwater a transgenic plant comprising an isolated nucleic acid encoding a phytochelatin synthase. The transgenic plant therefore accumulates heavy metals obtained from the groundwater such that when the plant is harvested from the groundwater the heavy metals are removed with the plant thereby removing heavy metal from the groundwater.

The invention is further described in detail by reference to the following experimental examples. These examples. are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

EXAMPLE 1
Phytochelatin Synthases from Arabidopsis

The experiments presented in this example may be summarized as follows.

Phytochelatins, a class of posttranslationally synthesized proteins, play a pivotal role in heavy metal, primarily $Cd^{2+}$, tolerance in plants and fungi. PCs chelate heavy metals thereby decreasing their free concentrations in samples. Derived from glutathione and related thiols by the action of γ-glutamylcysteine dipeptidyl transpeptidases (i.e., phytochelatin syntheses; EC 2.3.2.15), phytochelatins consist of repeating units of γ-glutamylcysteine followed by a C-terminal Gly, Ser or β-Ala {poly-(γ-Glu-Cys)$_n$-Xaa}. The data disclosed herein demonstrate, for the first time, the suppression cloning of a novel cDNA (AtPCS1) from *Arabidopsis thaliana* encoding a 55 kDa soluble protein that enhances heavy metal tolerance and promotes $Cd^{2+}$-elicited phytochelatin accumulation when expressed in *Saccharomyces cerevisiae*. Based on these properties, the data disclosed herein demonstrate that AtPCS1 encodes the enzyme phytochelatin synthase. In addition, the data disclosed herein demonstrated the sufficiency of immunoaffinity-purified epitope-tagged AtPCS1 polypeptide for high rates of $Cd^{2+}$-activated phytochelatin synthesis from glutathione in vitro, further supporting that AtPCS1 encodes the enzyme phytochelatin synthase.

The Materials and Methods used in the experiments presented in this example are now described.

Yeast strains and plant materials

The yeast strains used in the experiments disclosed herein were as follows: yap1Δ mutant SM12 (MATαleu2-3,-112 ura3-52 his3-Δ200 trp1-Δ901 lys2-801 suc2-Δ9 Mel⁻ yap1-Δ1::HIS3; Wemmie et al., 1994, J. Biol. Chem. 269:14690–14697); the ycf1Δ mutants DTY167 (MATαura3-52 leu2-3,-112 his-Δ200 trp1-Δ901 lys2-801 suc2-Δ9 ycf1::hisG; Li et al., 1996, J. Biol. Chem. 271:6509–6517) and DTY168 (MATαura3-52 leu2-3,-112 his6ycf1::hisG; Szczypka et al., 1994, J. Biol. Chem. 269:22853–22857); the pep5 Δ mutant DTY214 (MATαura3-52 leu2-3,-112 his3-Δ200 trp1-Δ901 lys2-801 suc-Δ9pep5::LEU2); and the cup1Δ mutant DTY4 (MATαura3-52 leu2-3,-112 trp1-1 gal1 his-cup1Δ::URA3; Hamer et al., 1985, Science 228:685–690). *A. thaliana*, cultivar Columbia, was the source of the RNA used for construction of the pFL61 cDNA library as described by Minet et al. (1992, Plant J. 2:417–422) and Northern blot analyses, and the genomic DNA used for the Southern blot analyses.

Isolation of AtPCS1

To identify plant genes which are capable of suppressing $Cd^{2+}$-hypersensitivity, *S. cerevisiae* yap1Δ strain SM12 was transformed with an Arabidopsis cDNA library constructed in the yeast-*Escherichia coli* shuttle vector pFL61 (Minet et al., 1992, Plant J. 2:417–422). Stable $Cd^{2+}$-tolerant, Ura⁺ transformants were selected by first plating the SM12 transformants on synthetic complete-Ura medium containing 100 μM CdCl$_2$ followed by replication to medium containing 200 μM CdCl$_2$. The pFL61 plasmids from all 105 $Cd^{2+}$-tolerant SM12 transformants identified in this step were rescued (Strathern and Higgins, 1991 Methods Enzymol. 194:319–329), used to transform *S cerevisiae* ycf1Δ strain DTY168, and $Cd^{2+}$-tolerant transformants were selected by plating on AHC medium (Kim et al., 1994, Proc. Natl. Acad. Sci. U.S.A. 91:6128–6132) containing 200 μM $CdCl_2$. Of the 104 pFL61 clones found to suppress the $Cd^{2+}$-hypersensitivity of strains SM12 and DTY168, only two, whose 1.7 kb inserts were determined to be identical, conferred a particularly high level of $Cd^{2+}$ tolerance. One of these, termed pFL61-AtPCS1, was analyzed functionally.

Heterologous expression of FLAG-tagged AtPCS1

In order to constitutively express immunoreactive protein in *S. cerevisiae,* the AtPCS1 cDNA insert of pFL61-AtPCS1 was first subcloned into the pYES3 vector, a derivative of pYES2 (Invitrogen, Carlsbad, Calif.), in which the galactose-inducible yeast GAL1 gene promoter was replaced by the constitutive 3-phosphoglycerate kinase (PGK) promoter (GTTACATGCGTACACGCGTCTG; SEQ ID NO: 11; Lu et al., 1997, Proc. Natl. Acad. Sci. U.S.A. 94:8243–8247), and engineered to encode AtPCS1 fused to a C-terminal FLAG (DYKDDDDK; SEQ ID NO: 12) epitope tag as described by the manufacturer's instructions (International Biotechnologies, Inc., New Haven, Conn.), which yielded a stable translation product. More specifically, the construct was engineered to contain the 24 bp DNA sequence encoding the FLAG epitope and a SmaI restriction site for directional cloning (i.e. ,AAACAGCTGCTTGTCATCGTCGTCCTTGTAGTCCC-CGGGATAGGCAGG AGC; the FLAG coding sequence underlined; SEQ ID NO: 13). The FLAG octapeptide sequence on the AtPCS1-FLAG fusion protein was detected using known immunohistochemical methods which involve use of an Anti-FLAG antibody such as, for example, monoclonal antibodies M2 or M5, as described by the manufacturer's instructions (International Biotechnologies, Inc., New Haven, Conn.).

After the fidelity of the resulting construct, pYES3-AtPCS1::FLAG, was confirmed by sequencing, *S. cerevisiae* ycf1Δ strain DTY167 was transformed with this construct or an empty vector lacking the AtPCS1::FLAG insert using the LiOAc/PEG method described by Giest and Schiestl (1991,Yeast 7:253–263) and the transformants were selected for uracil prototrophy by plating on ammonia/hydrolyzed casein (AHC) medium (0.17% (w/v) yeast nitrogen base without amino acids, 0.5% (w/v) ammonium sulfate, 1% (w/v) acid-hydrolyzed casein, 0.02% (w/v) adenine hemisulfate and 2% (w/v) glucose, buffered to pH 5.5 using 50 mM Mes-Tris) with or without tryptophan supplementation (Kim et al., 1994, Proc. Natl. Acad. Sci. USA 91:6128–6132).

Cell fractionation

In order to examine the localization of AtPCS1-FLAG, DTY167/pYES3-AtPCS1::FLAG or control DTY167/pYES3 cells were subjected to cell wall digestion, disruption and fractionation by differential centrifugation. Two-hundred ml volumes of stationary phase cultures were diluted into 1 l of AHC medium containing tryptophan and the cells were grown for 16–18 hours at 30° C. to an $A_{600\,nm}$ of approximately 1.0. The cells were collected by centrifugation and were converted to spheroplasts as described by Lu et al. (1997, Proc. Natl. Acad. Sci. U.S.A. 94:8243–8247). After disruption of the spheroplasts by homogenization in homogenization medium (10 mM Tris-HCl, pH 7.6) containing 1 mM phenylmethylsulfonylfluoride and 1 μg/ml each of leupeptin, pepstatin and aprotinin in a Dounce homogenizer, the crude lysate was cleared by centrifugation at 4,000×g for 10 minutes. After two final centrifugations at 100,000×g for 1 hour, the supernatant (soluble fraction) was frozen and reduced in volume by lyophilization and the pellet (membrane fraction) was resuspended in 1–2 ml of homogenization buffer containing protease inhibitors before freezing in liquid nitrogen and storage at −85° C. For investigations of the PC contents and PC synthesis capacities of the soluble fractions and for purification of AtPCS1-FLAG, the cells were fractionated in an identical manner except that the homogenization medium contained 10 mM 2-ME, 10% (v/v) glycerol, and 50 mM Tris-HCl, pH 8.0, in addition to protease inhibitors.

Purification of AtPCS1-FLAG

AtPCS1-FLAG was purified from the soluble fraction of DTY167/pYES3-AtPCS1-FLAG cells on an anti-FLAG M2 monoclonal antibody affinity gel colunm (Sigma Chemical Co., St. Louis, Mo.) according to the manufacturer's recommendations, except that the wash buffer (Tris-buffered saline, TBS, 150 mM NaCl, 50 mM Tris-HCl, pH 7.4) and the elution buffer (0.1 M glycine-HCl, pH 3.5) both contained 10% (v/v) glycerol.

Equilibrium dialysis of AtPCS1-FLAG

The binding of $Cd^{2+}$ was determined by equilibrium dialysis of a 400–800 μl (160 μg) sample of purified AtPCS1-FLAG against 80 ml volumes of 10 mM Tris-HCl buffer, pH 7.8, containing 0.05 to 20 μM $^{109}CdCl_2$ (specific activity 22 Ci/mol, Amersham Pharmacia Biotech, Piscataway, N.J.) for 12 hours at 4° C. in 2 ml mini-collodion membrane tubes (molecular weight cut-off of 25,000; Schleicher and Schuell, Inc., Keene, N.H.). Protein-bound $^{109}Cd$ was estimated by measuring the radioactivity of the bulk medium outside the dialysis tube and that of the solution within the dialysis tube and determining the increase in $^{109}Cd$ radioactivity consequent on AtPCS1-FLAG. Binding constants and stoichiometries of binding were estimated by nonlinear least squares analysis (Marquardt, 1963, J. Soc. Ind. Appl. Math. 11:431–441) using the Ultrafit nonlinear curve fitting package from BioSoft (Ferguson, Mo.).

Gel filtration FPLC of soluble fractions and purified AtPCS1-FLAG

Analysis of the distribution of $^{109}Cd$ in the soluble fractions extracted from DTY167/pYES3-AtPCS1::FLAG and DTY167/pYES3 cells after growth in media containing $^{109}CdCl_2$ was by FPLC of the extracts on a Superose™6 HR10/30 column (Pharmacia LKB Biotechnology Inc., Piscataway, N.J.). One hundred ml aliquots of stationary phase cultures grown on AHC medium supplemented with glucose and tryptophan were diluted into 500 ml volumes of fresh medium containing 50 μM $^{109}CdCl_2$ (specific activity 2.3 Ci/mol) and the cells were grown at 30° C. for a further 18 hours. Samples of the soluble fractions (1 ml, 1.2–1.8 mg protein) were prepared as described previously elsewhere herein, and the samples were incubated for 30 minutes on ice with 10 mM dithiothreitol (DTT) and the samples were then applied to the Superose-6 column. The column was developed with 50 mM Tris-HCl, pH 7.8, at a flowrate of 0.3 ml/min. Fractions of 0.5 ml were collected and the level of $^{109}Cd$ present in the column fraction was determined by counting aliquots (60 μl) of each fraction in BCS liquid scintillation cocktail (Amersham, Arlington Heights, Ill.). To determine the distribution of AtPCS1-FLAG, aliquots of the column fractions were analyzed by SDS-PAGE and Western blot analysis as described elsewhere herein. Immunoaffinity-purified AtPCS1-FLAG (1 ml, 140–180 μg protein), either before or after equilibrium dialysis against 5 μM $^{109}CdCl_2$ (specific activity 2.3 Ci/mol), was chromatographed under identical conditions.

Measurement of PCs and PC synthase activity

Cellular PC content was estimated by reverse-phase FPLC of the soluble fractions prepared from DTY167/pYES3-AtPCS1::FLAG or DTY167/pYES3 cells after growth in liquid media containing or lacking 50 $\mu$M $CdCl_2$. For reverse-phase FPLC, 1–2 ml volumes of the extracts (2.3–4.6 mg protein) were made 5% (w/v) with 5-sulfosalicylic acid and the samples were centrifuged before loading aliquots (500 $\mu$l) of the supernatant onto a PepRPC HR5/5 HPLC column (Pharmacia LKB Biotechnology Inc., Piscataway, N.J.). The column was developed with a water/0.1% (v/v) phosphoric acid (solvent A)-acetonitrile/0.1% (v/v) phosphoric acid (solvent B) gradient at a flowrate of 0.4 ml/minute. The program parameters were: 0–2 minutes, 0–2% solvent B; 2–5 minutes, 2% solvent B; 5–33 minutes, 2–30% solvent B. Thiols were estimated spectrophotometrically at 412 nm by reacting aliquots (100 $\mu$l) of the column fractions with 0.4 mM 5,5'-dithio-bis(2-nitrobenzoic acid) (900 $\mu$l) dissolved in 50 mM phosphate buffer, pH 7.6 (DTNB) as described in Ellman (1959, Arch. Biochem. Biophys. 82:70–72). PC standards were extracted from $Cd^{2+}$-grown *S. pombe* (ATCC 38390) as described by Ortiz et al. (1995, J. Biol. Chem. 270:4721–4728).

PC synthase activity was assayed according to Grill et al. (1989, Proc. Natl. Acad. Sci. U.S.A. 86:6838–6842) in reaction media containing crude soluble fraction (50 $\mu$g protein), purified AtPCS1-FLAG (0.5 $\mu$g) or no protein, 3.3 mM GSH, 10 mM 2-mercaptoethanol and 200 mM Tris-HCl buffer (pH 8.0) plus or minus 200 $\mu$M $CdCl_2$ at 37° C. for 40 minutes. After terminating the reactions with 5% (w/v) 5-sulfosalicylic acid, PCs were estimated in the supernatant by reverse-phase FPLC and reaction with DTNB.

Amino acid analysis

The chain lengths of the PCs synthesized from GSH by AtPCS1-FLAG in vitro were determined by estimating their Glu/Gly ratios (ratio=n=number of Glu-Cys repeats per Gly) after acid hydrolysis of the appropriate fractions from reverse-phase FPLC. Aliquots of the fractions were taken to dryness in pyrolyzed glass tubes, hydrolyzed in gas-phase 6 N HCl for 20 hours at 110° C. before ion-exchange chromatography, post-column derivatization with O-phthalaldehyde and fluorescence detection (Udenfriend et al., 1972, Science 178:871–874).

Northern and Southern blot analyses

Arabidopsis seedlings were grown for 21 days in Gamborg's B-5 medium and total RNA and genomic DNA were extracted from roots and shoots in TRIzol R Reagent (Gibco BRL Life Technologies, Gaithersburg, Md.) according to the manufacturer's recommendations. The RNA samples and restricted DNA samples were electrophoresed, blotted and hybridized with $^{32}$P-labeled, random-primed 1.5 kb NotI/SmaI restriction fragment corresponding to the coding sequence of AtPCS1 by standard procedures (Lu et al., 1997, Proc. Natl. Acad. Sci. U.S.A. 94:8243–8247).

SDS-PAGE and Western blot analyses

Protein samples were dissolved in denaturation buffer and subjected to one-dimensional SDS-polyacrylamide gel electrophoresis on 10% (w/v) slab gels in a Bio-Rad mini-gel apparatus (Kim et al., 1994, Proc. Natl. Acad. Sci. U.S.A. 91:6128–6132). For direct protein detection, the gels were stained with Silver Stain-Plus (Bio-Rad Laboratories, Richmond, Calif.)., For immunodetection of AtPCS1-FLAG, the separated samples were electrotransferred and probed with anti-FLAG M2 antibody (Sigma. Chemical Co., St. Louis, Mo.) by standard procedures. Immunoreactive bands were visualized by enhanced chemiluminescence (ECL) detection with an ECL kit (Amersham Corp., Arlington Heights, Ill.) per the manufacturer's instructions.

Protein estimations

Protein was estimated by the dye-binding method (Bradford, 1976, Anal. Biochem. 72:248–254).

Chemicals

All of the general reagents were obtained from Fisher Scientific (Pittsburgh, Pa.), Research Organics Inc. (Cleveland, Ohio), or Sigma Chemical Co. (St. Louis, Mo.).

The Results of the experiments presented in this example are now described.

Suppression cloning

The isolation of a plant cDNA encoding a PC synthase was based on yeast suppression screens for Arabidopsis yeast activation protein 1 (YAP1)-like transcription factors. Briefly, since expression of the yeast (*S. cerevisiae*) cadmium (resistance) factor gene YCF1 (ScYCF1), which encodes an ATP-binding cassette (ABC) transporter responsible for the vacuolar sequestration of $Cd^{2+}$ as Cd.GSH complexes (Li et al., 1997, Proc. Natl. Acad. Sci. U.S.A. 94:42–47), is transcriptionally activated by the bZIP DNA-binding protein YAP1 (Wemmie et al., 1994, J. Biol. Chem. 269:14690–14697), a two-step screening procedure described previously elsewhere herein (see Materials and Methods) was performed to isolate AtPCS1. That is, first, the *S. cerevisiae* yap1Δ disruptant strain SM12 was transformed with an Arabidopsis CDNA library constructed in the yeast-*Escherichia coli* shuttle vector pFL61 (Minet et al., 1992, Plant J. 2:417–422) and transformants were selected that were capable of growth on YPD medium containing 200 $\mu$M $CdCl_2$. Then, rescue of pFL61 plasmids from the $Cd^{2+}$-resistant transformants was performed and the plasmids were used to transform *S. cerevisiae* ycf1Δ disruptant strain DTY 168. Ura+ transformants capable of growth on AHC medium containing 200 $\mu$M $CdCl_2$ were selected.

It was reasoned that pFL61-borne Arabidopsis cDNAs encoding YAP1-like factors would suppress yap1Δ but not ycf1Δ mutants whereas cDNAs encoding $Cd^{2+}$ resistance factors acting through a pathway distinct from that of YAP1 would not only suppress yap1Δ but would also suppress ycf1Δ mutants.

Of a total of 105 $Cd^{2+}$-resistant SM12 transformants identified which suppressed yap1Δ, only one harbored a pFL61-borne cDNA satisfying the minimum requirement of a YAP1 equivalent, i.e., the cDNA did not suppress the $Cd^{2+}$-hypersensitivity of strain DTY168. All of the remaining 104 SM12 transformants harbored pFL61 plasmids and were able to suppress the $Cd^{2+}$ hypersensitivity of strain DTY168 in the second step. Of these, two identical clones were isolated and characterized further because of their ability to confer tolerance to $Cd^{2+}$ concentrations well in excess of those tolerated by DTY168 cells transformed with any one of the other clones.

After determining that the cDNA inserts of these clones were identical by sequencing their ends, one, pFL61-AtPCS1, was investigated further.

Sequence characteristics of AtPCS1

Sequence analysis established that the open reading frame of the 1.7 kb cDNA insert (SEQ ID NO: 1) of pFL61-AtPCS1 encoded a 55 kDa polypeptide (SEQ ID NO: 2) sharing about 33% identity (about 48% similarity) to a hypothetical gene product in the GenBank database from *Schizosaccharomyces pombe* (accession number Q10075) and about 32% identity (about 45% similarity) to a hypothetical gene product from *Caenorhabditis elegans* (GenBank accession number Z66513). AtPCS1 shares these regions of homology with the GenBank sequences from *S.*

*pombe* and *C. elegans* in overlaps of 379 and 366 amino acid residues, respectively (FIG. 1 and FIG. 9). Whichever pair of polypeptides was compared, sequence conservation was greater in the N-terminal halves than the C-terminal halves of the predicted amino acid sequences. AtPCS1 was 44% and 45% identical (62% and 63% similar) to the 46.7 kDa *S. pombe* and 40.8 kDa *C. elegans* gene products, respectively, in the sequences encompassed by AtPCS1 residues 1–241 but only 20% and 12% identical (40% and 37% similar) in the sequences encompassed by AtPCS1 residues 266–241. Without wishing to be bound by theory, although AtPCS1 was distinguishable from the other two polypeptides by its possession of a 73–74 amino acid residue C-terminal extension, AtPCS1 has conserved sequences corresponding to positions 49–68, 70–91, 152–165 and 176–190 which are family-specific inasmuch as BLAST searches of the GenBank database using these sequences identified these three gene products but did not identify other gene products.

Searches of the Arabidopsis Genomic Database indicated that this organism contains at least two AtPCS genes: AtPCS1 (SEQ ID NO: 1) which is located within P1 clone MRH10 and which maps adjacent to marker mi83 on chromosome 5 and another gene, nominally AtPCS2 (SEQ ID NO: 3; GenBank Accession No. AC003027, FIG. 17), located within BAC clone F21M11 which maps to chromosome 1 and which encodes a deduced polypeptide (SEQ ID NO: 4) sharing greater than approximately 70% sequence identity (approximately 85% similarity) with AtPCS1. Since Southern blot analyses of restricted Arabidopsis genomic DNA yielded hybridization patterns necessitating two, but not more, AtPCS-like genes when probed with the coding sequence of AtPCS1, AtPCS1 and AtPCS2 are inferred to be the sole representatives of this gene family in Arabidopsis.

Further, high stringency Northern blot analysis detected a single 1.7 kb band after hybridization of random-primed, $^{32}$P-labeled AtPCS1 cDNA with total RNA extracted from roots and shoots of 21-day-old Arabidopsis seedlings (FIG. 2), indicating that the cDNA insert of pFL61-AtPCS1 was full-length and was derived from Arabidopsis rather than being derived from a nonplant contaminant of the cDNA library.

Heavy metal tolerance

To probe the functional capabilities of AtPCS1 and to render its translation product immunodetectable, AtPCS1::FLAG fusions were engineered in the yeast-*E. coli* shuttle vector pYES3. Since BLAST searches did not disclose any AtPCS1-like sequences in *S. cerevisiae*, this organism was considered suitable for examining the mode of action of AtPCS1 without interference from endogenous orthologs.

After establishing that the resulting pYES3-AtPCS1::FLAG construct (and its C-terminally FLAG epitope-tagged translation product) was as efficacious as pFL61-AtPCS1 and pYES3-AtPCS1 in suppressing the $Cd^{2+}$-hypersensitivity of *S. cerevisiae* ycf1Δ disruptant strain DTY167, pYES3-AtPCS1::FLAG-dependent suppression of sensitivity to a broader range of metals or their oxides was screened in this strain and in the metallothionein-deficient, $Cu^{2+}$-hypersensitive, cup1Δ strain DTY4.

Figure 3:
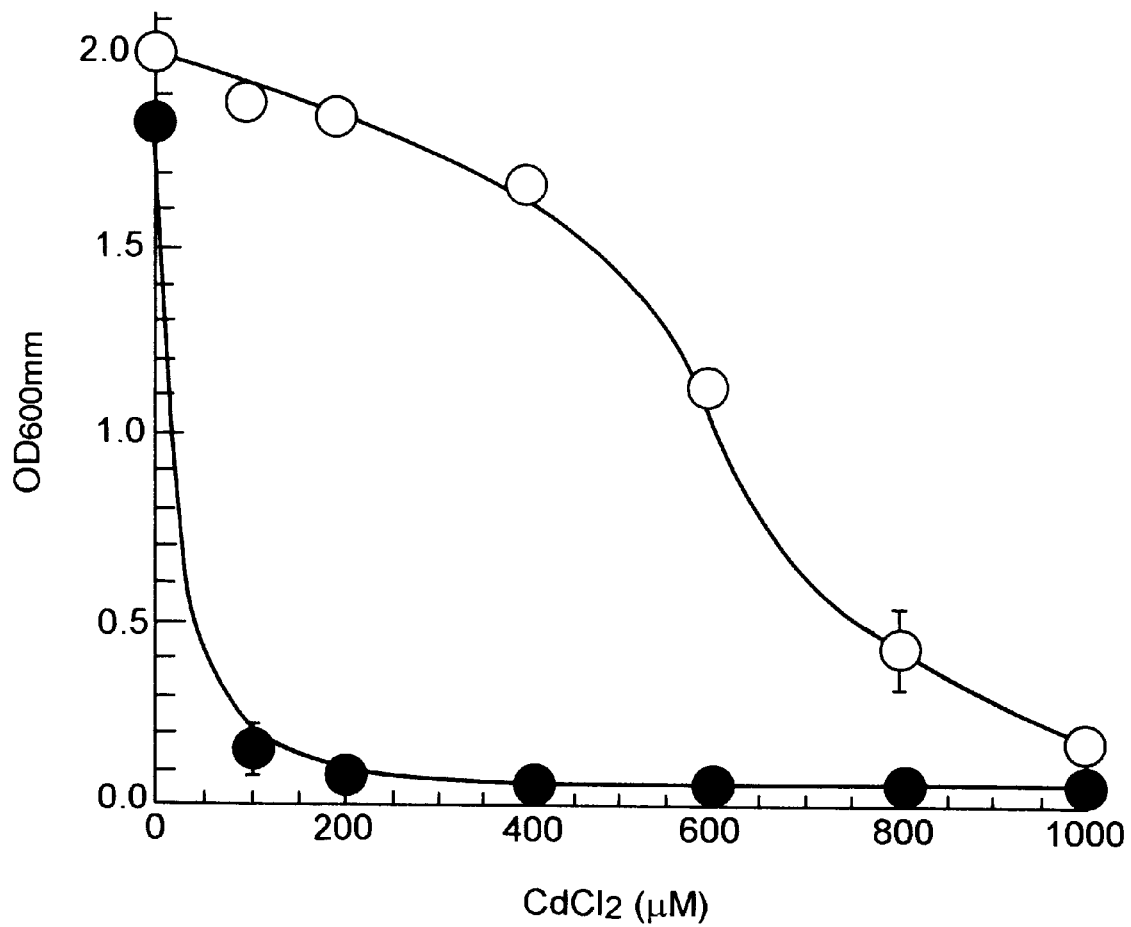
FIG. 3 is a graph depicting the suppression of $Cd^{2+}$-hypersensitivity of S. cerevisiae ycf1 Δ mutant strain DTY167 by plasmid-borne AtPCS1. Yeast ycf1 Δ strain DTY167 was transformed with pYES3-AtPCS1::FLAG(○) (encoding functional FLAG-tagged AtPCS1) or empty vector pYES3 lacking an AtPCS1::FLAG insert (●). Transformed yeast cells were grown at 30° C. to an $OD_{600\ nm}$ of approximately 1.8 in AHC medium supplemented with glucose and tryptophan before inoculation of aliquots into 2 ml volumes of the same medium containing different concentrations of heavy metal salts. $OD_{600\ nm}$ was measured after growth for 36 hours. Similar growth assays in liquid media containing $AsO_4^{3-}$, $AsO_2^-$, $Cu^{2+}$ or $Hg^{2+}$, demonstrated that plasmid-borne ATPCS1::FLAG increased the concentrations of these heavy metal ions or their oxides required for 50% attenuation of cell density from 300, 200, 250, and 4 μM to 550, 325, 600, and 6.3 μM, respectively.

The data disclosed herein demonstrate that AtPCS1-FLAG is a multispecific heavy metal resistance factor. That is, plasmid-borne AtPCS1-FLAG not only conferred strong resistance to $Cd^{2+}$ but also conferred moderate resistance to $AsO_4^{3-}$, $AsO_3^{-}$, $Cu^{2+}$ and $Hg^{2+}$ with an overall rank order, based on the fold increases in the concentrations at which the metals exerted 50% inhibition of growth in liquid culture compared with pYES3 empty-vector controls, of $Cd^{2+}$ (24-fold)>>$Cu^{2+}$ (2.4)>$AsO_4^{3-}$ (1.8)>$AsO^{2-}$ (1.6)=$Hg^{2-}$ (1.6) (FIG. 3). Thus, AtPCS1-FLAG (and AtPCS1) confers resistance not only to cadmium, but also to arsenate, arsenite, mercury, and copper concentrations well in excess of those tolerated by the untransformed ycf1Δ DTY167 or cup1Δ DTY4 strains.

Cellular localization of AtPCS1

Heterologously expressed AtPCS1-FLAG did not appear to confer tolerance by promoting the exclusion or extrusion of heavy metals from the cytosol through an association with the plasma or vacuolar membrane. Cells expressing AtPCS1-FLAG demonstrated an enhanced, not diminished, heavy metal content. Further, the vacuole-deficient pep5Δ strain DTY214, which is $Cd^{2+}$ hypersensitive due to the absence of a sizable vacuolar compartment for metal sequestration (Li et al., 1997, Proc. Natl. Acad. Sci. U.S.A. 94:42–47), was nearly as susceptible to suppression by pYES3AtPCS1::FLAG as strain DTY167. AtPCS1-FLAG localized almost exclusively to the soluble fraction of DTY167/pYES3-AtPCS1::FLAG transformants.

Figure 4:
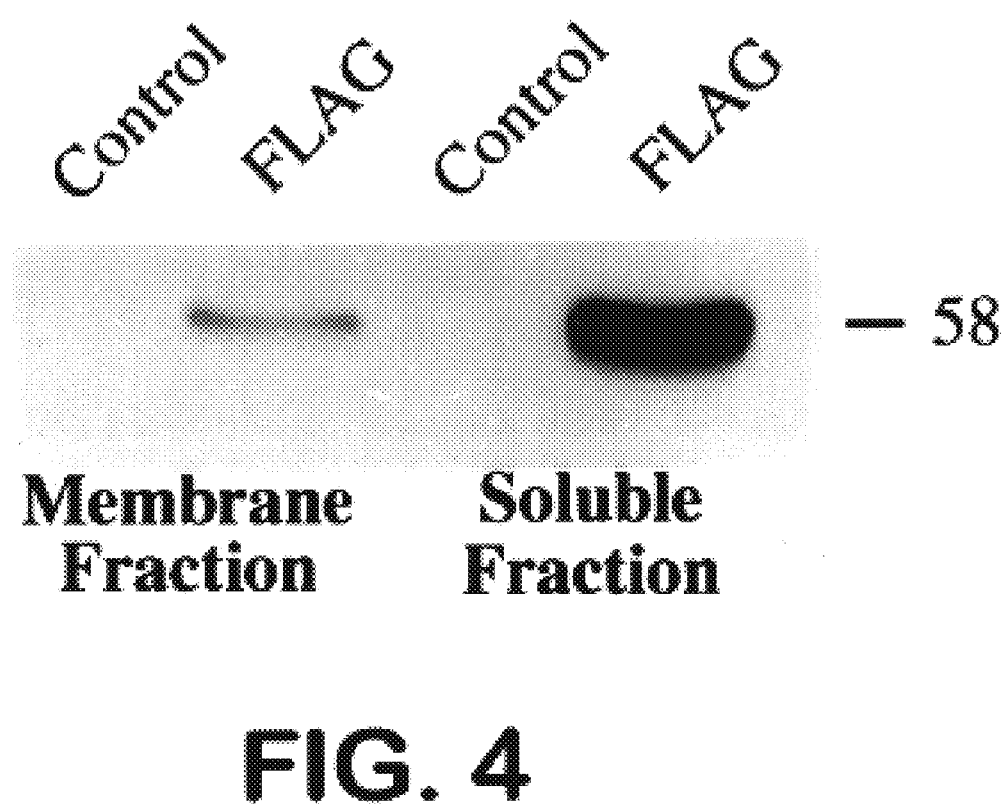
FIG. 4 is an image depicting a SDS-PAGE and Western analysis of AtPCS1 -FLAG in the total soluble and membrane fractions from whole cell extracts prepared from DTY167/pYES3-AtPCS1::FLAG (FLAG) and DTY167/pYES3 (Control) cells. The membrane fraction is comprised of material sedimented by centrifugation of the 4,000×g supernatant from whole cell extracts at 10,000×g. The soluble fraction comprised material retained in the supernatant of whole cell extracts after successive centrifugations at 4,000×g and 10,000×g. Proteins (25 μg) were subjected to SDS-PAGE on 10% gels, and were then electrotransferred to nitrocellulose membrane filters and probed with anti-FLAG M2 monoclonal antibody to detect the fusion protein. The immunoreactive bands were visualized using enhanced chemiluminescence (ECL) detection with an ECL kit (Amersham Pharmacia Life Sciences, St. Petersburg, Fla.), according to the manufacturer's instructions.

Differential centrifugation of mechanically disrupted DTY167/pYES3-AtPCS1::FLAG spheroplasts resolved the total extracts into soluble (supernatant) and membrane-enriched (pelletable) fractions. Of the two fractions, only the supernatant fraction yielded appreciable $M_r$ 58,000, anti-FLAG antibody-reactive polypeptide after SDS-PAGE and Western blot analysis (FIG. 4). The migration properties of the sole anti-FLAG antibody-reactive polypeptide recovered were precisely those expected from the coding sequence of AtPCS1::FLAG, and fractionation of DTY167/pYES3 negative control cells in an identical manner did not yield an immunoreactive protein in either the soluble or membrane fraction (FIG. 4). Therefore, the FLAG-bearing band in the soluble fraction from DTY167/pYES3-AtPCS1::FLAG cells was inferred to be derived solely from the cDNA insert of pYES3-AtPCS1::FLAG.

In vivo $Cd^{2+}$ binding

Having determined that AtPCS1-FLAG heterologously expressed in *S. cerevisiae* was a soluble protein, the effects, if any, of AtPCS1 on the amount and distribution of bound heavy metal were assessed by comparing the chromatographic profiles of soluble extracts from DTY167/pYES3-AtPCS1::FLAG cells to the profiles of soluble extracts from DTY167/pYES3 control cells after growth in liquid medium containing $^{109}CdCl_2$. The results of these analyses not only provided the first indication that AtPCS1-FLAG, itself, binds $^{109}Cd^{2+}$ but also implicated AtPCS1-FLAG in increasing in the amount of, and/or increasing the degree of binding of $^{109}Cd^{2+}$ to, another heavy metal-binding factor.

Figure 5:
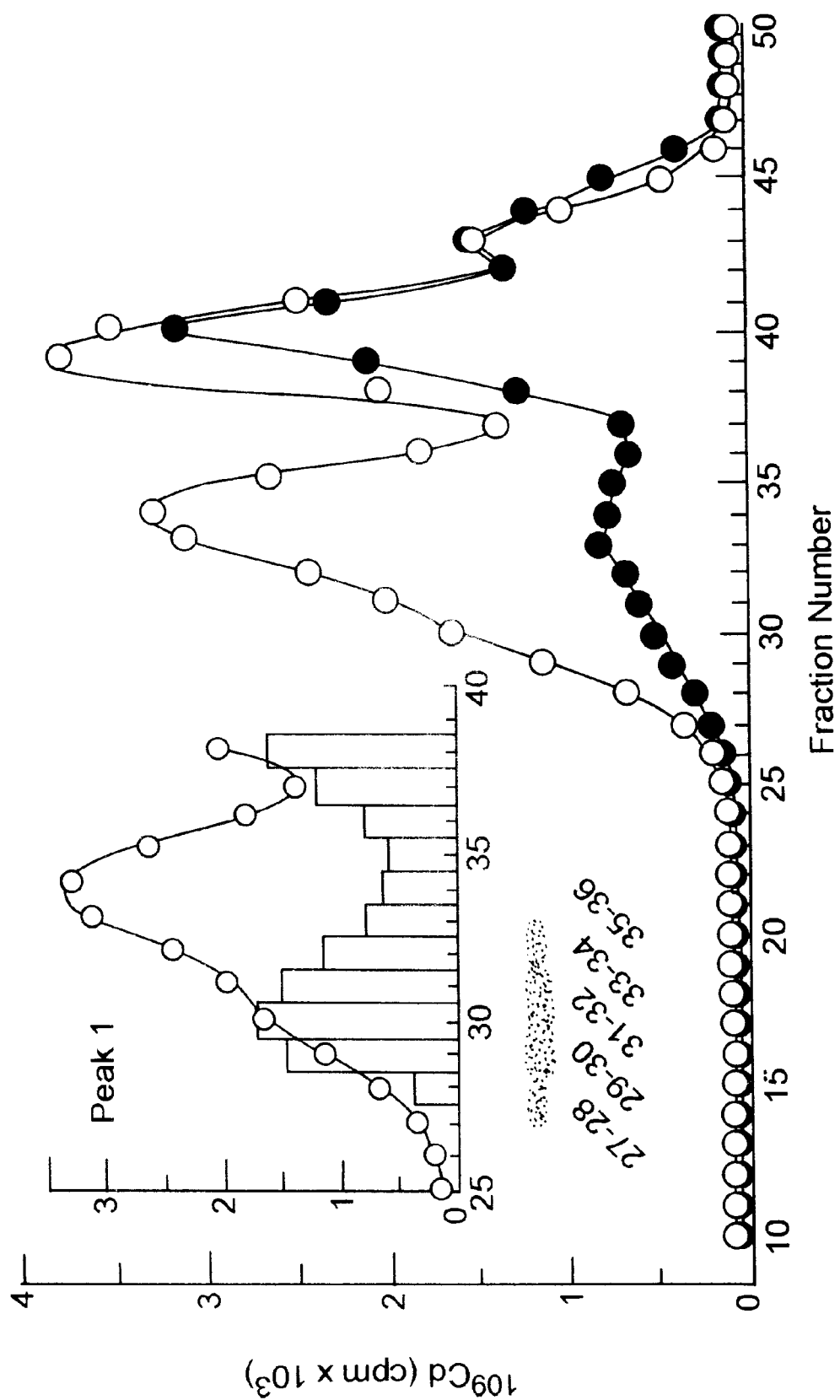
FIG. 5 is an image (comprising an insert) depicting the gel-filtration chromatography of soluble fractions extracted from DTY167/pYES3-AtPCS1::FLAG (○) cells and DTy167/pYES3 cells (●) after growth in media containing $^{109}CdCl_2$ (main graph). The data illustrate a direct comparison of the $^{109}Cd$ radioactivity profile of peak 1 from the soluble fraction extracted from DTY167/pYES3-AtPCS1::FLAG (○) cells with the $^{109}Cd$ radioactivity profile obtained after Superose-6 chromatography of immunoaffinity-purified AtPCS1-FLAG after equilibrium dialysis against 5 µM $^{109}CdCl_2$ (peak 1 of histogram of insert depicting fractions 25–38). AtPCS1-FLAG was detected by SDS-PAGE and Western blot analysis of 20 µl aliquots of pooled pairs of fractions (i.e., 27–28, 29–30, 31–32, 33–34, 35–36) from chromatography of the DTY167/pYES3-AtPCS1::FLAG cell extracts as depicted under the histogram insert.

FPLC of the soluble fraction from $^{109}CdCl_2$-grown DTY167/pYBS3-AtPCS1::FLAG cells on a Superose-6 HR 10/30 column resolved-two major peaks and one minor peak of $^{109}Cd$ radioactivity with maxima corresponding to fractions 34 (peak 1), 39 (peak 2) and 43 (peak 3) (FIG. 5, main graph). Equivalent $^{109}Cd$ radioactivity profiles were obtained for the soluble fraction from $^{109}CdCl_2$-grown DTY167/pYES3-AtPCS1 cells demonstrating that the FLAG epitope-tag did not contribute to $^{109}Cd^{2+}$ binding. By contrast, the soluble fraction from DTY167/pYES3 cells grown under identical conditions lacked most of the $^{109}Cd$ radioactivity under peak 1 although peaks 2 and 3 had the same profiles and eluted at the same positions as the corresponding peaks in the DTY167/pYES3-AtPCS1::FLAG extracts (FIG. 5). While superficially consistent with the notion that the peak unique to the DTY167/pYES3-AtPCS1::FLAG extracts (peak 1) might be wholly explicable by direct binding of $^{109}$Cd to AtPCS1-FLAG, closer inspection of the column fractions and experiments on purified AtPCS1-FLAG demonstrated this not to be the case. AtPCS1-FLAG bound $Cd^{2+}$ at high affinity and high capacity but this, alone, did not account for the peak profiles of the DTY I 67/pYES3-AtPCS1::FLAG cell extracts.

Immunoaffinity purification of AtPCS1-FLAG

Figure 6:
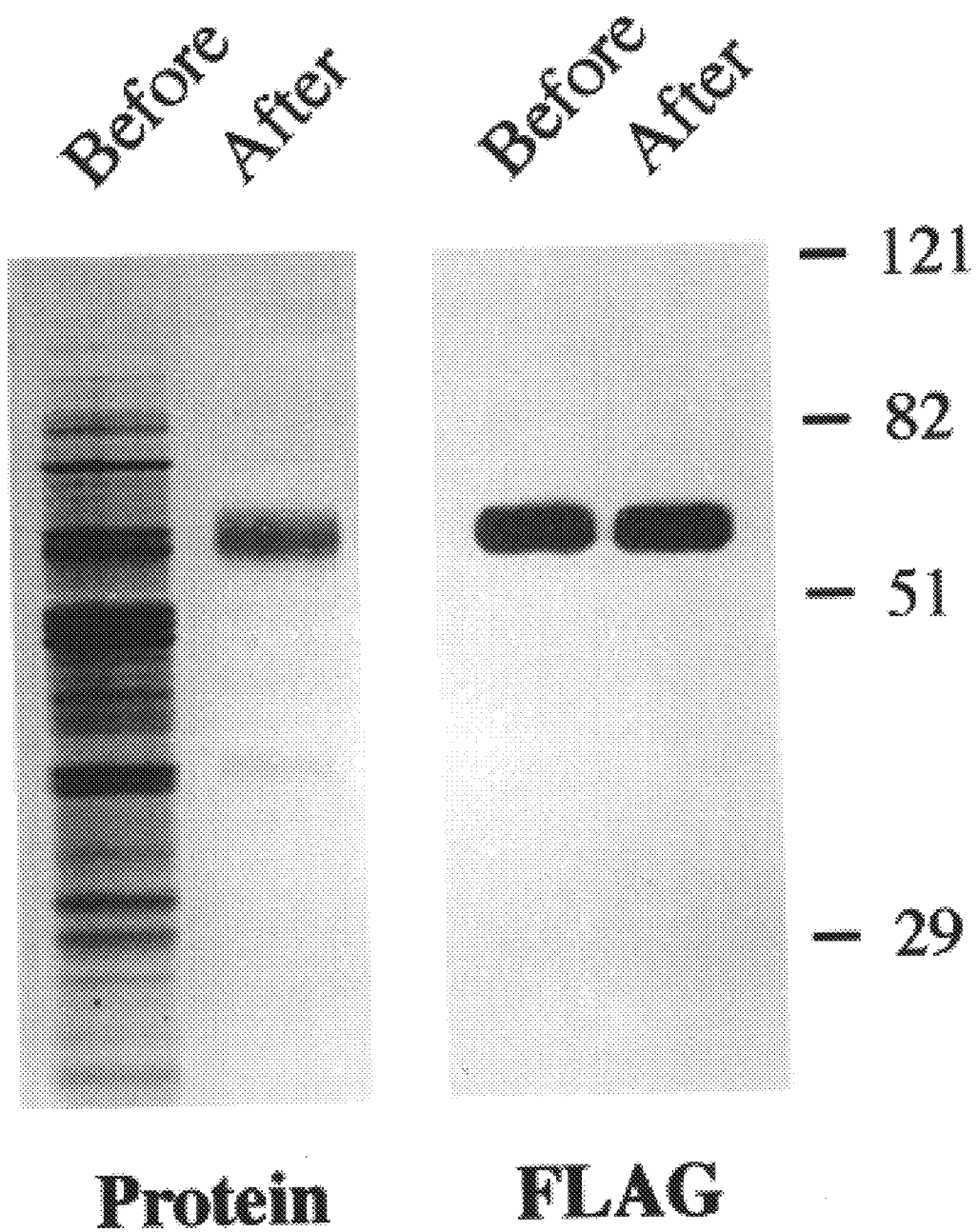
FIG. 6 is an image (comprising two panels) of a gel depicting the purification of AtPCS1-FLAG by immunoaffinity chromatography of the soluble fraction from DTY167/pYES3-AtPCS1::FLAG cells on an anti-FLAG M2 immunoaffinity column. Left panel (Protein): Silver-stained SDS-gel visualizing the proteins of the soluble fraction (5 µg protein) before (Before) and after (1 µg protein) (After) purification of AtPCS1-FLAG. Right panel (FLAG): Western blot analysis of FLAG epitope before (25 µg of the total soluble fraction protein) (Before) and after (1 µg protein) (After) purification of AtPCS1-FLAG. The positions of the molecular weight markers ($M_r \times 10^3$) are indicated.

In order to define its chromatographic and metal-binding properties directly (and, eventually, to assay for its enzymatic activity) AtPCS1-FLAG was purified from the soluble fraction of DTY I 67/pYES3-AtPCS1::FLAG cells by immunoaffinity chromatography on an anti-FLAG M2 affinity column. SDS-PAGE (Protein) and Western blot (FLAG) analyses of the soluble fraction before and after chromatography demonstrated that this immunopurification procedure yielded a single, anti-FLAG antibody-reactive, $M_r$ 58,000 protein species retaining the electrophoretic and immunological properties of the polypeptide in the starting material (FIG. 6).

Intrinsic and extrinsic binding

Equilibrium dialysis of the immunoaffinity-purified protein against a range of $^{109}CdCl_2$ concentrations verified that AtPCS1-FLAG bound $^{109Cd2+}$ at a high affinity ($K_d$ of 0.54±0.20 µM) and at a high capacity (stoichiometric ratio of 7.09±0.94). However, though consistent with a contribution by AtPCS1-FLAG to the overall $^{109}Cd^{2+}$ radioactivity profile, the intrinsic $Cd^{2+}$-binding activity of AtPCS1-FLAG, whether in whole extracts or in purified state, was not sufficient to account fully for the $^{109}$Cd-radioactivity profile of peak 1 in the DTY167/pYES3-AtPCS1::FLAG cell extracts. Whereas SDS-PAGE and Western analysis of the fractions from chromatography of the DTY167/pYES3-AtPCS1::FLAG cell extracts demonstrated a consistent displacement of the maximum for AtPCS1-FLAG polypeptide (fraction 29–32) from the maximum for $^{109}$Cd radioactivity (fractions 33–35), this could not be simulated with pure $^{109}$Cd-complexed AtPCS1-FLAG. Chromatography of purified AtPCS1-FLAG after equilibrium dialysis against $^{109}CdCl_2$ yielded strictly superimposable profiles for both AtPCS1-FLAG polypeptide and $^{109}$Cd radioactivity whose maxima (fractions 29–32) coincided with that of AtPCS1-FLAG in the DTY167/pYES3-AtPCS1::FLAG extracts (FIG. 5, insert graph). On this basis, AtPCS1-FLAG was concluded to not only bind $Cd^{2+}$ itself but also to elicit the formation or activation of a lower molecular weight metal-binding factor or factors. This interpretation was reinforced by two factors. First, the finding that $Cd^{2+}$-complexed and free AtPCS1-FLAG coeluted during Superose-6 chromatography, so excluding a change in the elution properties of AtPCS1-FLAG consequent on $Cd^{2+}$ binding as a factor contributing to peak profile. Second, by experiments demonstrating the inapplicability of a scheme in which chromatographic displacement of the AtPCS1-FLAG and $^{109}$Cd radioactivity maxima was the result of partial dissociation of bound $^{109}$Cd from AtPCS1-FLAG and its transfer to a smaller pre-existent factor common to both DTY167/pYES-AtPCS1::FLAG and DTY167/pYES3 cells.

PC biosynthesis

The capacity of AtPCS1 to bind $Cd^{2+}$ and stimulate the formation of lower weight metal ligands was indicative of a PC synthase in that such an enzyme ostensibly has the same property, i.e., the facility to catalyze PC synthesis when activated by $Cd^{2+}$. Other similarities between AtPCS1 and PC synthase that prompted investigation of whether AtPCS1 is a PC synthase or, at least, contributes to PC synthesis, were as follows. AtPCS1 has a computed mass of 55 kDa (FIG. 1) and an electrophoretic mobility of 58,000 (FIGS. 4 and 6) which is commensurate with an apparent subunit size of 50,000 for the activity of partially purified PC synthase preparations from plants (Grill et al., 1989, Proc. Natl. Acad. Sci. U.S.A. 89:6838–6842). Further, AtPCS1and its homologs (FIG. 1) are found in both plants and *S. pombe* as is PC synthase (Rauser, 1990, Annu. Rev. Biochem. 59:61–86; Zenk, 1996, Gene 179:21–30). In addition, AtPCS1, like the products of PC synthase activity, though capable of conferring greatest tolerance to $Cd^{2+}$, also confers tolerance to other heavy metals such as $Cu^{2+}$ (Rauser, supra; Zenk, supra). Moreover, transformation of OGSH-deficient *S. cerevisiae* gsh2Δ mutants, in which the coding sequence for GSH synthetase is disrupted (Inoue et al., 1998, Biochem. Biophys. Acta 1395:315–320), with pYES3-AtPCS1::FLAG does not confer $Cd^{2+}$-tolerance, suggesting that AtPCS1, like PC synthase, is ineffective unless GSH is available.

The involvement of AtPCS1 in PC biosynthesis was examined at three levels. First, it was determined whether. $CdCl_2$-grown DTY167/pYES3-AtPCS1::FLAG cells contained elevated PC levels when compared with $CdCl_2$-grown DTY167/pYES3 cells, and, if so, whether PC accumulation required growth in media containing $Cd^{2+}$. Second, it was determined whether the soluble fraction from DTY167/pYES3-AtPCS1::FLAG cells had an increased capacity for $Cd^{2+}$-dependent PC synthesis in vitro when compared with the soluble fraction from DTY167/pYES3 cells. Third, it was examined whether purified AtPCS1-FLAG catalyzed $Cd^{2+}$-dependent PC synthesis from GSH. At all levels investigated, AtPCS1 exhibited all of the characteristics of a PC synthase.

Figure 7A:
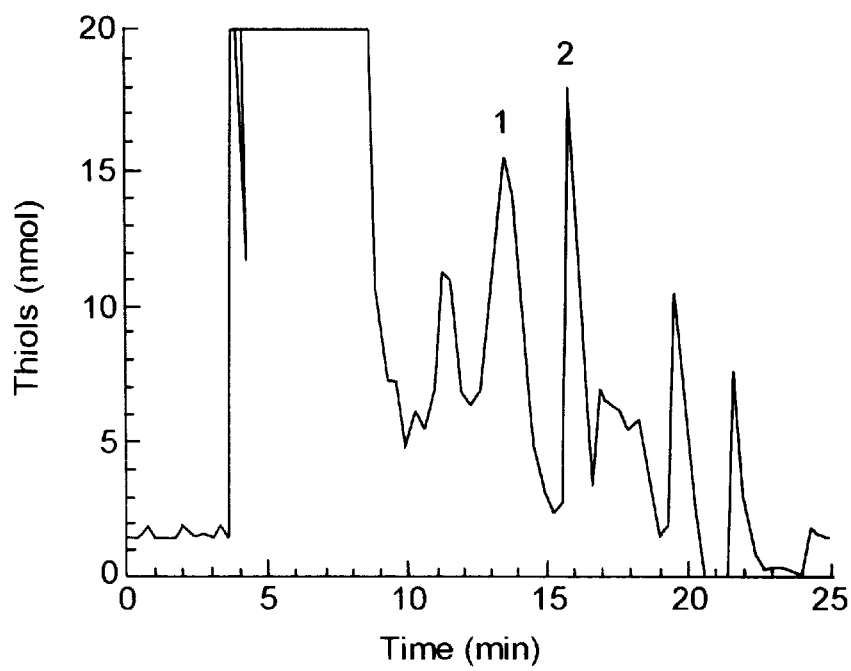
FIG. 7A is a graph depicting AtPCS1-FLAG-dependent PC synthesis in vivo and in vitro. The data disclosed herein depict reverse-phase FPLC analysis of non-protein thiols present in the soluble fractions extracted from DTY167/pYES3-AtPCS1::FLAG cells after growth in liquid medium containing $CdCl_2$ (50 µM). Peaks 1 and 2 were found to comigrate with $PC_2$ and $PC_3$ standards, respectively, purified from S. pombe. The equivalent fractions extracted from DTY167/pYES3-AtPCS1::FLAG cells after growth in medium lacking $CdCl_2$ and from DTY167/pYES3 cells after growth in medium containing $CdCl_2$ (50 µM) were devoid of PC-like, non-protein thiols.

DTY167/pYES3-AtPCS1::FLAG cells accumulated PCs in a $Cd^{2+}$-dependent manner. Reverse-phase FPLC analysis of nonprotein thiol compounds in the soluble fraction from DTY167/pYES3-AtPCS1::FLAG cells after growth in medium containing $CdCl_2$ revealed multiple peaks eluting after the GSH/2-ME injection peak, whose total thiol content represented 51 nmol/mg extracted protein (FIG. 7A). The two most prominent of these peaks, peaks 1 and 2, contributed 4 nmol thiol/mg protein and eluted at the same positions as $PC_2$ and $PC_3$ standards prepared from *S. pombe* (FIG. 7A). The corresponding fractions from $CdCl_2$-grown DTY167/pYES3 cells and DTY167/pYES3-AtPCS1::FLAG cells after growth in medium lacking $Cd^{2+}$ were devoid of nonprotein thiols, other than those associated with the GSH/2-mercaptoethanol injection peak.

Expression of plasmid-borne AtPCS1::FLAG was necessary for the generation of extractable PC synthase activity but, unlike intracellular PC accumulation, did not require exposure of the cells to $Cd^{2+}$ before extraction. In vitro assays of the capacity of the soluble fractions from DTY167/pYES3-AtPCS1::FLAG cells grown in the presence and absence of $Cd^{2+}$ for the incorporation of GSH into PCs demonstrated exclusive synthesis of $PC_2$ and $PC_3$ at aggregate rates of 0.50 and 0.34 nmol/mg/minute when assayed in media containing 3.3 mM GSH and 200 µM $CdCl_2$.

The corresponding fractions from DTY167/pYES3 cells yielded rates below the limits of detection (<0.01 nmol/mg/minute) irrespective of whether the cells had been grown in the presence or absence of $Cd^{2+}$. In no case was PC synthase activity detectable when $Cd^{2+}$ was omitted from the assay medium, implying an obligate requirement for heavy metal ions for PC synthesis.

AtPCS1-FLAG was sufficient for the $Cd^{2+}$-dependent synthesis of PCs from GSH in vitro. The single $M_r$ 58,000 polypeptide species purified by immunoaffinity chromatography of the soluble fraction from DTY167/pYES3-

Figure 7B:
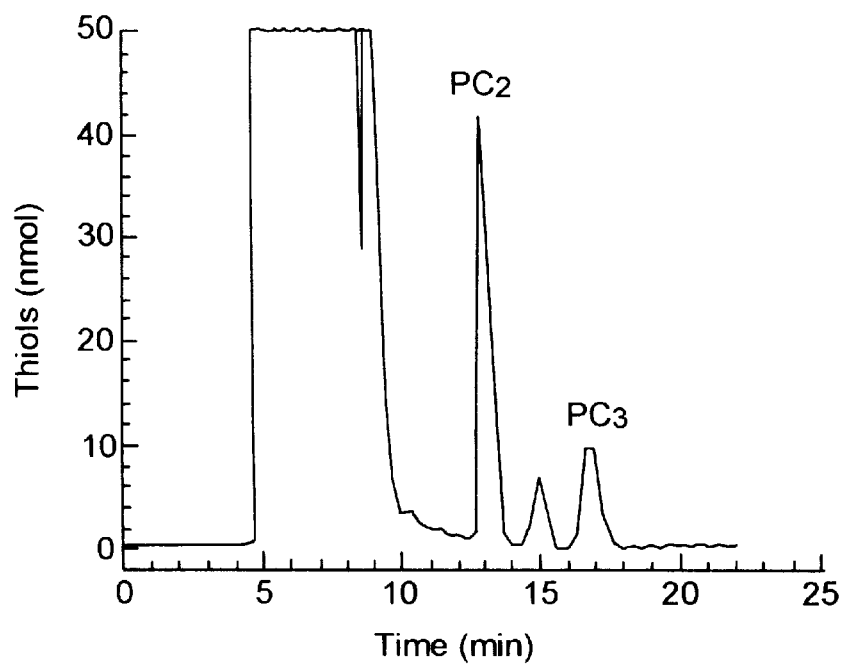
FIG. 7B is a graph depicting the reverse-phase FPLC analysis of the non-protein thiols formed after incubation of GSH (3.3 mM) with immunoaffinity-purified AtPCS1-FLAG in the presence of $Cd^{2+}$ (200 µM). The peaks designated "$PC_2$" and "$PC_3$" were identified on the basis of their Glu/Gly ratios (2.1±0.1 and 2.9±0.2, respectively) and their comigration with S. pombe PC standards. The major thiol peaks eluting 4–10 minutes after sample injection are-cellular GSH, and GSH and 2-mercaptoethanol (2-ME) present in the PC synthase assay media, respectively. No peaks other than those corresponding to GSH and 2-ME were detected when AtPCS1-FLAG or $Cd^{2+}$ were omitted from the incubation medium.

AtPCS1::FLAG cells (FIG. 6) catalyzed the incorporation of GSH into $PC_2$ and $PC_3$ at an aggregate rate of 30–35 µmol/mg/min and <0.01 nmol/mg/min in the presence and absence of $Cd^{2+}$, respectively (FIG. 7B). Control reaction mixtures lacking AtPCS1-FLAG did not yield any PCs. Given that AtPCS1-FLAG was the sole protein species in the reaction medium and that the products of its reaction with GSH, $PC_2$ and $PC_3$, were determined by quantitative amino acid analysis to have Glu/Gly ratios of 2.1±0.1 and 2.9±0.2, respectively, AtPCS1 was evidently capable of catalyzing the transfer of a γ-glutamylcysteine unit from one GSH molecule to another to form $PC_2$, or from one GSH molecule to $PC_2$ to form $PC_3$. As would be expected for a bona fide enzyme-catalyzed reaction, the amounts of $PC_2$ and $PC_3$ synthesized increased linearly with time to yield strict proportionality between the rates of synthesis and the amounts of AtPCS1-FLAG added to the reaction medium.

The data disclosed herein establish that AtPCS1, a novel cDNA from Arabidopsis, and, as more fully set forth below, its homologs from *T. aestivum, S. pombe* and *C. elegans*, as well as AtPCS2, encode PC synthases: $Cd^{2+}$-binding enzymes capable of high rates of $Cd^{2+}$-activated PC synthesis from GSH. As such, the cloning and in vitro reconstitution of AtPCS1 is of considerable value. Enzymologically, the ease with which AtPCS1-FLAG can be purified to apparent homogeneity in a single step from pYES3-AtPCS1::FLAG-transformed yeast to yield PC synthase preparations with a catalytic activity exceeding that of previous preparations from plants (Grill et al., 1989, Proc. Natl. Acad. Sci. U.S.A. 86:6838–6842) by more than $10^3$-fold will enable detailed mechanistic and crystallographic studies of this enzyme and the facile production of PCs in vitro on a milligram to gram scale. Molecularly, the amenability of AtPCS1 to be expressed in yeast in an active state and to confer a selectable phenotype provides a basis for probing the structural requirements of AtPCS1-catalyzed PC synthesis by the application of both site-directed and random mutagenic approaches. Evolutionarily, the existence of a PC synthase in *S. pombe* was suggested by the prior art extensively researching PC-based metal tolerance in that organism (Rauser, 1990, supra; Zenk, 1996, supra). Nonetheless, prior to the present invention, all previous attempts to identify and isolate a PC synthase from *S. pombe* had failed. Further, the discovery of an AtPCS1 homolog in the genome of *C. elegans* was completely surprising in that it invokes a role for not only GSH and MTs but also PCs in metal homeostasis in at least some animals. Genetically, the now ready availability of isolated genes encoding PC synthases and the demonstrated sufficiency of a single gene product for reconstitution of core catalysis will expedite investigations into the mechanisms by which plants and other organisms detoxify heavy metals.

In addition, as stated previously elsewhere herein, bioremediation (i.e., the use of organisms, usually plants or microbes, for the extraction and/or degradation of xenobiotics for environmental cleanup) has attracted considerable interest because of its potentially low cost and unobtrusive nature by comparison with conventional physical and chemical methods (Cunningham et al., 1995, Trends Biotechnol. 13:393–397). Of the different options for bioremediation, phytoremediation is particularly appealing for pollutants such as heavy metals that cannot be biodegraded because of the ease with which plants can be harvested using traditional technology. Therefore, the capacity of heterologously expressed AtPCS1 to confer resistance to the first, third and seventh ranked substances on the ASTDR/EPA priority list for the top 20 hazardous substances on U.S. Superfund sites, i.e., arsenic, mercury and cadmium, respectively, is particularly striking (URL http://www.atsdr.cdc.gov:8080/97list.html, 1997 CERCLA Priority List of Hazardous Substances, n=275, accessed on Mar. 25, 1999). The ability of AtPCS1 to confer resistance to these hazardous substances and the fact that in many $Cd^{2+}$ tolerant plant cell lines at least 90% of this metal is accumulated as Cd.PC complexes (Rauser, 1990, Annu. Rev. Biochem. 59:61–86; Zenk, 1996, Gene 179:21–30), indicate that AtPCS1 and similar genes may find application in the development of phytoremediation technologies through genetic manipulation of the capacity of plants for heavy metal hyperaccumulation.

EXAMPLE 2

Phytochelatin Synthases from Wheat and Yeast

The experiments presented in this example may be summarized as follows.

Phytochelatins play major roles in metal detoxification in plants and fungi. However, prior to the present invention, no gene encoding phytochelatin synthase had been identified. By screening for plant genes mediating metal tolerance, a wheat (*Triticum aestivum*) cDNA, TaPCS1, was identified whose expression in *Saccharomyces cerevisiae* (*S. cerevisiae*) results in a dramatic increase in cadmium tolerance. TaPCS1 encodes a protein (SEQ ID NO: 6; FIG. 9) of about 55 kDa with no similarity to proteins of known function. Homologs of this new gene family were identified from *Arabidopsis thaliana* (*A. thaliana*), *Schizosaccharomyces pombe* (*S. pombe*), and interestingly also from the nematode *Caenorhabditis elegans* (*C. elegans*). The Arabidopsis and *S. pombe* genes were also demonstrated to confer substantial increases in metal tolerance in yeast. PCS-expressing yeast cells accumulate more $Cd^{2+}$ than control cells. Further, PCS expression mediates $Cd^{2+}$ tolerance even in yeast mutants that are either deficient in vacuolar acidification or impaired in vacuolar biogenesis. PCS-induced metal resistance is lost upon exposure to an inhibitor of glutathione biosynthesis, a process necessary for phytochelatin formation. *S. pombe* cells disrupted in the PCS gene exhibit hypersensitivity to $Cd^{2+}$ and Cu and are unable to synthesize phytochelatins upon $Cd^2+$ exposure as determined by HPLC analysis. *S. cerevisiae* cells expressing PCS produce phytochelatins. Moreover, the recombinant purified *S. pombe* PCS protein displays phytochelatin synthase activity. These data demonstrate that PCS genes encode phytochelatin synthases and mediate metal detoxification in eukaryotes.

The Materials and Methods used in the experiments presented in this example are now described.

Yeast cultures, transformation and growth assays

The *S. cerevisiae* strains CY162 (MATαura3–52 trk1Δ his3Δ200 his4-15 trk2Δ1::pCK64; Anderson et al., 1992, Proc. Natl. Acad. Sci. U.S.A. 89:3736–3740), INVSc1 (MATαhis3Δ1 leu2 trp1-289 ura3-62), SEY6210 (MATαleu2-3, 112 Ura3-52 his3-Δ200 trp1-Δ901 lys2-801 suc2-Δ9), Δvps-18 (Robinson et al, 1991 Mol. Cell. Biol. 11:5813–5824) and Δvma4 (Ho et al, 1993, J. Biol. Chem. 268:221–227), and the *S. pombe* strains FY254 (h⁻ade6-M210 leu1-32 ura4-Δ18 can1-1) and FY261 (h⁺ ade6-M216 leu1-32 ura4-Δ18 can1-1), were used. *S. cerevisiae* cells were grown in yeast nitrogen base (YNB) or arginine-phosphate medium (Rodriguez-Navarro and Ramos, 1984, J. Bacteriol. 159:940–945) supplemented with the appropriate amino acids. *S. pombe* cells were grown in yeast extract medium (YE) or Edinburgh's Minimal Medium (EMM; Mitchison, 1970, In: Methods in Cell Physiology, Vol. 4, p. 131, Prescott, ed., Academic Press, New York; Nurse, 1975, Nature 256:457–451), supplemented appropriately. Growth assays using *S. cerevisiae* were performed as described previously (Clemens et al., 1998, Proc. Natl. Acad. Sci. U.S.A. 95:12043–12048). Growth of *S. pombe* in the presence of different $Cd^{2+}$ concentrations was assayed on EMM plates and in EMM liquid medium.

Library screening

CY162 cells (Anderson et al., 1992, Proc. Natl. Acad. Sci. U.S.A. 89:3736–3740) were transformed with a size-selected (greater than about 1.5 kb) fraction of a yeast expression library constructed using mRNA from root tips of wheat seedlings (Schachtman and Schroeder, 1994, Nature 370:655–658) following the lithium acetate method described by Gietz and Schiestl (1995, Meth. Mol. Cell. Biol. 5:255–269). Transformants were first selected for uracil prototrophy on YNB-ura, then the cells were transferred to arginine-phosphate liquid medium containing either 20 or 50 μM $CdCl_2$. After 2–4 days, DNA was extracted from the saturated cultures and *E. coli* cells were transformed. Several colonies per flask were analyzed further using restriction digests and nucleic acid sequencing.

DNA manipulations

*E. coli* strain DH5α was used for all DNA manipulations. Nucleic acids were expressed in *S. cerevisiae* using the inducible expression vector pYES2 (Invitrogen, La Jolla, Calif.) or the constitutive expression vector pYX132 (R & D Systems, Abingdon, UK).

DNA sequencing was performed on an ABI 370 automatic sequencer or using Sequenase (U.S. Biochemical Corp., Cleveland, Ohio).

PCR and Southern analysis were performed following established procedures (Ausubel et al., 1997, In: Current Protocols in Molecular Biology, Greene Pub. Associates and Wiley-Interscience, New York). Homologous sequences were identified by searching within the GenBank database using BLAST (Altschul et al., 1990, J. Mol. Biol. 215:403–410).

Amino acid sequences were analyzed with TMPred (Hofmann and Stoffel, 1993, Biol. Chem. 347:166) for the presence of putative transmembrane spans. Alignments were performed using the CLUSTAL W multiple sequence alignment program (Thompson et al., 1994, Nuc. Acids Res. 22:4673–4680).

Expression analysis

Northern analysis of RNA from wheat and Arabidopsis plants cells grown in the presence and absence of $Cd^{2+}$ was performed according to established procedures (Ausubel et al., 1987, In: Current protocols in molecular biology. Greene Pub. Associates and Wiley-Interscience, New York). For RT-PCR, RNA was isolated from 4 day old wheat plants that were either untreated or treated with 100 μM $Cd^{2+}$ for 6 hours. RNA was isolated from roots and shoots separately. First strand cDNA was synthesized from these RNA samples using the cDNA Cycle Kit (Invitrogen, La Jolla, Calif.). Ten ng of cDNA were used per PCR reaction. For competitive PCR, a PCR fragment amplified from wheat genomic DNA was cloned using the same primer pair as for the RT-PCR assay. Due to the presence of an intron, this fragment is about 100 bp longer than the fragment amplified from cDNA and this longer fragment was used as a competitor in PCR reactions. Competitor DNA was added to the PCR reaction in varying amounts between 0.1 and 5 fg. The PCR reaction was performed using 32 cycles of 30 seconds at 94 ° C., 2 minutes at 55° C., and 1 minute at 72° C. The PCR products were analyzed using agarose gel electrophoresis.

$Cd^{2+}$ accumulation

*S. cerevisiae* cells were grown in arginine-phosphate medium for 24 hours in the presence of various amounts of $CdCl_2$ containing 0.5 μCi $^{109}Cd^{2+}$. The cells were harvested and washed. The radioactivity was determined as described previously (Clemens et al., 1998, Proc. Natl. Acad. Sci. U.S.A. 95:12043–12048).

*S. pombe* knockout

The internal XbaI/HindIII fragment of SpPCS was subcloned into pYES2. Using site-directed mutagenesis, a BamHI site and a SacI site were introduced into this construct. A BamHI/SacI fragment of the ura4 marker in pTZura was cloned into the mutated SpPCS construct. *S. pombe* strain FY254 was transformed with 0.5 μg of the linearized knockout construct using the LiAc procedure (Okazaki et al., 1990, Nucleic Acids Res. 25:6485–6489). Transformants were selected on EMM with all the required supplements omitting ura. Twenty-five transformants were selected and analyzed by Southern blotting for a disruption of SpPCS. Transformants with a disruption of the SpPCS gene were identified by the appearance of a second band due to the EcoRV site in the ura4 gene. Non-homologous insertion of the knockout construct led to a third band hybridizing with the SpPCS probe.

Phytochelatin assay

Phytochelatins were assayed essentially as described (Fahey and Newton, 1987, Meth. Enzymol. 143:85–97). Briefly, *S. pombe* and *S. cerevisiae* cells were grown to mid-log phase (in EMM-ura, YNB-ura, respectively) and treated with 100 μM $Cd^{2+}$. Six hours after $Cd^{2+}$ addition, the cells were harvested and they were lyophilized. One to five mg of the lyophilized material were extracted in 0.1% TFA, the sample was centrifuged and the supernatant was derivatized with monobromobimane at 45° C. in the dark. The extracts were separated by HPLC on a C18 column (3 μM, 150 mm) using an acetonitrile gradient. SH-containing compounds were detected fluorimetrically. For the identification of phytochelatins, (γ-EC)$_2$G (=PC2), (γ-EC)$_3$G (=PC3) and (γ-EC)$_4$ (=PC4), standards were synthesized on an Abimed (Langenfeld, Germany) Economy Peptide Synthesizer EPS 211 using N-α-Fmoc-L-glutamic acid α-butyl ester (Novabiochem, Läufelfingen, Switzerland).

Protein extraction from *S. pombe*

Protein was extracted from *S. pombe* cultures grown to mid-log phase in EMM essentially as described (Hayashi et al., 1991, Biochem. Cell Biol. 69:115–121). In brief, cells were harvested by centrifugation. The cell pellet was frozen in liquid $N_2$ and ground in a chilled mortar using three volumes of quartz sand. Following extraction with 50 mM Tris-Cl, pH 8.0, 10% glycerol, 150 mM, NaCl, 1 mM DTT, 1 mM PMSF, 10 μM leupeptin and centrifugation at 10,000×g for 15 minutes, ammonium sulphate was added to the supernatant to 75% saturation. After 30 minutes, the precipitate was collected by centrifugation at 18,000×g for 15 minutes and was dissolved in 25 mM Tris-Cl (pH 8.0), 10% glycerol, and 1 mM DTT.

Phytochelatin synthase assay

Aliquots of crude extracts or column fractions were incubated in 200 mM Tris-Cl (pH 8.0), 1 mM DTT, 1 mM GSH (total volume 100 μl). The assay mixtures were kept on ice for 5 minutes. $CdCl_2$ was added to a final concentration of 0.1 mM and the samples were incubated at 35° C. for 30–120 minutes. At the end of the incubation period, 50 μl aliquots were taken and TFA was added to a concentration of 5%. Following a 10 minute incubation on ice and 10 minutes of centrifugation at 13,000×g, aliquots of the supernatant were derivatized with monobromobimane and were analyzed by HPLC as described above.

Purification of HA-tagged SpPCS

SpPCS was subcloned into pSGP73 to express SpPCS protein with an N-terminal HA tag using the knock-out strain. The crude extract from a 200 ml culture of SpPCS-HA-expressing cells grown to mid-log phase in EMM without leucine and uracil was incubated with 600 μl of HA-monoclonal antibody affinity matrix slurry (BAbCo, Berkeley, Calif.) at 4° C. under gentle shaking. After 3 hours, the mixture was transferred to a column and the matrix was allowed to settle. Subsequently, the column was washed with 20 ml 50 mM Tris-Cl, pH 8.0, 10% glycerol, 150 mM NaCl, 1 mM DTT. HA-tagged protein was eluted at 30° C. with 5 mg HA peptide dissolved in 5 ml wash buffer. The protein fractions were analyzed by SDS-PAGE followed by silver staining and Western blotting using established procedures (Ausubel et al., 1997, supra).

The Results of the experiments presented in this example are now described.

Cloning of TaPCS1

A screening assay was used to identify plant genes that confer cellular $Cd^{2+}$ tolerance. Yeast cells were transformed with a size-selected (about greater than 1.5 kb) wheat root library (Schachtman and Schroeder, 1994, Nature 370:655–658) and $2 \times 10^7$ cells representing approximately $1 \times 10^6$ independent transformants were added to 50 ml of arginine-phosphate liquid medium containing either 20 or 50 μM $Cd^{2+}$. These $Cd^{2+}$ concentrations are growth-inhibiting for yeast cells in arginine-phosphate medium. However, the liquid cultures were growth-saturated within 2–4 days. Following saturation, surviving yeast cell aliquots were taken, DNA was extracted from these survivors and, after *E. coli* transformation, the pYES2 inserts of the survivors were analyzed.

All inserts from the same culture exhibited identical restriction patterns indicating that the liquid cultures grew to saturation starting from one or a small number of yeast cells containing the same wheat cDNA. In six liquid cultures of this screen (which included two repetitions with newly transformed cells), a single cDNA, differing only in the length of the 5' untranslated regions (UTRs), was cloned. The cDNA was initially named CdR (for $Cd^{2+}$ Resistance) but after further characterization, the nucleic acid was named TaPCS1 for its function in *Triticum aestivum* phytochelatin synthesis.

TaPCS1 expression makes *S. cerevisiae* more $Cd^{2+}$ tolerant

Figure 8A:
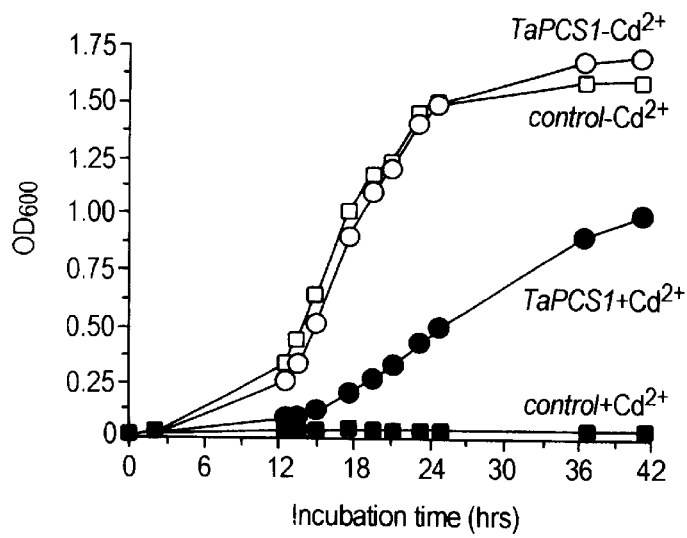
FIG. 8A is a graph depicting that TaPCS1 expression renders yeast cells more $Cd^{2+}$ tolerant. Control INVSc1 cells (Invitrogen, Carlsbad, Calif.) carrying the empty pYES2 plasmid (squares) and cells expressing TaPCS1 (circles) were grown in YNB (1% sucrose/1% galactose) containing-either no $Cd^{2+}$ (open symbols) or 200 µM $Cd^{2+}$ (filled symbols).
Figure 8B:
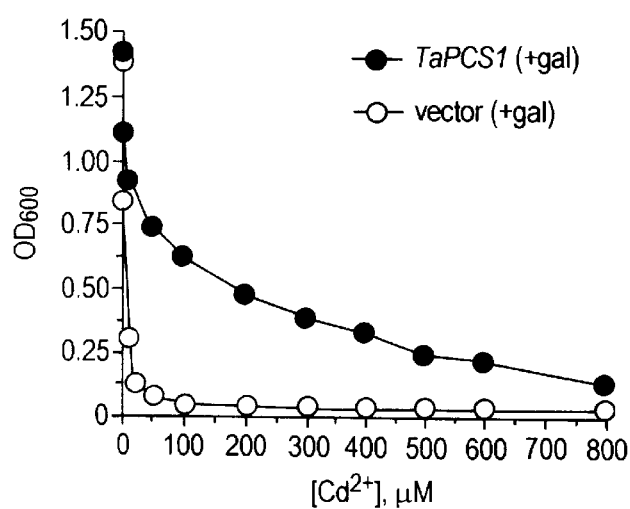
FIG. 8B is a graph depicting the growth of yeast cells in YNB (1% sucrose/1% galactose) of control cells (open circles) and TaPCS1 expressing cells (filled circles) at different $Cd^{2+}$ concentrations. Cell growth, measured as the optical density of the cultures at 600 nm ($OD_{600\,nm}$) after 24 hours growth, is shown.

TaPCS1 expression mediated a dramatic increase in $Cd^{2+}$ tolerance of *S. cerevisiae* cells. TaPCS1-expressing cells grew to saturation in the presence of $Cd^{2+}$ concentrations that completely inhibited growth of control cells harboring the empty pYES2 plasmid (FIG. 8A). Dose-response analyses demonstrated that TaPCS1-expressing cells tolerate 15-fold higher $Cd^{2+}$ concentrations than control cells (FIG. 8B) {$K_{0.5}$(TaPCS1)=90 μM $Cd^{2+}$; $K_{0.5}$(control)=6 μM $Cd^{2+}$}. TaPCS1-expressing cells grown in the absence of the inducer galactose also displayed a strong degree of $Cd^{2+}$ tolerance, suggesting that low levels of TaPCS1 are sufficient for $Cd^{2+}$ resistance and indicating a catalytic role of TaPCS1 in mediating $Cd^{2+}$ tolerance (FIG. 8C), rather than tolerance by direct binding of metals to TaPCS1. Even with glucose as the carbon source, which represses the GAL1 promoter, a slight enhancement of growth was seen in TaPCS1 containing cells, further suggesting a catalytic activity of TaPCS1.

Sequence analysis and TaPCS1 homologs

Figure 9A:
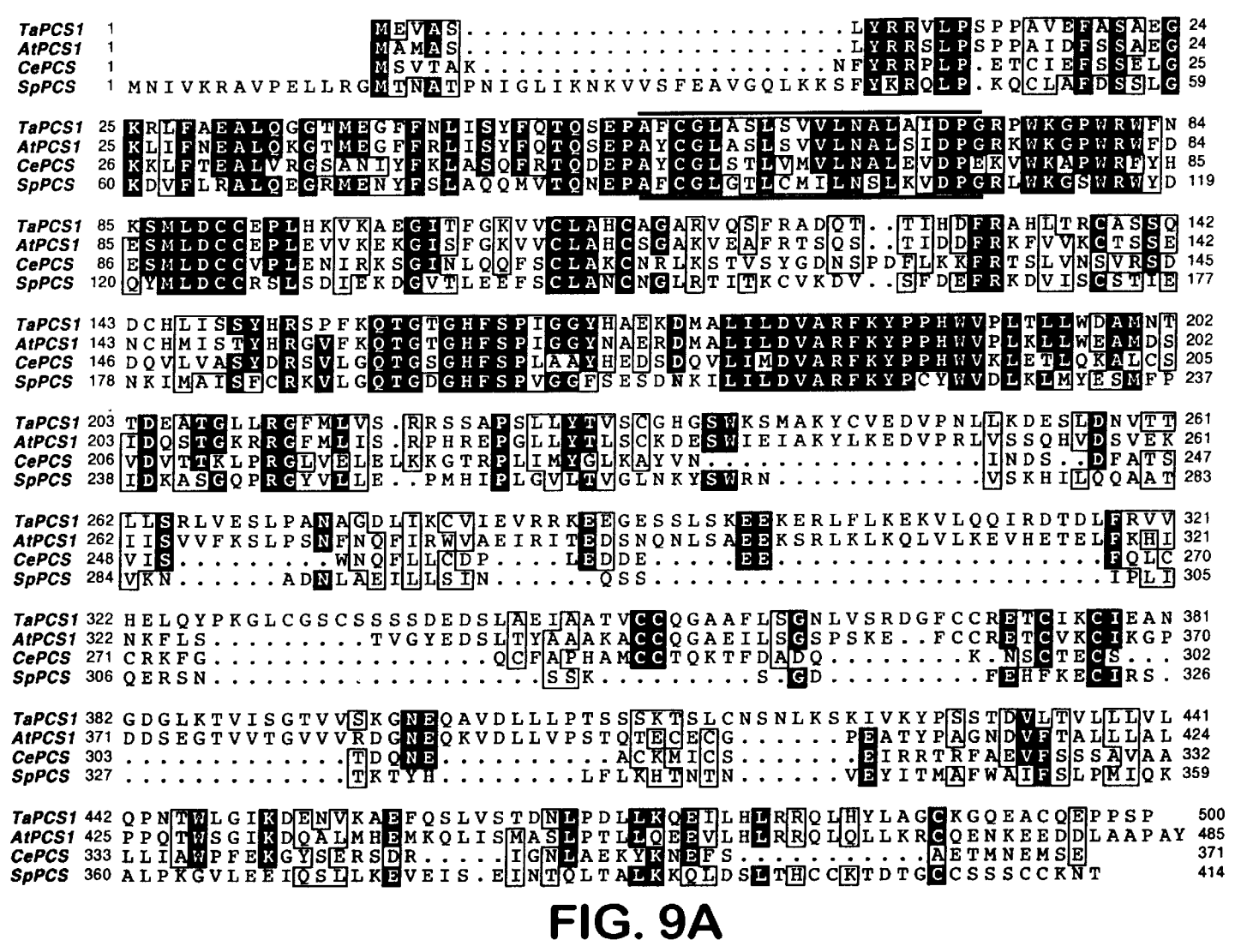
Figure 9B:
FIG. 9B is an image of a photograph depicting the growth of control cells (carrying the empty pYES2 plasmid) and of cells expressing either TaPCS1, AtPCS1 or SpPCS on YNB medium without (left) and with 100 µM $Cd^{2+}$ (middle). The drawing at the far right of the figure depicts the position on each plate at which the respective yeast transformants were streaked.

The TaPCS1 open reading frame (ORF; GenBank Accession AF093752) encodes a polypeptide of a predicted mass of 55 kDa (FIG. 9A). The deduced amino acid sequence (SEQ ID NO: 6; FIG. 9A) shows no homology to any protein of known function. However, homology was found for the *Arabidopsis thaliana* EST G11G3T7 (GenBank W43439), a *Schizosaccharomyces pombe* hypothetical 46.7 kDa protein C3H1.10 (GenBank Z68144), and the *Caenorhabditis elegans* ORF F54D5.1 (GenBank Z66513). These sequences are 55%, 28%, and 32% identical at the amino acid level, respectively (FIG. 9A). TaPCS1 and its homologs thus constitute a new gene family. The homologs from Arabidopsis (AtPCS1) and *S. pombe* (SpPCS) also confer strong $Cd^{2+}$ tolerance when expressed in *S. cerevisiae* (FIG. 9B). Low-stringency DNA gel blot analysis in Arabidopsis suggests the presence of more than one AtPCS homolog (see Example 1, supra). Meanwhile, a second Arabidopsis gene (AtPCS2, GenBank AC003027, see Example 1) and a second *C. elegans* gene (GenBank AL023633) with homology to the PCS genes have been identified through genome sequencing efforts.

TaPCS1 mediates an increase in $Cd^{2+}$ accumulation

Figure 10:
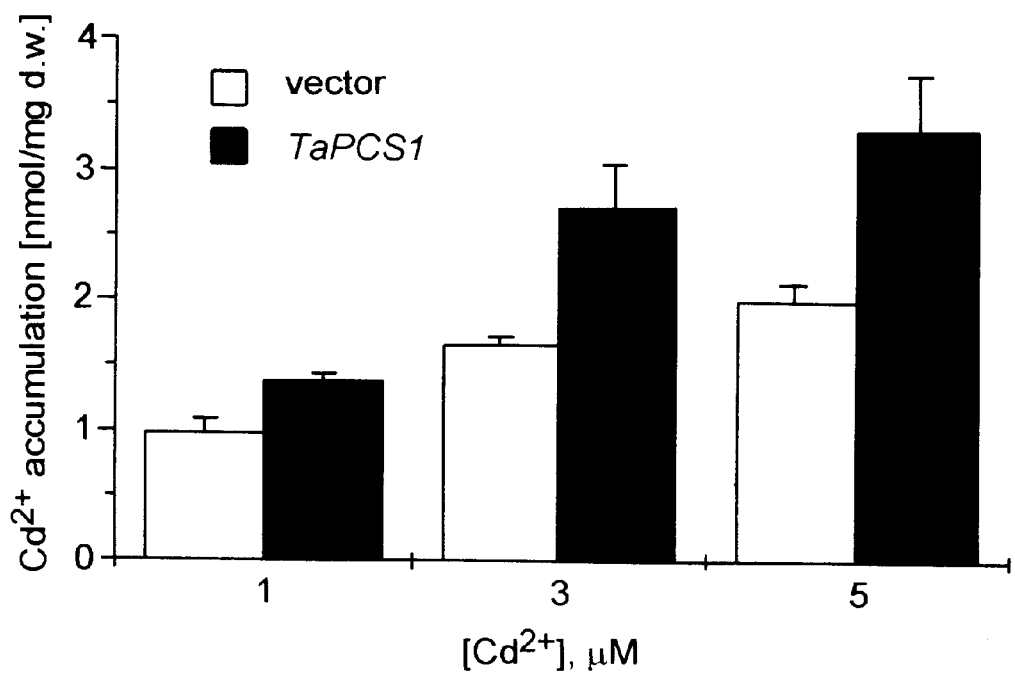
FIG. 10 is a graph depicting the greater accumulation of $Cd^{2+}$ by cells expressing TaPCS1 compared to the $Cd^{2+}$ accumulation by control cells. Yeast cells carrying the empty pYES2 plasmid (white bars) and TaPCS1-expressing cells (black bars) were grown in arginine-phosphate medium containing different non-inhibitory $Cd^{2+}$ concentrations. After 24 hours, the cells were harvested and washed and the amount of $Cd^{2+}$ accumulated inside the cells was determined using $^{109}Cd^{2+}$ (Error bars=S.E., n=3).

One possible mechanism underlying $Cd^{2+}$ tolerance is an efflux of $Cd^{2+}$ ions as observed in many bacteria (Silver and Phung, 1996, Annu. Rev. Microbiol. 50:753–789). This possibility was investigated by measuring the accumulation of $Cd^{2+}$ by control and TaPCS1-expressing cells grown at $Cd^{2+}$ concentrations that do not significantly affect the growth even of control cells. As shown in FIG. 10, TaPCS1 expression led to an increase in $Cd^{2+}$ accumulation by about 30–50% during a 24 hour culture period (n=3). Similar results were obtained for the Arabidopsis homolog (n=2). These data are evidence in support of PCS-dependent $Cd^{2+}$ chelation or sequestration.

TaPCS1 confers $Cd^{2+}$ tolerance even in vacuolar mutants

Figure 11:
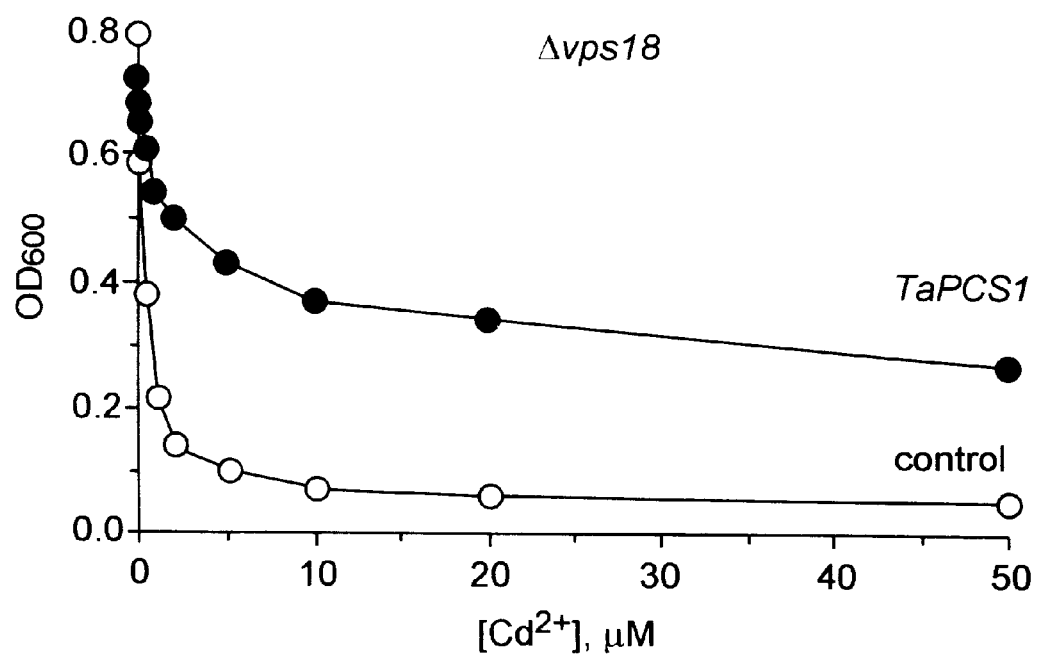
FIG. 11 is a graph depicting that the expression of TaPCS1 in Δvps18, a S. cerevisiae strain lacking morphologically visible vacuoles (Robinson et al., 1991, Mol. Cell. Biol. 11:5813–5824), still confers a $Cd^{2+}$ tolerance phenotype. Cells carrying the empty pYES2 plasmid (open circles) and cells expressing TaPCS1 (closed circles) were grown in YNB medium in the presence of different $Cd^{2+}$ concentrations.

Sequestration of $Cd^{2+}$ and other heavy metal ions into vacuoles is a well-characterized mechanism of detoxification (Rea et al., 1998, Plant Mol. Biol. 49:727–760). One postulated pathway for plants that would function parallel to the transport of Cd-phytochelatin complexes into vacuoles is a $Cd^{2+}$/H+ exchanger (Salt and Wagner, 1993, J. Biol. Chem. 268:12297–12302). To determine whether TaPCS1 is involved in this process TAPCS1 was expressed in a Δvma4 strain, which lacks a functional vacuolar ATPase and therefore cannot establish a pH gradient (Ho et al., 1993, J. Biol. Chem. 268:221–227) required for $Cd^{2+}$ uptake via the $Cd^{2+}$/H+ exchanger. Growth assays with the Δvma4 and the parental strain showed that TaPCS1 still confers $Cd^{2+}$ tolerance (n=3). Furthermore, TaPCS1 was expressed in the yeast strain Δvps18, which fails to form any structures morphologically resembling normal vacuoles (Robinson et al, 1991, Mol. Cell. Biol. 11:5813–5824). This strain is significantly more sensitive to $Cd^{2+}$ than the parental strain (FIG. 11, open circles). Interestingly, TaPCS1 expression again led to a strong increase in $Cd^{2+}$ tolerance (FIG. 11, filled circles).

SpPCS deletion results in metal sensitivity

Figure 12A:
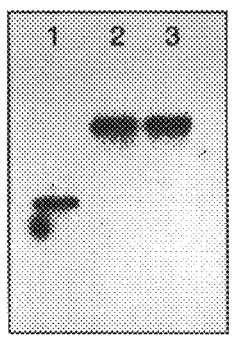
FIG. 12A is an image depicting a Southern blot demonstrating a S. pombe strain with a disruption of SpPCS exhibits increased metal sensitivity. The low-stringency Southern blot of S. pombe genomic DNA was probed with SpPCS. The lanes were loaded with DNA digested with: BamHI (lane 1), HindIII (lane 2), and EcoRI (lane 3).
Figure 12B:
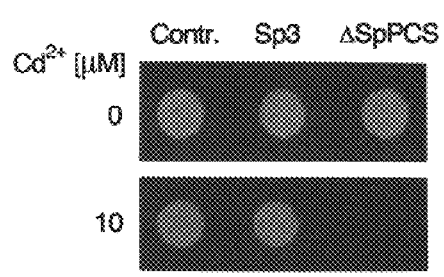
FIG. 12B is an image of a photograph depicting the growth of a SpPCS knockout strain (ΔSpPCS) and, as controls, a strain transformed with the empty plasmid pTZura4 and a transformant with a non-homologous integration of the knockout construct (Sp3). The transformants were grown on EMM-ura containing either 0 or 10 µM $Cd^{2+}$.
Figure 12C:
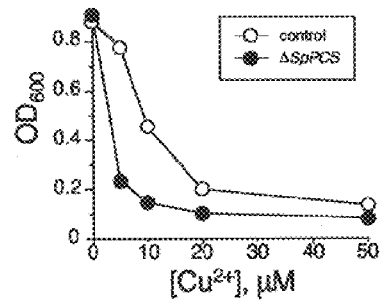
FIG. 12C is a graph depicting the growth of the marker-transformed control strain (open circles) and the ΔSpPCS strain (filled circles). The strains were grown in liquid EMM-ura in the presence of different $Cu^{2+}$ concentrations, and the OD was measured after 24 hours of growth.

To investigate the physiological role of the PCS genes more directly, a deletion mutant of SpPCS, dSpPCS, was generated in *S. pombe*. First, Southern analysis of *S. pombe* genomic DNA was performed to search for additional PCS homologs. Under low-stringency conditions, no indication of sequences homologous to SpPCS could be detected (FIG. 12A), demonstrating that SpPCS is a single-copy gene in this organism. Subsequently, the SpPCS gene was deleted by a one-step gene disruption using the ura4 marker. The $Cd^{2+}$ sensitivity of *S. pombe* with a disruption of the SpPCS gene (ΔSpPCS) was tested in media containing various $Cd^{2+}$ concentrations. For controls, a.strain transformed with the empty plasmid pTZura4 and a transformant with a non-homologous integration of the knockout construct (Sp3) were analyzed. In the absence of $Cd^{2+}$, the knockout strain grew normally (FIG. 12B). Growth of the knockout strain was more strongly inhibited by $Cd^{2+}$ than that of the two different control strains that were indistinguishable (FIG. 12B). Growth of the knockout strain was also more sensitive than control strains to copper (FIG. 12C) demonstrating a role for SpPCS in resistance to Cu2+.

PCS genes are involved in phytochelatin synthesis

Figure 13A:
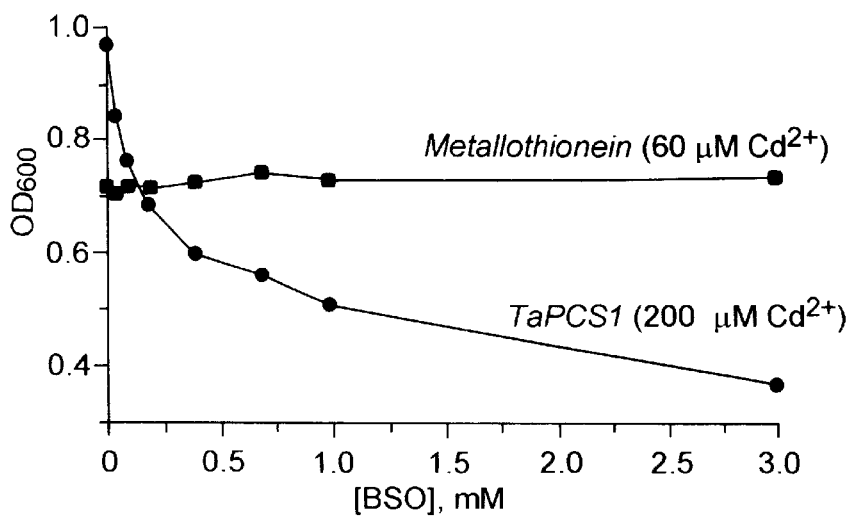
FIG. 13A is a graph depicting phytochelatin synthesis in cells expressing PCS. The growth of S. cerevisiae cells expressing either TaPCS1 (circles) or an Arabidopsis metallothionein (squares) in the presence of $Cd^{2+}$ (200 µM for TAPCS1 and 60 µM for metallothionein) following a 6 hour preincubation using different concentrations of BSO (L-Buthionine-sulfoxime), a glutathione synthesis inhibitor. The OD was measured 18 hours after the addition of $Cd^{2+}$.

The findings indicating a catalytic role of the PCS genes in $Cd^{2+}$ sequestration (FIG. 8C) suggested a possible role for the PCS gene family in phytochelatin synthesis. Glutathione is a precursor required for phytochelatin synthesis (Grill et al., 1989, Proc. Natl. Acad. Sci. USA 86:6838–6842). Pretreatment of TaPCS1-expressing S. cerevisiae with the glutathione biosynthesis inhibitor BSO (L-Buthionine-sulfoxime) reduced the TaPCS1-mediated $Cd^{2+}$ tolerance in a dose-dependent manner (FIG. 13A, filled circles). In controls, expression of an Arabidopsis metallothionein exhibited no effect of BSO on metallothionein-dependent $Cd^{2+}$ tolerance (FIG. 13A, filled squares). TaPCS1 expressing cells exhibited a significantly higher.growth rate at 200 $\mu$M $Cd^{2+}$ than that of metallothionein-expressing cells at only 60 $\mu$M $Cd^{2+}$ (FIG. 13A).

Figure 13B:
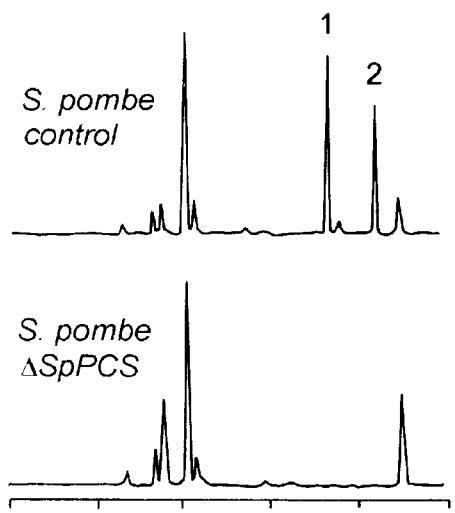
FIG. 13B is a graph (comprising two panels) depicting the HPLC analysis of extracts of $Cd^{2+}$-treated S. pombe wild-type cells (control, top panel) and S. pombe knockout cells (ΔSpPCS, bottom panel) labeled with monobromobimane and analyzed by HPLC using a reversed-phase column and fluorescence detection. The peaks labeled 1 and 2 are identical to those depicted in FIG. 13C based on co-injection experiments. These peaks represent PC2 and PC3 as demonstrated by comparison of retention times with standards synthesized on an Abimed peptide synthesizer (as described elsewhere herein).
Figure 13C:
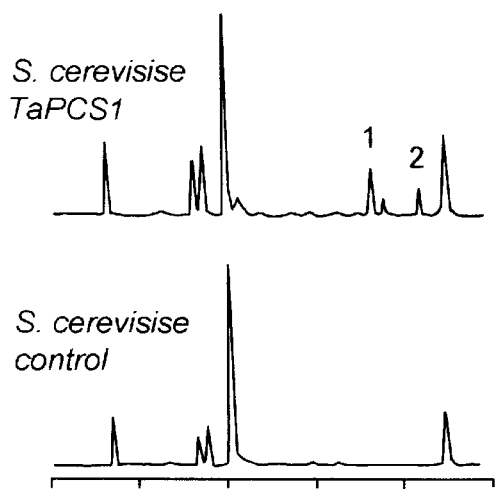
FIG. 13C is a graph (comprising two panels) depicting the HPLC analysis of extracts of $Cd^{2+}$-treated S. cerevisiae cells expressing TaPCS1 (top panel) and *S. cerevisiae* wildtype (bottom panel) labeled with monobromobimane and analyzed by HPLC using a reversed-phase column and fluorescence detection. The peaks labeled 1 and 2 are identical to the peaks labeled 1 and 2 in FIG. 13B, supra, based on co-injection experiments. They represent PC2 and PC3 as shown by comparison of retention times with standards synthesized on an Abimed peptide synthesizer (as described elsewhere herein).

Wildtype S. pombe cells (control) and the ΔSpPCS strain were analyzed for phytochelatin synthesis upon $Cd^{2+}$ exposure by fluorescence HPLC. Peaks demonstrating retention times identical to the synthesized phytochelatin standards, PC2 and PC3, were detected in extracts from wildtype cells (FIG. 13B, top panel, peaks 1 and 2) but were absent in extracts from ΔSpPCS cells (FIG. 13B, bottom panel). Thus, the increased $Cd^{2+}$ sensitivity of the S. pombe knockout is correlated with a deficiency in phytochelatin synthesis. Furthermore, TaPCS1-expressing S. cerevisiae cells synthesized compounds following $Cd^{2+}$ treatment (FIG. 13C, top panel) that were not formed in wildtype cells (FIG. 13C, bottom panel). Those compounds demonstrated retention times identical to PC2 and PC3 which were not observed in the S. cerevisiae controls, demonstrating that TaPCS1 expression is sufficient to elicit the synthesis of PCs in an organism proposed not to normally form PCs (Rauser, 1995, Plant Physiol. 109:1141–1149). PC synthesis in TaPCS1-expressing cells can also be elicited by treatment with $Cu^{2+}$ or $Zn^{2+}$.

PCS proteins catalyze phytochelatin synthesis

PCS enzyme assays with crude extracts from S. pombe marker-transformed cells and ΔSpPCS cells demonstrated that the knock-out strain lacks PCS activity (FIG. 14A, bottom panel). In extracts from control cells, PC2 formation from glutathione was clearly detectable (FIG. 14A, top panel), similar to previous reports using purified enzyme preparations (Grill et al., 1989, Proc. Natl. Acad. Sci. USA 86:6838–6842; Hayashi et al., 1991, Biochem. Cell Biol. 69:115–121). Thus, the ASpPCS strain provided a suitable background for the expression of a tagged SpPCS protein in order to demonstrate directly that the PCS proteins catalyze phytochelatin synthesis. SpPCS was expressed comprising an N-terminal hemagglutinin (HA)-tag (SpPCS-HA) in the knock-out strain and this construct restores metal tolerance, PCS enzyme activity, and the ability to form PC2 and PC3. Western blots of extracts from cells expressing- the HA-tagged SpPCS protein demonstrate a band at about 46 kDa, corresponding to the predicted molecular weight of SpPCS, which is recognized by a monoclonal anti-HA antibody (BAbCo, Berkeley, Calif.; FIG. 14B, left lane). No signal was detected in extracts from control cells containing the empty pSGP73 plasmid (FIG. 14B, right lane).

SpPCS-HA was purified using the monoclonal HA-antibody coupled to sepharose (BAbCo, Berkeley, Calif.). The fraction eluted with synthesized HA peptide (YPYDVPDYA) was analyzed by SDS polyacrylamide gel electrophoresis. Silver staining of the gel demonstrated two bands, one at about 46 kDa, the same as found for the anti-HA-immunoreactive band detected from extracts of SpPCS-HA expressing cells, and a lower molecular weight band of approximately 30 kDa (FIG. 14C, left panel). Western blot analysis of the eluate fraction demonstrated cross-reactivity of both polypeptides to anti-HA antibodies (FIG. 14C, right panel). Recognition of the 30 kDa protein by anti-HA antibodies, combined with the fact that this band was not detected from lysates of SpPCS-HA expressing and control cells (FIG. 14B), suggest, without wishing to be bound by theory, that the polypeptide might represent a proteolytic degradation product of the 46 kDa protein which may have arisen during purification.

Aliquots of the peptide eluate were further analyzed for PCS enzyme activity. As shown in FIG. 14D, HPLC analysis of the monobromobimane-derivatized reaction products shows formation of a peak corresponding to PC2 from glutathione and $Cd^{2+}$, thereby demonstrating PCS enzyme activity in the fraction containing SpPCS-HA.

TaPCS1expression is constitutive and is enhanced by $Cd^{2+}$

Figure 15:
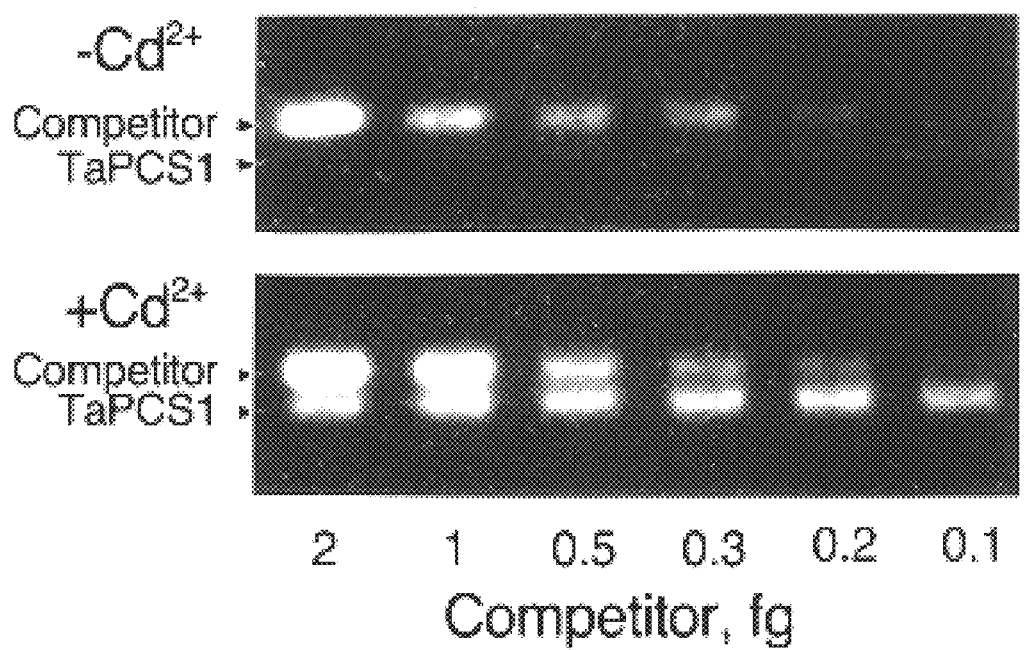
FIG. 15 is an image (comprising three panels) of a gel depicting that TaPCS1 expression in roots is induced by $Cd^{2+}$ as demonstrated using competitive PCR. RNA was isolated from 4 day old wheat roots that were either untreated or treated with 100 μM $Cd^{2+}$ for 6 hours. First-strand cDNA was synthesized and 10 ng were used as template in PCR reactions. The competitor DNA used in this study was a PCR fragment amplified from genomic DNA that was approximately 100 bp longer than the cDNA-amplified fragment because of the presence of an intron. The indicated amounts of competitor DNA were added. The aliquots were analyzed by agarose gel electrophoresis. The experiment was repeated twice with similar results.

TaPCS1 mRNA could not be detected by RNA blot analysis of wheat root mRNA. To determine whether the TaPCS1 gene is transcribed in wheat seedlings, RT-PCR analysis was performed using TaPCS1 specific primers. Fragments of the expected size were detectable for both root (FIG. 15, top panel) and shoot samples. Expression of AtPCS1 in Arabidopsis was also analyzed by RT-PCR. The results in Arabidopsis were the same as found for TaPCS1, demonstrating that both TaPCS1 and AtPCS1 are transcribed in vivo. To determine whether exposure to $Cd^{2+}$ treatment affected TaPCS1expression in wheat, wheat cDNA was used together with different amounts of competitor DNA in PCR reactions. Comparison of the band intensity indicated a 5–10 fold higher concentration of TaPCS1 message in wheat roots treated with 100 $\mu$M $Cd^{2+}$ (FIG. 15).

The data disclosed herein demonstrate the isolation and functional characterization of a novel family of genes in several different organisms that mediate a dramatic increase in $Cd^{2+}$ tolerance when expressed in S. cerevisiae. Cadmium accumulation experiments, TaPCS1 induction in roots, glutathione inhibitor studies, and analysis in several yeast mutant backgrounds, together with the $Cd^{2+}$ and $Cu^{2+}$ sensitivity of a SpPCS disruption mutant in S. pombe demonstrate a central physiological role of the PCS gene family for metal tolerance. The PC deficiency of a S. pombe knockout strain, the PC synthesis observed in TaPCS1-expressing S. cerevisiae cells upon $Cd^{2+}$ exposure and the phytochelatin synthase activity of purified recombinant SpPCS suggest that these genes mediate PC synthesis.

TaPCS1 was identified through an expression cloning strategy in S. cerevisiae, by searching for clones mediating high tolerance to $Cd^{2+}$ in the growth medium. TaPCS1 expression enabled yeast cells to grow at more than 15-fold higher $Cd^{2+}$ concentrations than control cells. Identification of TaPCS1 using this approach was greatly enhanced by the fact that the screening was restricted to a cDNA size fraction (greater than about 1.5 kb) of a cDNA library (Schachtman and Schroeder, 1994, Nature 370:655–658), which helped-eliminate the cloning of cDNAs encoding small and abundant heavy metal-binding peptides such as metallothioneins. Selection of transformants exhibiting elevated tolerance to $Cd^{2+}$ was performed in liquid medium in order to provide extremely homogeneous screening conditions, while easily permitting the screen to be performed in parallel under different levels of selective pressure. This screening method also allowed the isolation of those cDNAs most effective in conferring $Cd^{2+}$ tolerance. The efficacy of this approach is demonstrated by the fact that, in many independent experiments, TaPCS1was the only cDNA isolated.

A role in metal tolerance

Figure 8C:
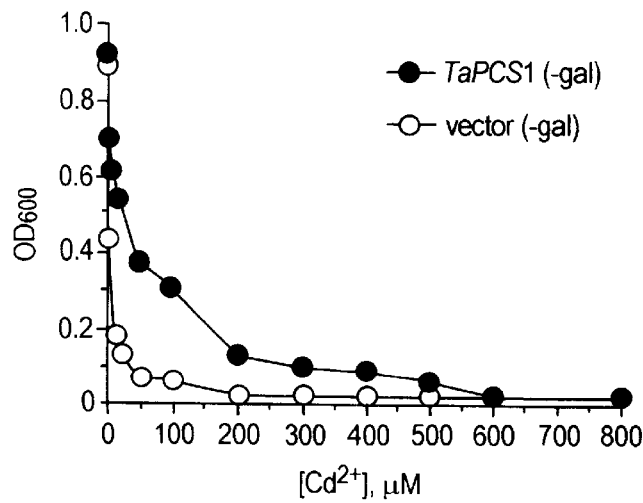
FIG. 8C is a graph depicting the growth in YNB (2% raffinose) of control cells (open circles) and TaPCS1 expressing cells (filled circles) at different $Cd^{2+}$ concentrations. $OD_{600\,nm}$ of cultures after 40 hours is shown.

A number of findings suggest a catalytic role of the PCS gene products in metal detoxification. The observed increase in $Cd^{2+}$ accumulation (FIG. 10) upon TaPCS1 expression in S. cerevisiae demonstrated that the tolerance phenotype is not based on the exclusion of the toxic metal, the dominant mechanism- of metal detoxification in bacteria (Silver and Phung, 1996, Annu. Rev. Microbiol. 50:753–789). On the contrary, the TaPCS1-dependent increase in $Cd^{2+}$ accumulation is consistent with the hypothesis that TaPCS1 is involved in $Cd^{2+}$ sequestration as, for instance, S. pombe cells overexpressing the ABC type transporter hmt1 accumulate more $Cd^{2+}$ (Ortiz et al., 1992, EMBO J. 11:3491–3499). Furthermore, TaPCS1 can confer strong $Cd^{2+}$ tolerance even when expressed at low levels under non-inducing conditions (FIG. 8C).

Because most toxic materials inside plant cells are sequestered in vacuoles, $Cd^{2+}$ sensitivity assays were performed using yeast vacuolar mutants. The TaPCS1-mediated increase in $Cd^{2+}$ tolerance which was still observed in yeast strains that lack either a functional V-ATPase (Ho et al., 1993, J. Biol. Chem. 268:221–227) or in yeast which lack morphologically typical discernible vacuoles (Robinson et al, 1991, Mol. Cell. Biol. 11:5813–5824; FIG. 11) led to the conclusion that a direct role for TaPCS1 in vacuolar transport of $Cd^{2+}$ ions appears unlikely, although an indirect involvement or early reaction preceding vacuolar uptake cannot be ruled out.

The PCS genes mediate phytochelatin synthesis

Synthesis of phytochelatins from glutathione upon metal exposure has been shown to be directly involved in plant metal tolerance (Zenk, 1996, Gene 179:21–30). Phytochelatin synthase was proposed to catalyze the first step in the sequestration of $Cd^{2+}$ as Cd-phytochelatin complexes in vacuoles. Because a cDNA encoding a phytochelatin synthase had not been isolated and because the data disclosed herein suggested a PCS-mediated sequestration of $Cd^{2+}$, the involvement of the PCS genes in PC synthesis was examined.

Consistent with the aforementioned observations in plants, $Cd^{2+}$ hypersensitive mutants of S. pombe have been isolated which show reduced phytochelatin levels (Mutoh and Hayashi, 1988, Biochem. Biophys. Res. Commun. 151:32–39). Thus, the observed $Cd^{2+}$ hypersensitivity of the ASpPCS strain (FIG. 13B) provided further indication for the hypothesis that PCS genes directly mediate phytochelatin synthesis. Copper sensitivity is also consistent with a PC deficiency as phytochelatins form complexes with several toxic metals and with copper ions as well (Rauser, 1995, Plant Physiol. 109:1141–1149).

To test more directly the hypothesis that PCS genes mediate phytochelatin synthesis, the effect of BSO, a potent, specific inhibitor glutathione biosynthesis, on TaPCS1-mediated $Cd^{2+}$ tolerance was determined. BSO has been previously shown to reduce synthesis of PCs and PC-associated $Cd^{2+}$ tolerance in plant cell cultures (Steffens, 1990, Plant Mol. Biol. 41:553–575). The BSO-dependent reduction in $Cd^{2+}$ tolerance of TaPCS1 expressing S. cerevisiae cells (FIG. 13A) demonstrated a role for glutathione biosynthesis on TaPCS1-mediated $Cd^{2+}$ resistance. In contrast, control cells overexpressing metallothioneins showed no BSO sensitivity and less $Cd^{2+}$ resistance (FIG. 13A).

Subsequently, HPLC analysis of monobromobimane-labeled extracts from $Cd^{2+}$-treated wildtype S. pombe exhibited the expected peaks for PC2 and PC3, the dominant phytochelatins of fission yeast (Kondo et al., 1985, Agric. Biol. Chem. 49:71–83; FIG. 6B, top, peaks 1 and 2). PC2 and PC3 were undetectable in extracts of $Cd^{2+}$-treated ASpPCS cells (FIG. 13B, bottom). Correspondingly, no PCS enzyme activity was detectable in protein extracts of the knock-out strain (FIG. 14A, bottom), thereby establishing a role for SpPCS in phytochelatin synthesis. Furthermore, extracts of S. cerevisiae control cells did not show formation of PC peaks in the present study (FIG. 13C, bottom). Notably, the S. cerevisiae genome contains no PCS homologs (Mewes et al., 1997, Nature 387:7–65). In contrast, TaPCS1-expressing S. cerevisiae cells formed PC2 and PC3 upon $Cd^{2+}$ exposure (FIG. 13C, top). Thus, TaPCS1 expression is concluded to be sufficient for phytochelatin synthesis from glutathione in an organism whose genome does not contain a PCS homolog (Mewes et al., 1997, Nature 387:7–65). S. cerevisiae has been reported to express only limited quantities of exclusively PC2 (Kneer et al., 1992, Arch. Microbiol. 157:305–310), an activity which clearly differs from that observed in TaPCS1-expressing cells, which mediates PC2 and PC3 synthesis. To demonstrate the direct catalysis of phytochelatin synthesis by the PCS proteins, a ASpPCS strain was used as a null background for the expression and purification of a tagged version of SpPCS. Phytochelatin synthesis from glutathione was detectable in fractions eluted from a HA-antibody affinity matrix that contained no detectable protein other than the HA-tagged SpPCS and an apparent degradation product (FIG. 14). These data demonstrate the direct catalysis of phytochelatin synthesis by the PCS proteins. On the basis of these results, the data disclosed herein demonstrate that the PCS genes encode phytochelatin synthases.

Phytochelatin synthase was previously reported by (Grill et al., 1 989, Proc. Natl. Acad. Sci. USA 86:6838–6842) to be a 95 kDa tetramer. The predicted molecular mass of the PCS proteins described here lies in range of 46–55 kDa. Without wishing to be bound by theory, it cannot be ruled out that the PCS genes disclosed herein encode catalytic subunits of a multimeric PC synthase.

Phytochelatins are involved in metal tolerance in vivo

The data disclosed herein concerning the metal sensitivity of the ASpPCS strain provide molecular evidence that phytochelatins play a central role in metal detoxification in plants and S. pombe. Furthermore, the data disclosed herein demonstrate that lack of PC synthesis also leads to Cu hypersensitivity. This provides evidence for a more general role of phytochelatins in metal homeostasis, as was suggested earlier (Rauser, 1990, Annu. Rev. Biochem. 59:61–86) and indicated by the finding that PC-metal complexes can activate metal-depleted apoenzymes in vitro (Thumann et al., 1991, FEBS Lett. 284:66–69).

Consistent with the reported constitutive activity of phytochelatin synthase (Grill et al., 1989, Proc. Natl. Acad. Sci. USA 86:6838–6842) in roots and stems (Chen et al., 1997, Physiol. Plant. 101:165–172) and the suggested requirement for organisms to express metal tolerance genes constitutively (Zenk, 1996, Gene 179:21–30), TaPCS1 and AtPCS1 message were detected in roots and shoots of non-metal-stressed wheat and Arabidopsis plants, respectively. Furthermore, competitive PCR experiments using $Cd^{2+}$-treated wheat roots and TaPCS1 show metal-induced up-regulation of PCS mRNA levels (FIG. 15). $Cd^{2+}$-induced increases in PCS activity have been previously reported by Chen et al. (1997, Physiol. Plant. 101:165–172) for tomato cell lines.

Heterologous expression of PCS genes is sufficient to enhance metal tolerance

In the models proposed for phytochelatin-mediated $Cd^{2+}$ complexation (Ortiz et al., 1995, J. Biol. Chem. 170:4721–4728; Rauser, 1995, Plant Physiol. 109:1141–1149), PCs function as cytosolic chelators and carriers of $Cd^{2+}$ ions by forming low-molecular weight complexes which are then transported into the vacuole by transporters such as the ABC-type transporter HMT1 in *S. pombe* (Ortiz et al., 1992, EMBO J. 11:3491–3499). Inside the vacuole, more $Cd^{2+}$ and sulfide are added to the complex to produce the high-molecular weight complexes which are believed to represent the sequestered form of $Cd^{2+}$.

The cloning of TaPCS1 and growth assays with *S. cerevisiae* cells expressing TaPCS1, ΔAtPCS1 and SpPCS demonstrated that phytochelatin synthesis alone can significantly increase cellular $Cd^{2+}$ tolerance (FIGS. 8 and 10). Taken together with the evidence disclosed elsewhere herein for vacuole-independent TaPCS1-mediated $Cd^{2+}$ tolerance obtained from experiments with the Δvps18 mutant (FIG. 11), this suggests that PCs represent a significant cytosolic buffer for metal ions. These data and the unexpected finding of two PCS homologs in the Caenorhabditis elegans genome raise the possibility that PC synthase overexpression could be successfully used to increase the metal tolerance of diverse organisms. Furthermore transgenic PCS expression could be useful for enhancing the removal of toxic metals by plants and other organisms for bioremediation.

Thus, the data disclosed herein demonstrate the isolation of a novel family of metal tolerance genes from a wide variety of organisms that encode phytochelatin synthases, as demonstrated by glutathione dependence and the PC synthesis deficiency demonstrated in a ΔSpPCS strain, the phytochelatin synthesis in *S. cerevisiae* cells expressing TaPCS1and the phytochelatin synthase activity of purified recombinant SpPCS. The data disclosed herein provide molecular evidence for the model that PCs play a crucial role in metal tolerance (Grill et al., 1985, Science 230:674–676; Zenk, 1996, Gene 179:21–30; Howden et al., 1995, Plant Physiol. 107:1059–1066). The effects of TaPCS1 expression in *S. cerevisiae* on $Cd^{2+}$ tolerance demonstrate that heterologous expression of PCS genes can dramatically enhance metal tolerance. Future research in transgenic plants and other organisms will allow testing of the potential of PCS genes for toxic metal sequestration, metal detoxification, and bioremediation.

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. An isolated nucleic acid encoding a phytochelatin synthase, wherein the synthase shares at least 35% similarity with AtPCS1 (SEQID NO:2).

2. The isolated nucleic acid encoding a phytochelatin synthase of claim 1, wherein said nucleic acid is selected from the group consisting of (SEQ ID NO: 1), (SEQ ID NO: 3), (SEQ ID NO: 5), (SEQ ID NO: 7), and (SEQ ID NO: 9).

3. An isolated nucleic acid encoding a plant phytochelatin synthase, wherein the phytochelatin synthase shares at least 35% similarity with AtPCS1 (SEQID NO:2).

4. The isolated nucleic acid of claim 1, wherein the nucleic acid further comprises a reporter nucleic acid covalently linked thereto.

5. The isolated nucleic acid of claim 4, said reporter nucleic acid encoding a reporter polypeptide selected from the group consisting of a FLAG octapeptide, a human influenza virus hemagglutinin epitope, a β-glucuronidase epitope, a green fluorescent protein epitope, and a luciferase epitope.

6. A recombinant cell comprising the isolated nucleic acid of claim 1.

7. The cell of claim 6, wherein said cell is selected from the group consisting of a prokaryotic cell and a eukaryotic cell.

8. A vector comprising the isolated nucleic acid of claim 1.

9. A transgenic plant stably transformed with an isolated nucleic acid encoding a phytochelatin synthase, wherein the nucleic acid comprises at least one of the group consisting of AtPCS1 (SEQID NO:1), AtPCS2 (SEQID NO:3), TaPCS1 (SEQID NO:5), SpPCS (SEQID NO:7), and CePCS (SEQID NO:9).

10. A transgenic plant stably transformed with an isolated nucleic acid encoding a phytochelatin synthase, wherein the phytochelatin. synthase shares at least 35% similarity with AtPCS1 (SEQID NO:2).

11. A method of generating a transgenic heavy metal resistant plant comprising introducing to the cells of the plant an isolated nucleic acid of claim 1, encoding phytochelatin synthase, thereby generating a transgenic heavy metal resistant plant.

12. A method of decreasing the level of a heavy metal in a harvestable portion of a plant, said method comprising expressing the nucleic acid of claim 1 encoding a phytochelatin synthase in a non-harvestable portion of a plant, thereby decreasing the level of heavy metal in the harvestable portion of the plant.

13. A method of removing a heavy metal from groundwater, said method comprising growing in said groundwater a transgenic plant comprising an isolated nucleic acid encoding a phytochelatin synthase, wherein said phytochelatin synthase comprises a sequence sharing at least 35% similarity with SEQID NO:2, and harvesting said plant from said groundwater, thereby removing said heavy metal from said groundwater.

14. Cells, seeds or progeny of the stably transformed plant of claim 9, each of which comprise the inserted isolated nucleic acid encoding phytochelatin synthase.

15. Cells, seeds or progeny of the stably transformed plant of claim 10, each of which comprise the inserted isolated nucleic acid encoding phytochelatin synthase.

16. A transgenic plant, stably transformed with an isolated nucleic acid encoding a phytochelatin synthase according to claim 1, wherein the phytochelatin synthase shares at least 35% similarity with AtPCS1(SEQID NO:2).

17. A method of generating a transgenic heavy metal resistant plant comprising introducing to the cells of the plant an isolated nucleic acid of claim 2, encoding phytochelatin synthase, thereby generating a transgenic heavy metal resistant plant.

18. A method of decreasing the level of a heavy metal in a harvestable portion of a plant, said method comprising expressing the nucleic acid of claim 2 encoding a phytochelatin synthase in a non-harvestable portion of a plant, thereby decreasing the level of heavy metal in the harvestable portion of the plant.

* * * * *